United States Patent [19]

Takayama et al.

[11] Patent Number: 5,088,492
[45] Date of Patent: Feb. 18, 1992

[54] RADIOACTIVE RAY DETECTING ENDOSCOPE

[75] Inventors: Shuichi Takayama; Masaaki Hayashi; Eiichi Fuse; Koichiro Ishiwara; Mutsumi Yoshikawa; Motoyuki Tagawa; Makoto Inaba, all of Hachioji, Japan

[73] Assignee: Olympus Optical Co., Ltd., Tokyo, Japan

[21] Appl. No.: 593,585

[22] Filed: Oct. 9, 1990

Related U.S. Application Data

[63] Continuation of Ser. No. 245,175, Sep. 15, 1988, abandoned.

[30] Foreign Application Priority Data

| Sep. 16, 1987 | [JP] | Japan | 62-231658 |
| May 23, 1988 | [JP] | Japan | 63-126588 |
| Jul. 21, 1988 | [JP] | Japan | 63-96907[U] |
| Jul. 21, 1988 | [JP] | Japan | 63-182194 |
| Jul. 21, 1988 | [JP] | Japan | 63-182195 |
| Jul. 21, 1988 | [JP] | Japan | 63-182196 |
| Jul. 26, 1988 | [JP] | Japan | 63-187769 |
| Aug. 10, 1988 | [JP] | Japan | 63-200463 |

[51] Int. Cl.$^5$ ............... A61B 6/00; A61B 1/00
[52] U.S. Cl. .................... 128/654; 128/4; 128/6; 128/659; 358/98
[58] Field of Search ............... 128/4, 6, 654, 656, 128/657, 658, 659; 358/98

[56] References Cited

U.S. PATENT DOCUMENTS

| 4,015,592 | 4/1977 | Bradley-Moore | 128/654 |
| 4,618,885 | 10/1986 | Nagasaki et al. | 358/98 |
| 4,631,582 | 12/1986 | Nagasaki et al. | 358/98 |
| 4,653,478 | 3/1987 | Nagasaki et al. | 128/6 |
| 4,667,656 | 5/1987 | Yabe | 128/6 |

Primary Examiner—Kyle L. Howell
Assistant Examiner—Krista M. Pfaffle
Attorney, Agent, or Firm—Armstrong, Nikaido, Marmelstein, Kubovcik & Murray

[57] ABSTRACT

A radioactive ray detecting endoscope comprises an elongated insertable part having an observing window in the tip part, an imaging apparatus converting an image of an observed part obtained through the observing window to an electric signal and a radioactive ray detecting apparatus detecting radioactive rays from inside the visual field of the imaging apparatus. The imaging apparatus has, for example, a solid state imaging device imaging an optical image of an object. Also, a collimator regulating the radioactive ray detecting direction is provided, for example, around the radioactive ray detecting apparatus.

33 Claims, 28 Drawing Sheets

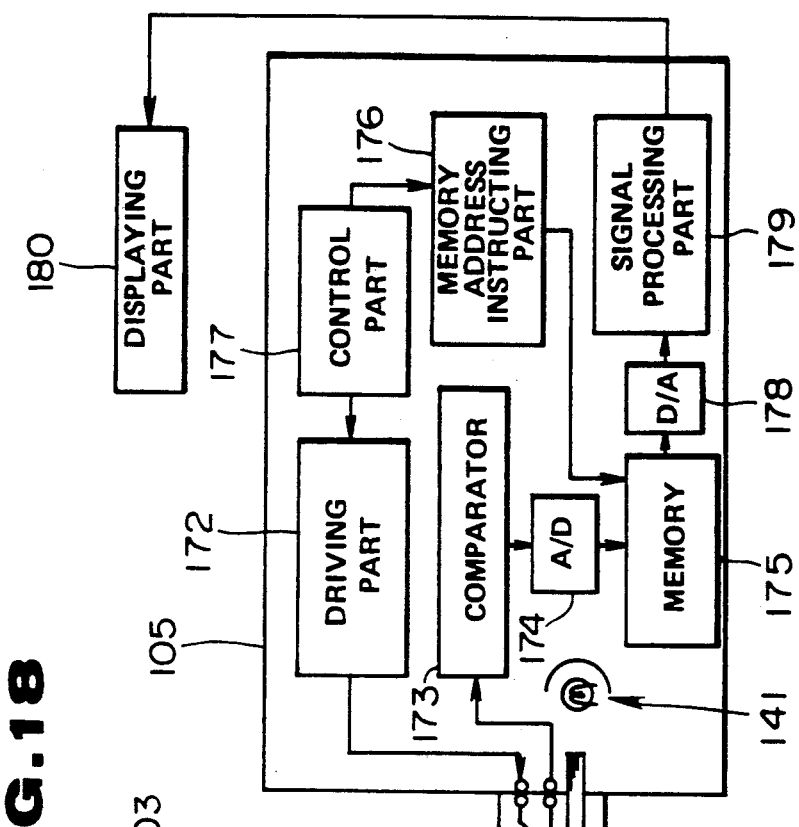
FIG. 18
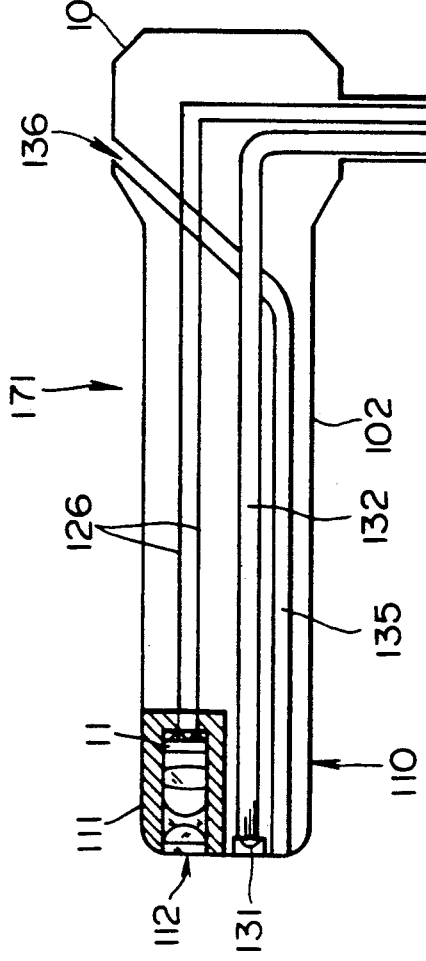
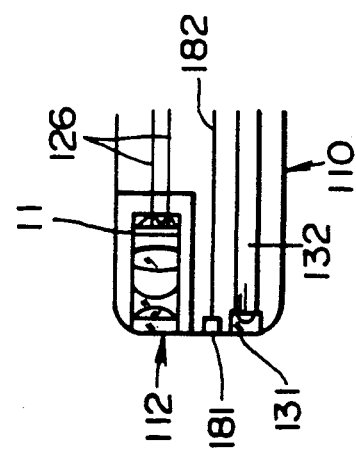
FIG. 19

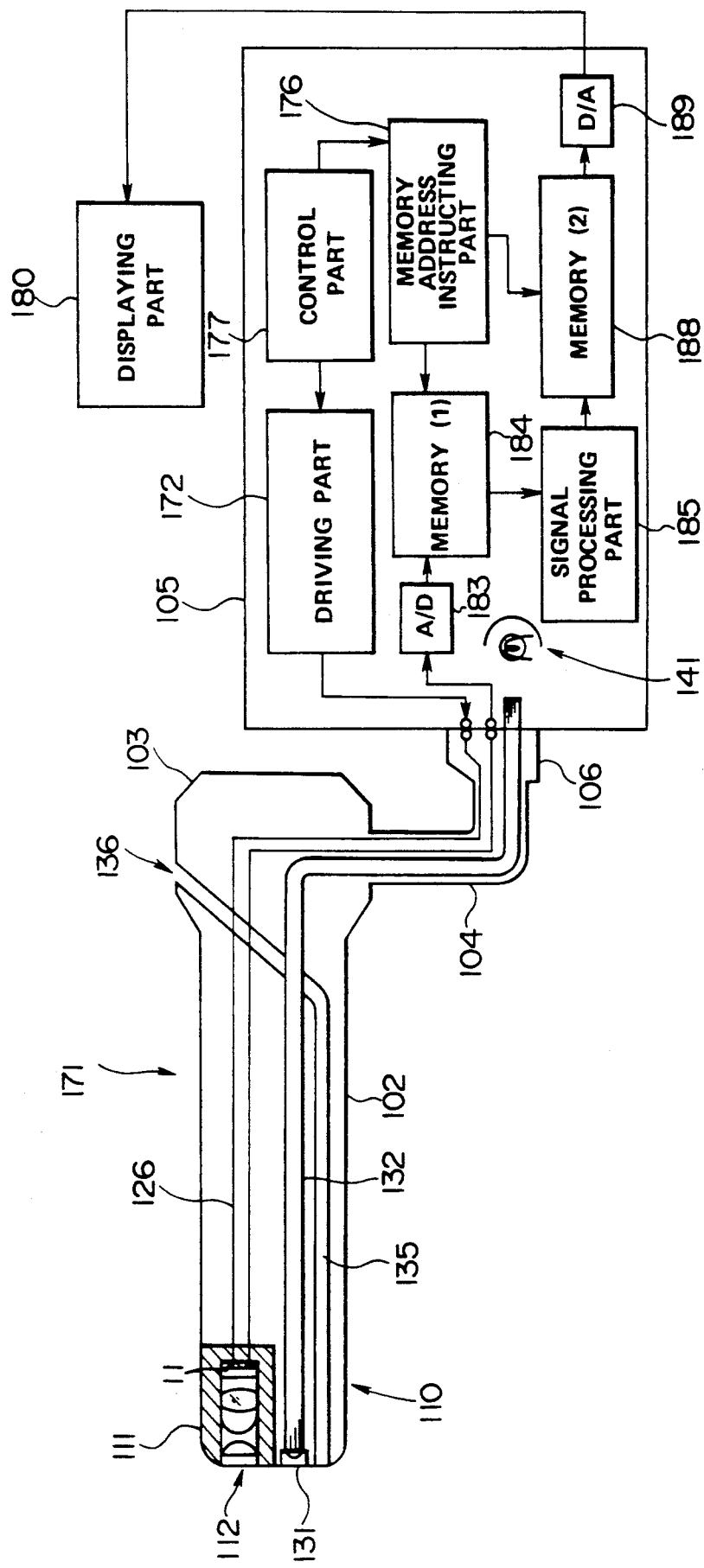

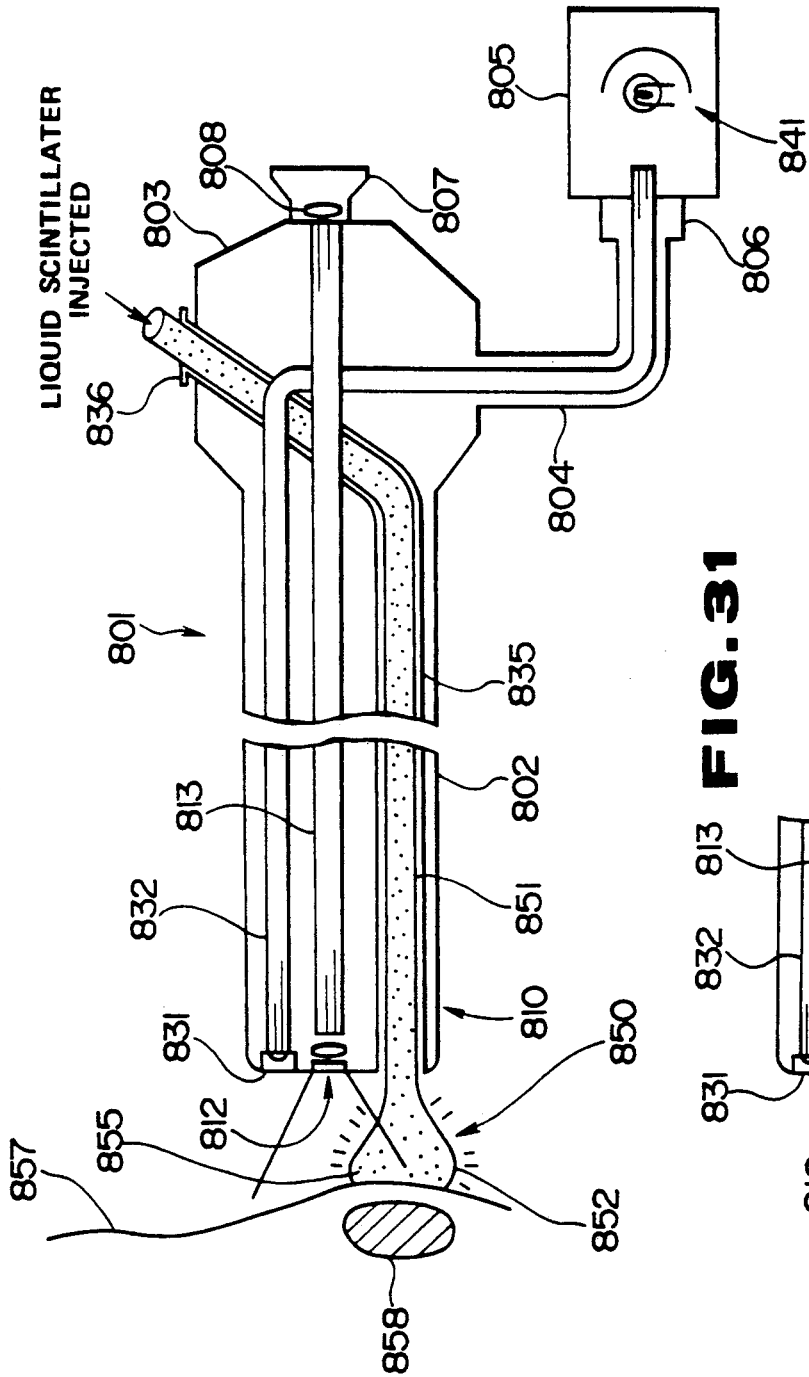

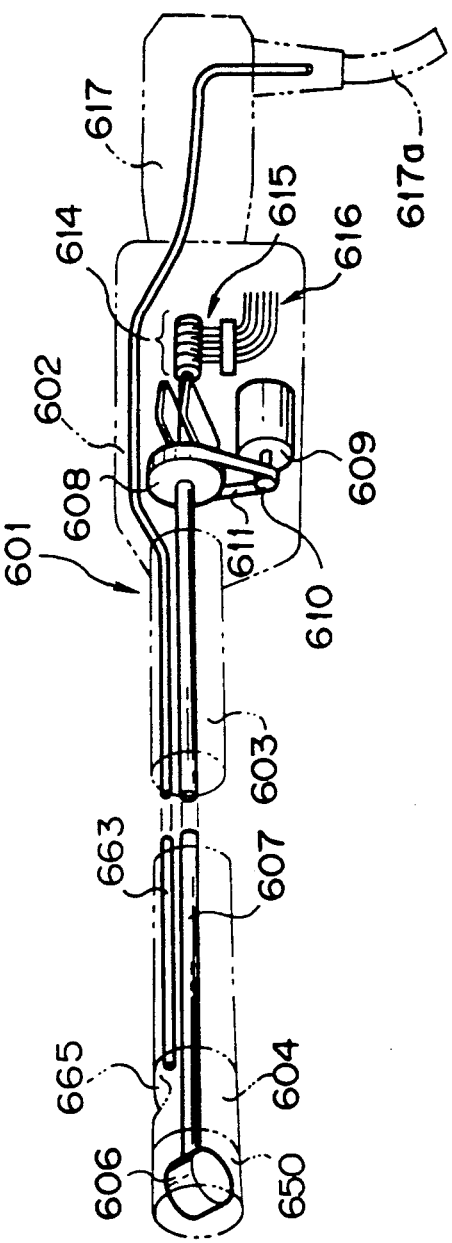

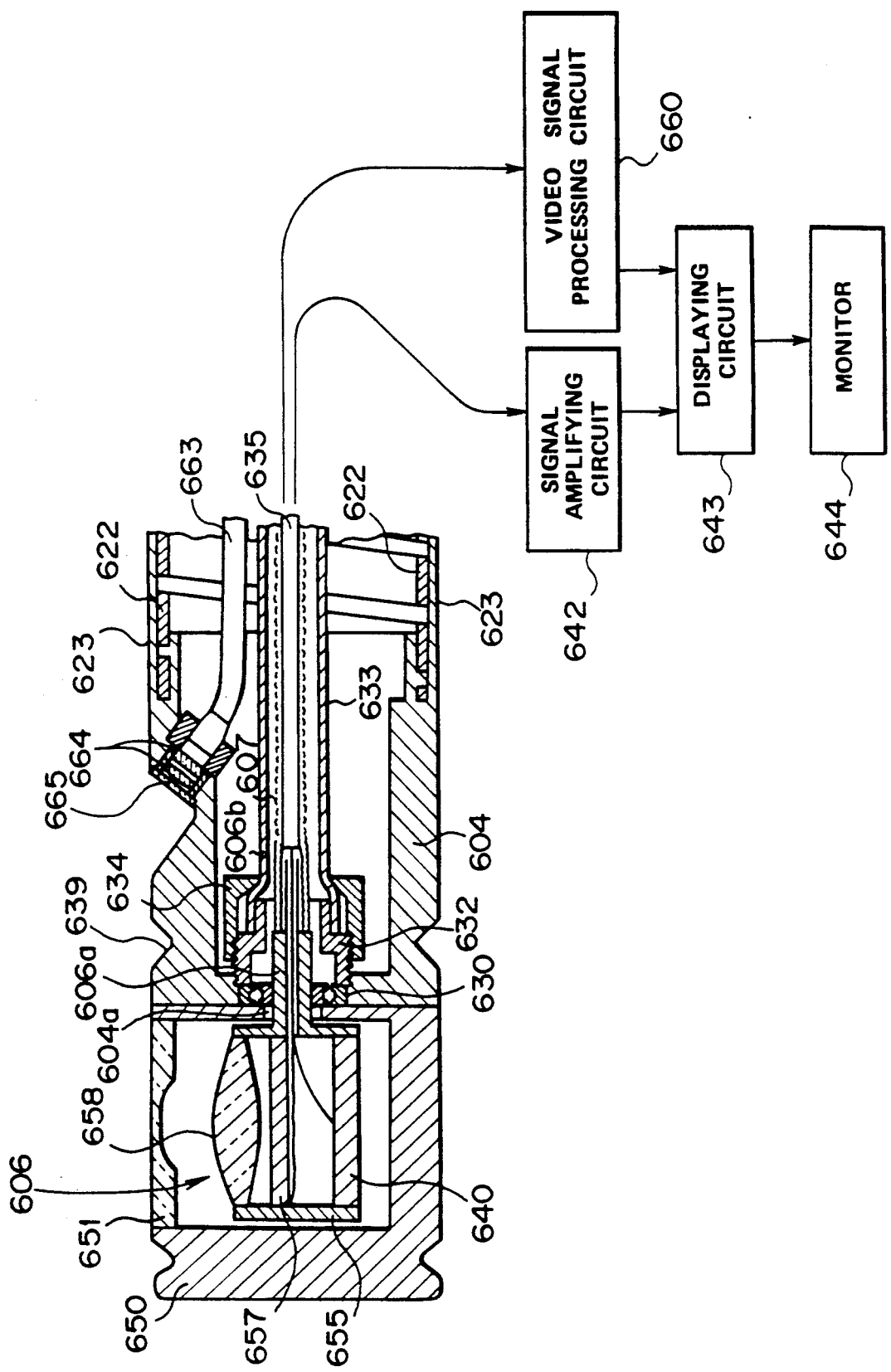

RADIOACTIVE RAY DETECTING ENDOSCOPE

This application is a continuation of application Ser. No. 245,175 filed Sept. 15, 1988, now abandoned.

BACKGROUND OF THE INVENTION

1. Field of the Invention

This invention relates to an endoscope whereby radioactive rays can be detected.

2. Related Art Statement

Recently, there is extensively used an endoscope whereby organs within a body cavity can be observed by inserting an elongated insertable part into the body cavity or, as required, various therapeutic treatments can be made by using a treating tool inserted through a treating tool channel.

Now as a means of discovering and diagnosing a cancer, a substance concentrating peculiarly on a cancer cell is marked with a radioactive substance and the radioactive rays emitted from the cancer cell are detected to discover the presence, penetration range or transfer of the cancer.

Conventionally, as shown in the publication, for example, of a Japanese utility model publication No. 5168/1972, a sensor for detecting such a radioactive ray as a β ray has been led into a body by using a fiber scope to detect and diagnose the presence of a cancer. A cancer resistor as is marked by $F_{18}$ has been used as a substance concentrating peculiarly on a cancer.

A probe fitted, for example, with a semiconductor radioactive ray detector is disclosed in the publication of each of a Japanese utility model publication No. 4526/1973. Japanese patent publication No. 40518/1970. U.S. Pat. No. 3,665,916, 3,339,095 and 4,595,014.

However, with the above mentioned probe, radioactive rays within a living body can be detected but the radioactive ray generating part can not be observed.

Also, with a radioactive ray detecting means provided in a fiber scope as shown in the publication of the Japanese utility model publication No. 5168/1972, it is difficult to obtain the radioactive ray information while observing the observed part from the eyepiece part. That is to say, by once separating the eye from the eyepiece part, the radioactive ray information displaying means must be seen. Therefore, it is difficult to make the endoscope image and the radioactive ray generating source correspond to each other. Particularly, it has been difficult to confirm the position of a deep part cancer or lymphatic knot transfer.

OBJECTS AND SUMMARY OF THE INVENTION

An object of the present invention is to provide a radioactive ray detecting endoscope whereby an endoscope observed image and radioactive ray information can be simultaneously seen and the endoscope observed image and radioactive ray generating source can be easily made to correspond to each other.

Another object of the present invention is to provide a radioactive ray detecting endoscope whereby the position of a radioactive ray generating source can be easily confirmed in an endoscope observed image.

Further, another object of the present invention is to provide a radioactive ray detecting endoscope whereby radioactive rays can be detected without making the tip of the insertable part large.

Further, another object of the present invention is to provide a radioactive ray detecting endoscope whereby the presence of a radioactive generating source can be known in the endoscope observed image and an image in which the influence of the radioactive rays is reduced can be also obtained.

Further, another object of the present invention is to provide a radioactive ray detecting endoscope whereby the influence of radioactive rays from outside the object part can be reduced.

The radioactive ray detecting endoscope of the present invention comprises an elongated insertable part having an observing window in the tip part, an imaging device converting to an electric signal the image of the observed part obtained through the above mentioned observing window and a radioactive ray detecting device detecting radioactive rays from inside the visual field of the above mentioned imaging device. The above mentioned imaging device has, for example, a solid state imaging device for imaging the optical image of an object to be imaged. Preferably, a collimator regulating the radioactive ray detecting direction is provided around the above mentioned radioactive ray detecting device.

The other features and advantages of the present invention will become apparent enough with the following explanation.

BRIEF DESCRIPTION THE DRAWINGS

FIGS. 1 and 2 relate to the first embodiment of the present invention.

FIG. 1 is an explanatory view showing the formation of an endoscope apparatus.

FIGS. 2 (A) to (F) are timing charts for explaining the operation of this embodiment.

FIGS. 3 and 4 relate to the second embodiment of the present invention.

Figure 7:
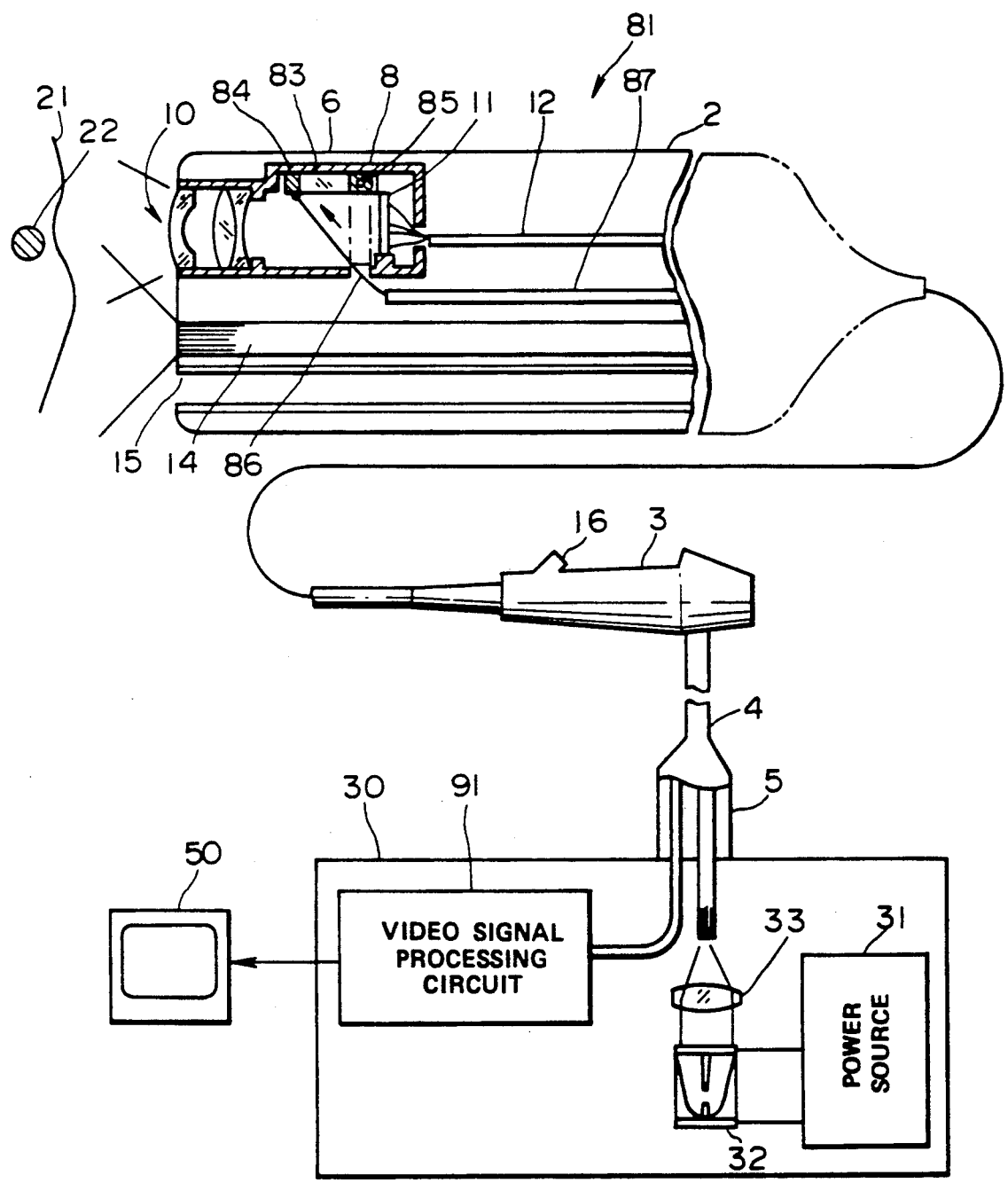
Figure 8:
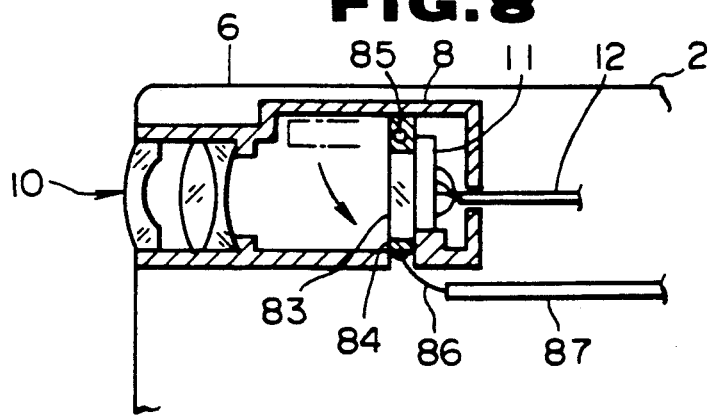

FIGS. 7 and 8 relate to the fifth embodiment of the present invention.

FIG. 7 is an explanatory view showing the formation of an endoscope apparatus.

FIG. 8 is an explanatory view of a tip part of an endoscope when a filter is inserted.

Figure 9:
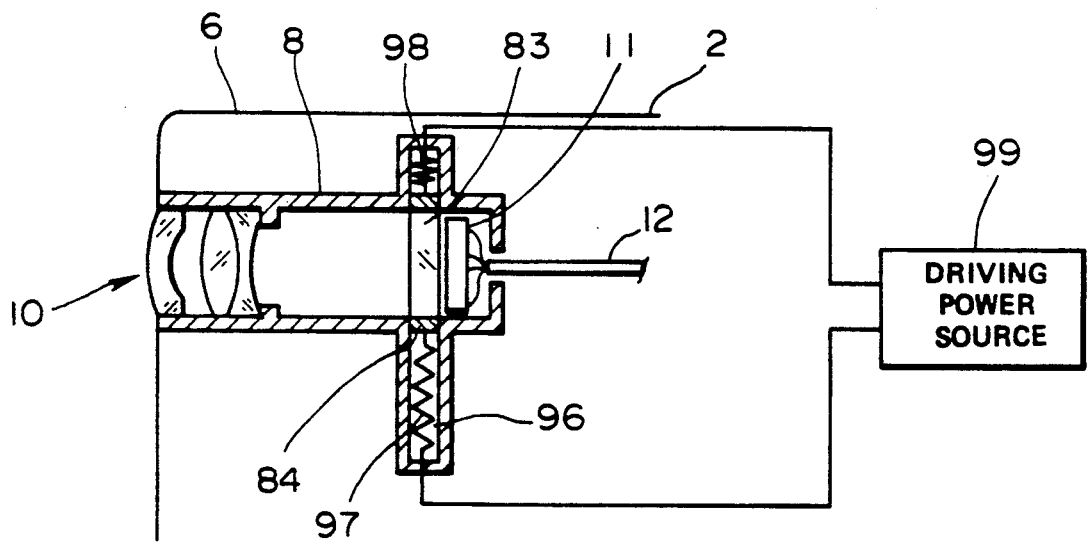

FIG. 9 is an explanatory view of a tip part of an endoscope in the sixth embodiment of the present invention.

Figure 10:
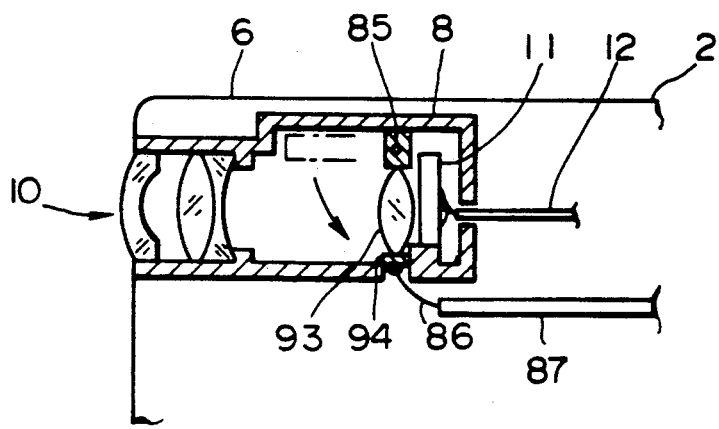

FIG. 10 is an explanatory view of a tip part of an endoscope in the seventh embodiment of the present invention.

FIGS. 11 to 15 relate to the eighth embodiment of the present invention.

Figure 11:
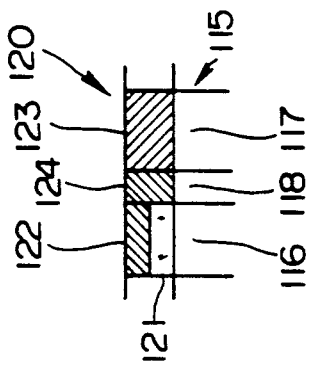

FIG. 11 is an explanatory view showing an arrangement of pixels of a solid state imaging device.

Figure 12:
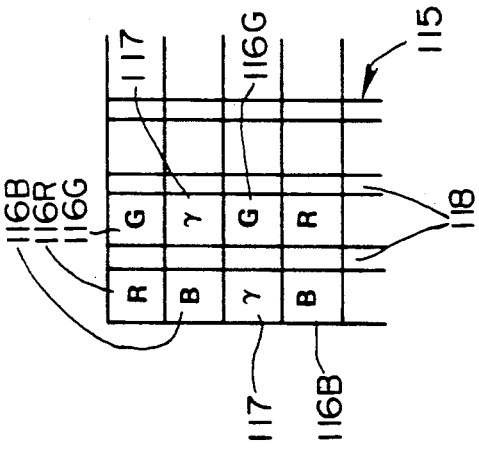

FIG. 12 is a sectioned view of a filter member provided on the front surface of a solid state imaging device.

Figure 13:
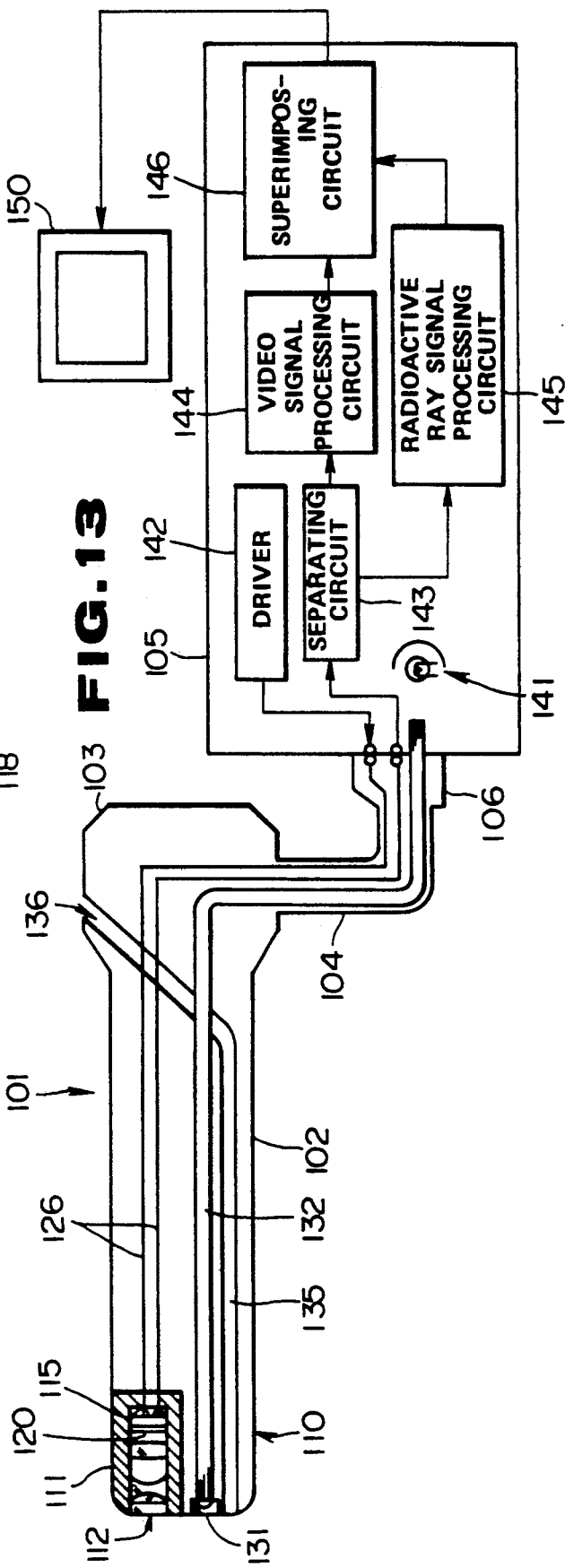

FIG. 13 is an explanatory view showing the formation of an endoscope apparatus.

Figure 14A:
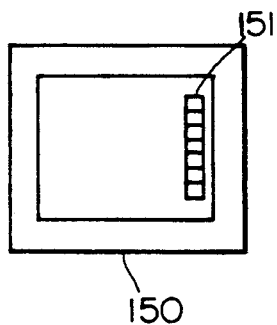
Figure 14B:
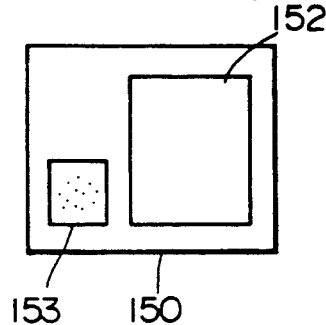
Figure 14C:
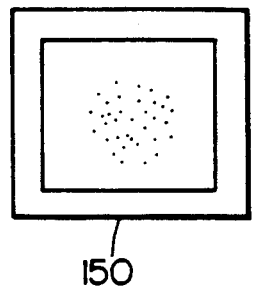

FIGS. 14 (A) to (C) are explanatory views showing respectively examples of the display of a monitor.

Figure 15:
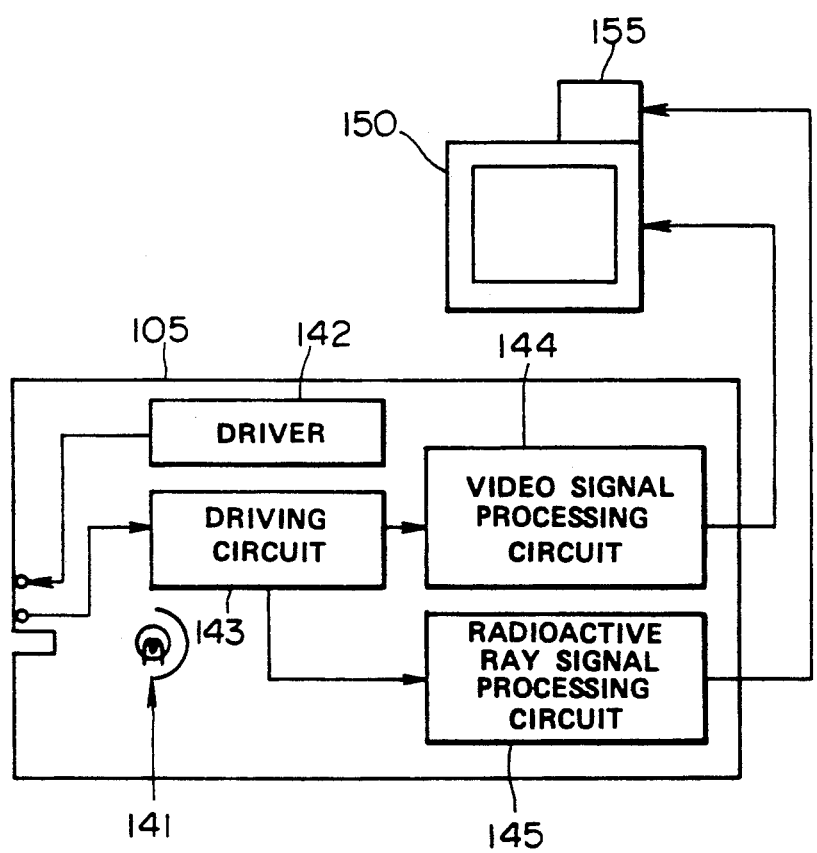

FIG. 15 is an explanatory diagram showing the formation of a processing apparatus in a modification of this embodiment.

Figure 16:
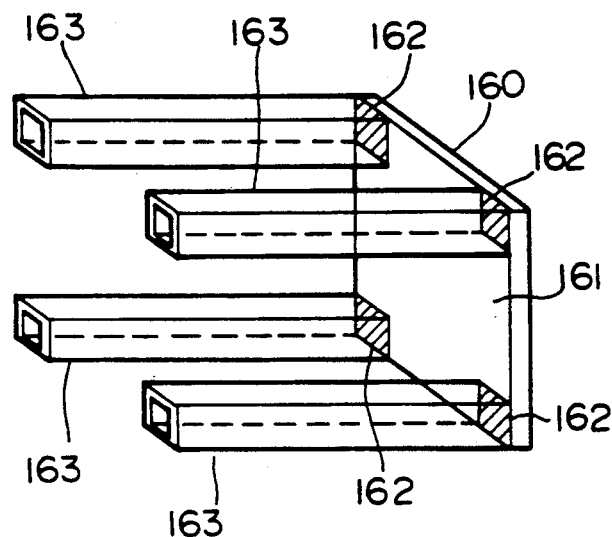
Figure 17:
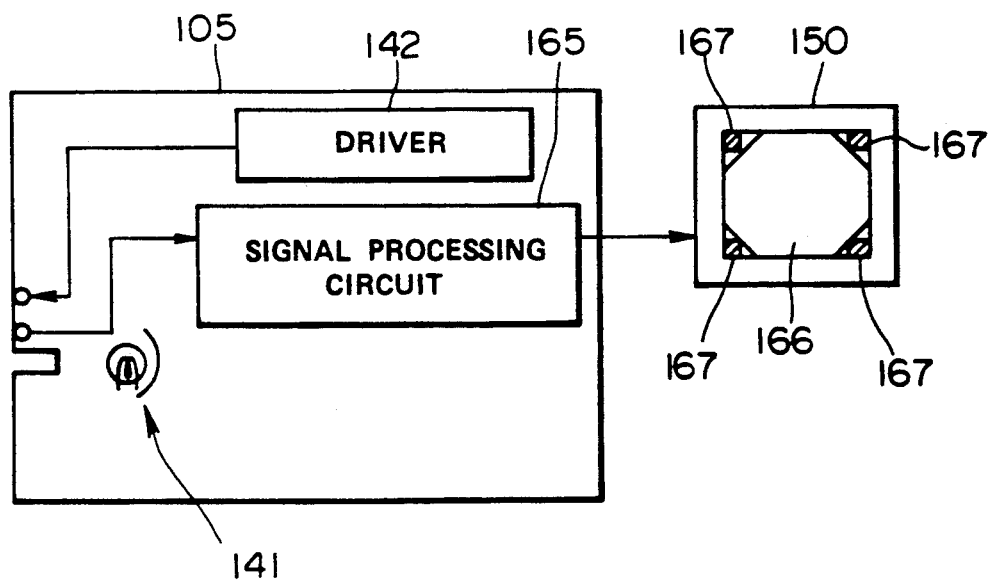

FIGS. 16 and 17 relate to the ninth embodiment of the present invention.

FIG. 16 is a perspective view of a CCD and collimator.

FIG. 17 is an explanatory diagram showing a control apparatus and monitor.

FIGS. 18 and 19 relate to the tenth embodiment of the present invention.

FIG. 18 is an explanatory diagram showing the formation of an endoscope apparatus.

FIG. 19 is an explanatory view of a tip part of an endoscope in a modification of this embodiment.

Figures 21A, 21B, 21C:
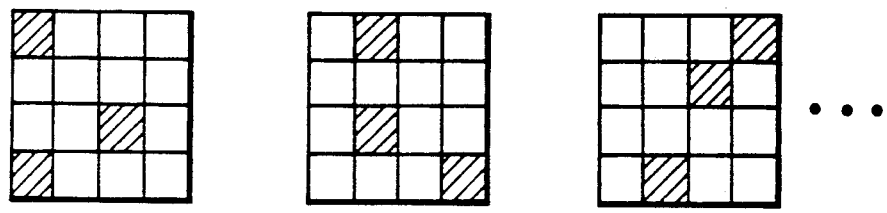

FIGS. 20 and 21 relate to the 11th embodiment of the present invention.

FIG. 20 is an explanatory diagram showing the formation of an endoscope apparatus.

FIGS. 21 (A) to (C) are explanatory views showing the operation of this embodiment.

Figure 22:
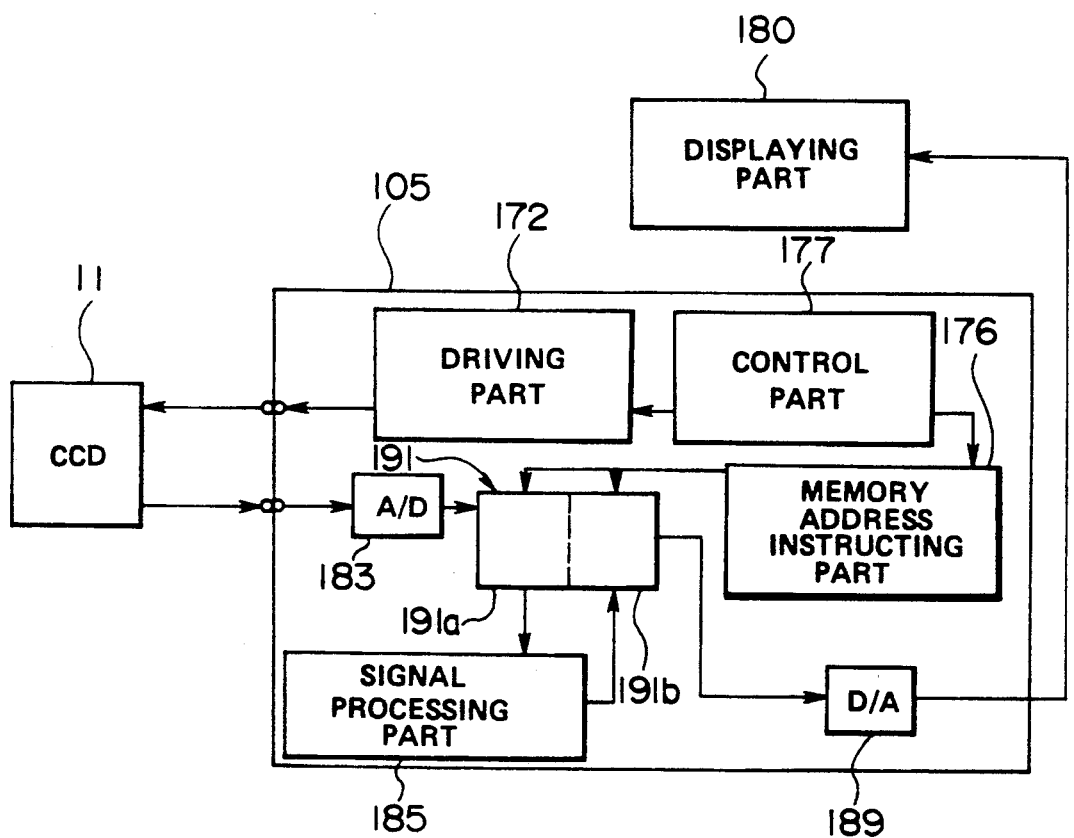

FIG. 22 is a block diagram showing the formation of a control apparatus in the 12th embodiment of the present invention.

Figure 23:
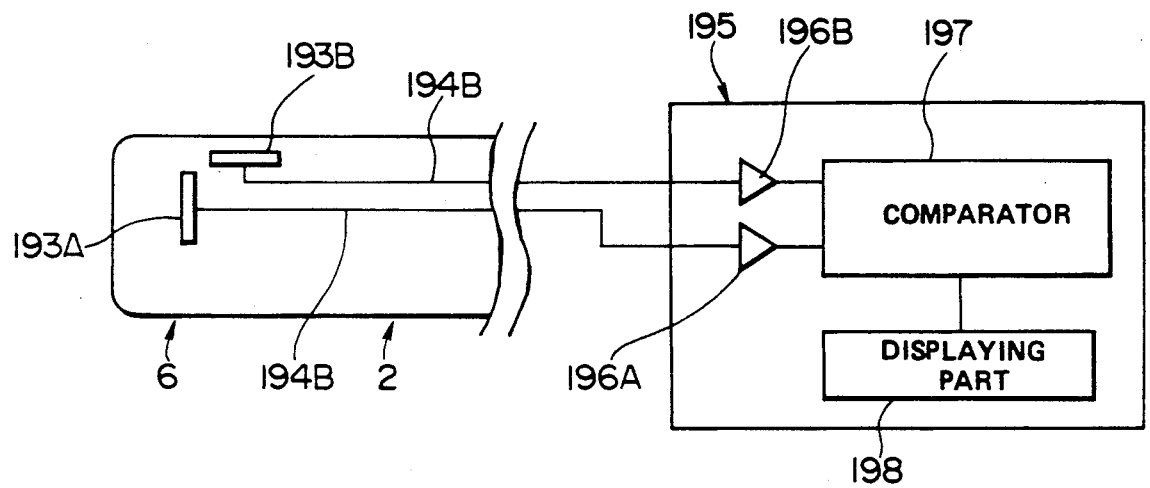
Figure 24:
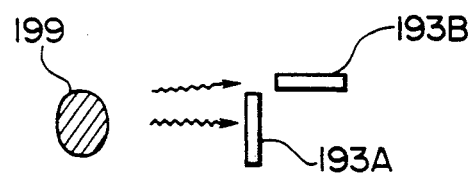
Figure 25:
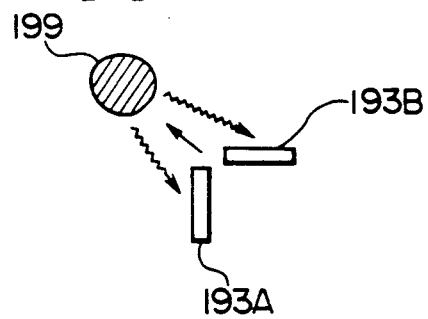

FIGS. 23 to 25 relate to the 13th embodiment of the present invention.

FIG. 23 is an explanatory diagram showing a radioactive ray detecting means of an endoscope.

FIG. 24 and 25 explanatory views showing respectively the position relations of a radioactive ray generating source and two CCD's.

Figure 26:
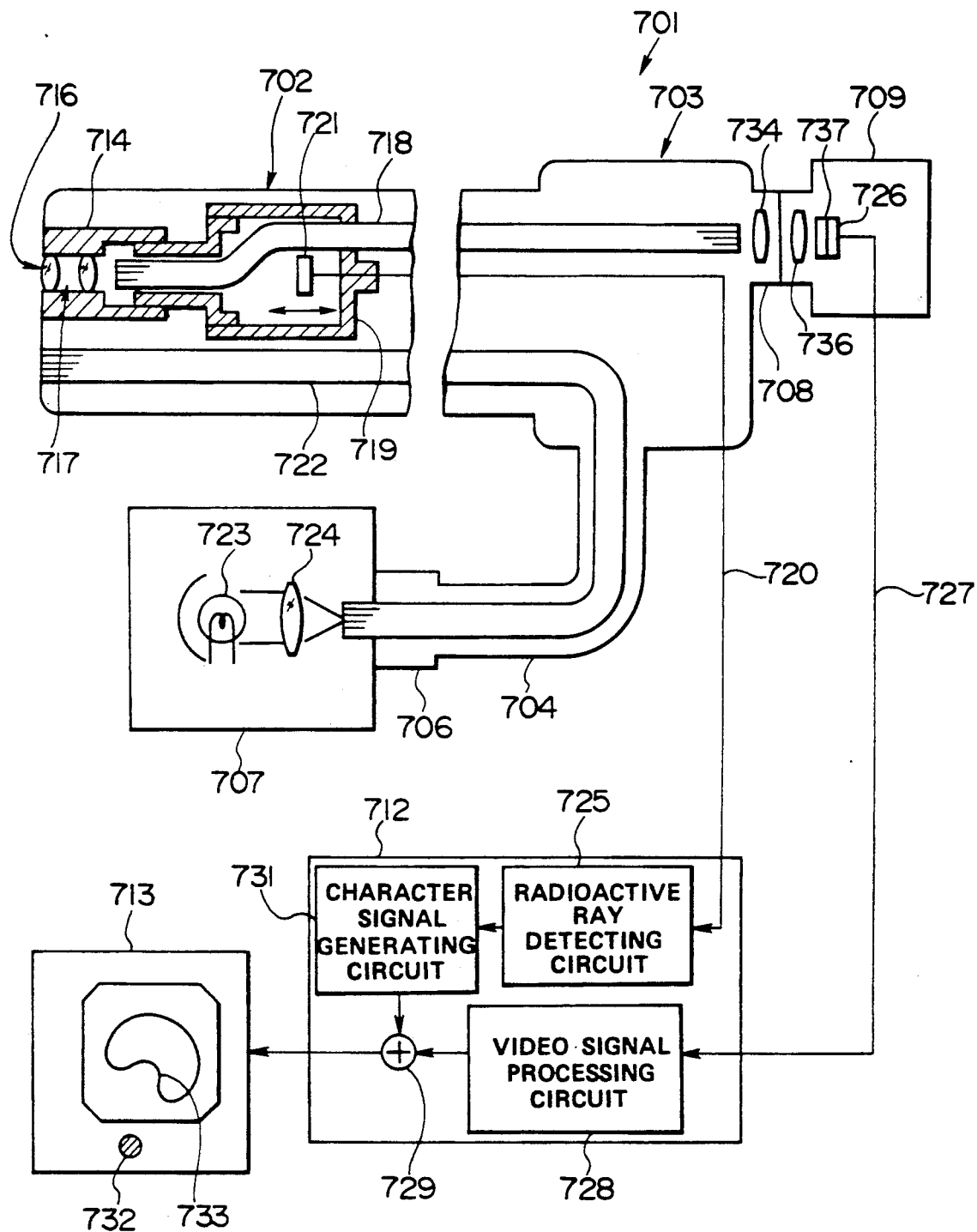
Figure 27:
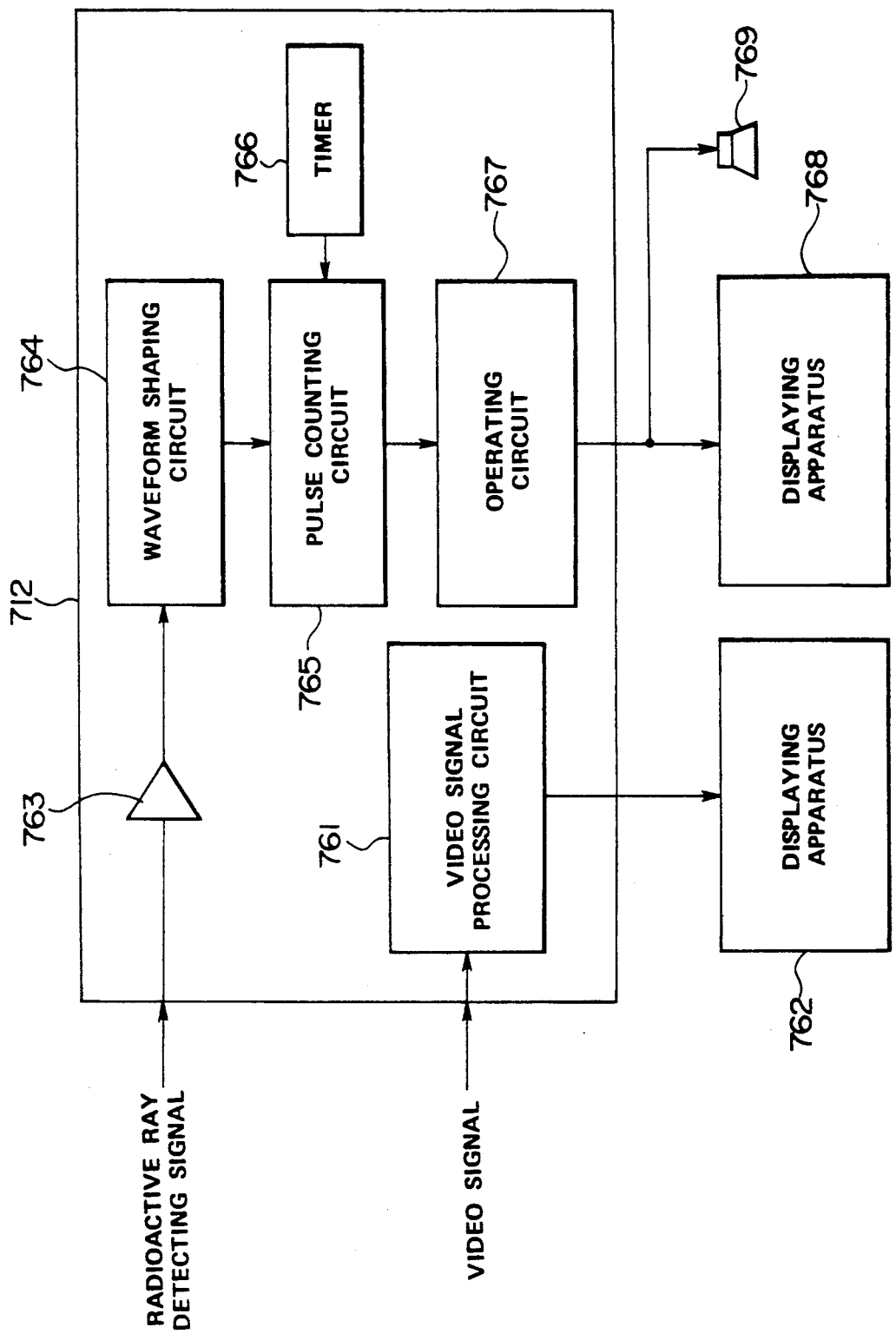

FIGS. 26 and 27 relate to the 14th embodiment of the present invention.

FIG. 26 is an explanatory diagram showing the formation of an endoscope apparatus.

FIG. 27 is a block diagram showing a modification of a video processing apparatus.

Figure 28:
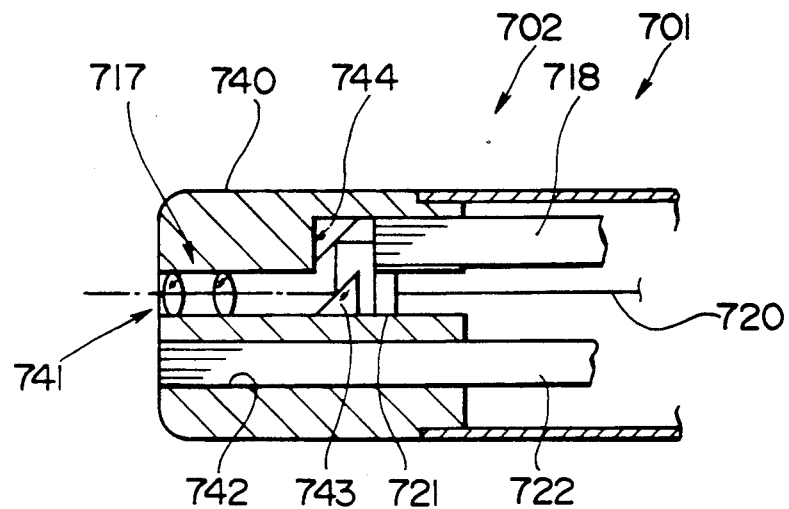

FIG. 28 is an explanatory view showing the formation of an endoscope tip part in the 15th embodiment of the present invention.

Figure 29:
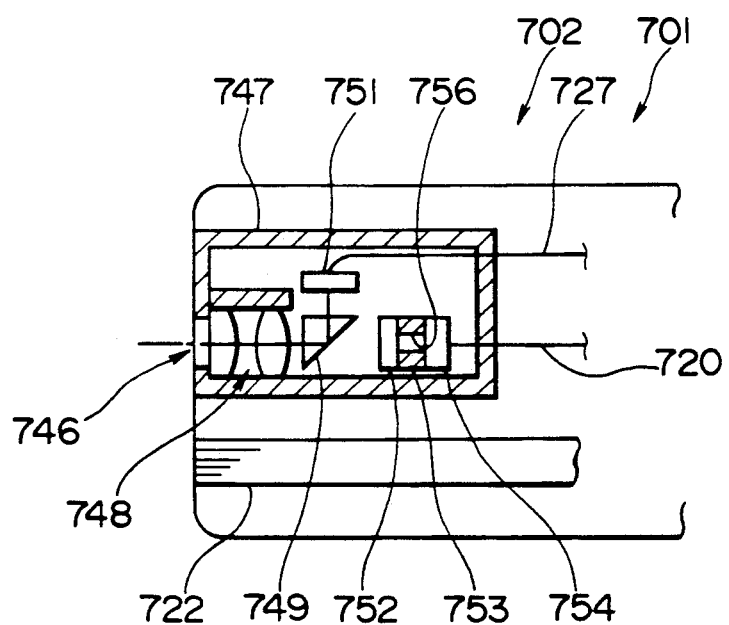

FIG. 29 is an explanatory view showing the formation of an endoscope tip part in the 16th embodiment of the present invention.

FIG. 30 is an explanatory view showing the formation of an endoscope apparatus in the 17th embodiment of the present invention.

FIG. 31 is an explanatory view showing the formation of an endoscope tip part in the 18th embodiment of the present invention.

Figure 32:
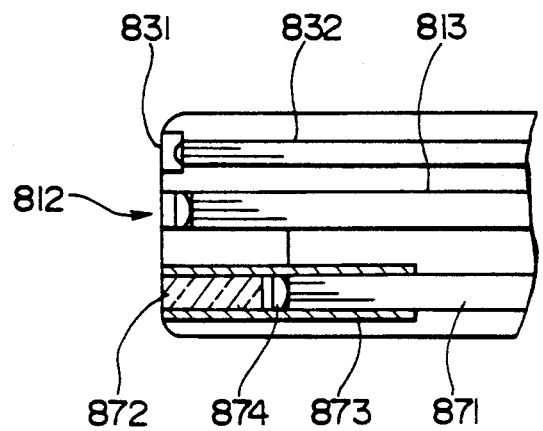

FIG. 32 is an explanatory view showing the formation of an endoscope tip part in the 19th embodiment of the present invention.

Figure 33:
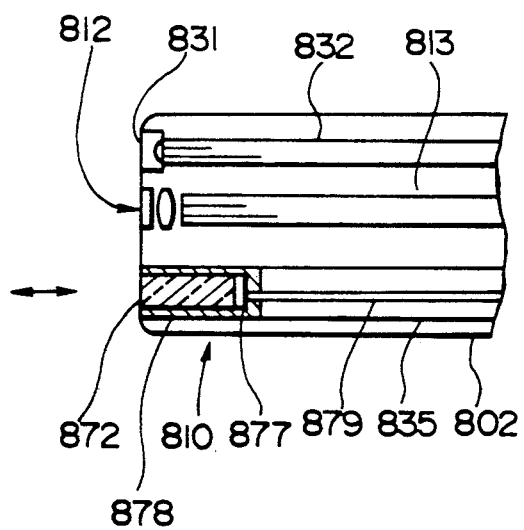

FIG. 33 is an explanatory view showing the formation of an endoscope tip part in the 20th embodiment of the present invention.

Figure 34:
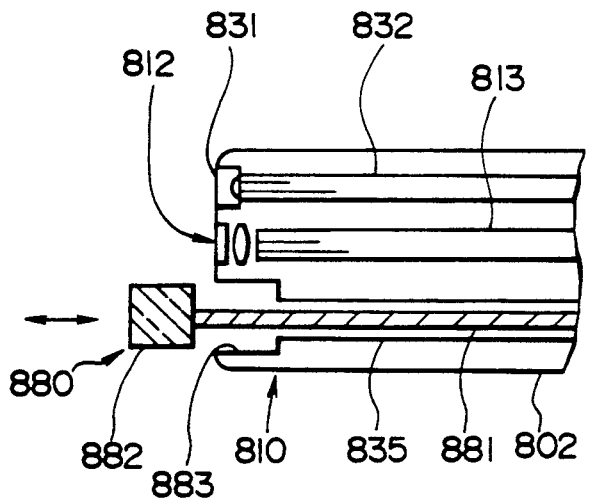

FIG. 34 is an explanatory view showing the formation of an endoscope tip part in the 21st embodiment of the present invention.

Figure 35:
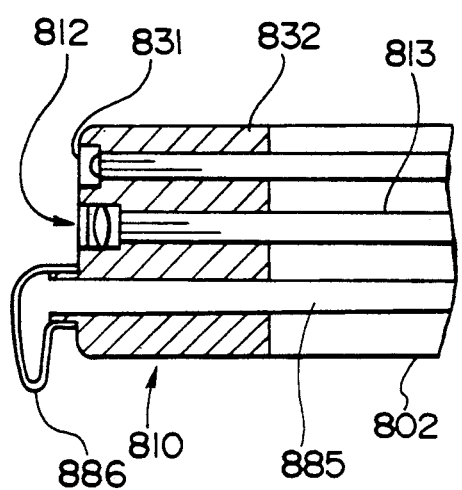
Figure 36:
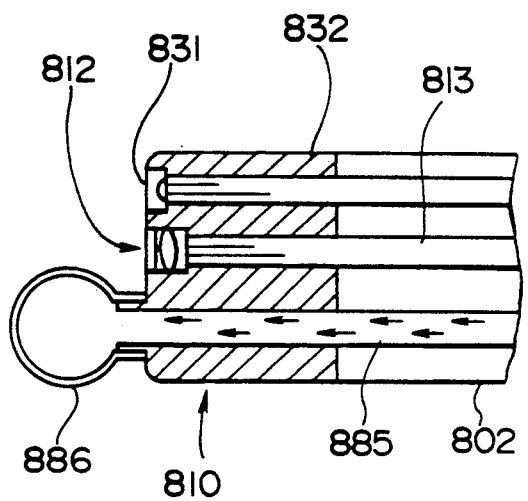

FIGS. 35 and 36 relate to the 22nd embodiment of the present invention.

FIG. 35 is an explanatory view of an endoscope tip part as a balloon is contracted.

FIG. 36 is an explanatory view of an endoscope tip part as a balloon is inflated.

Figure 37:
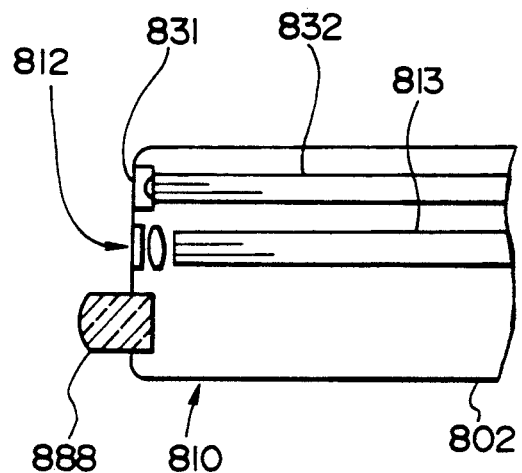

FIG. 37 is an explanatory view showing the formation of an endoscope tip part in the 23rd embodiment of the present invention.

Figure 38:
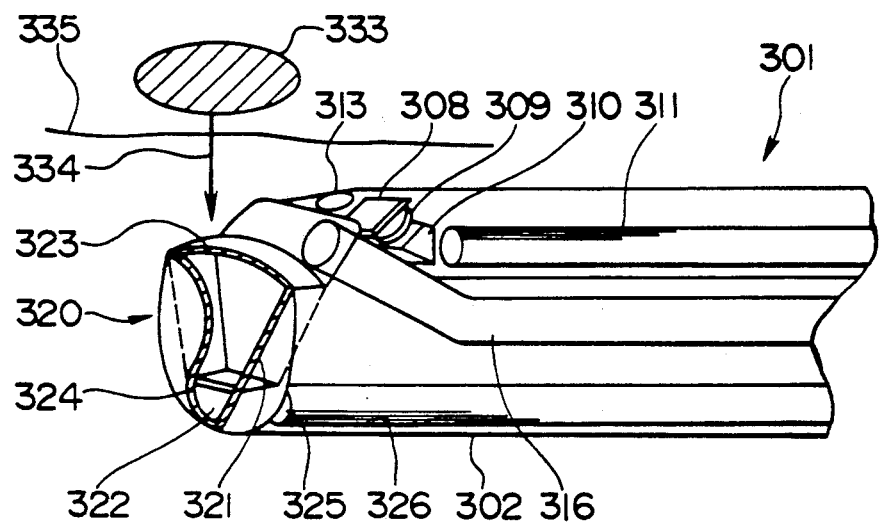
Figure 39:
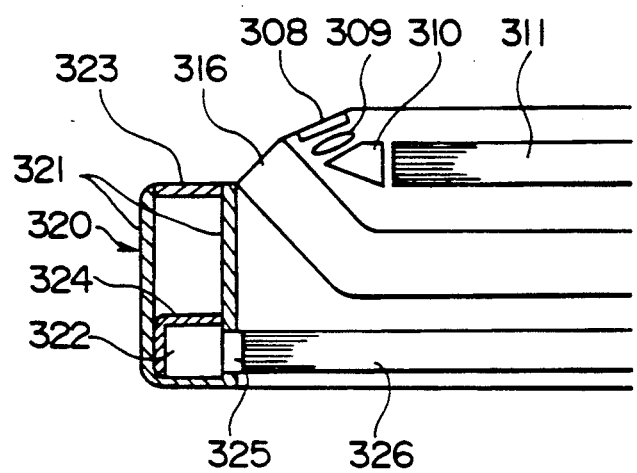
Figure 40:
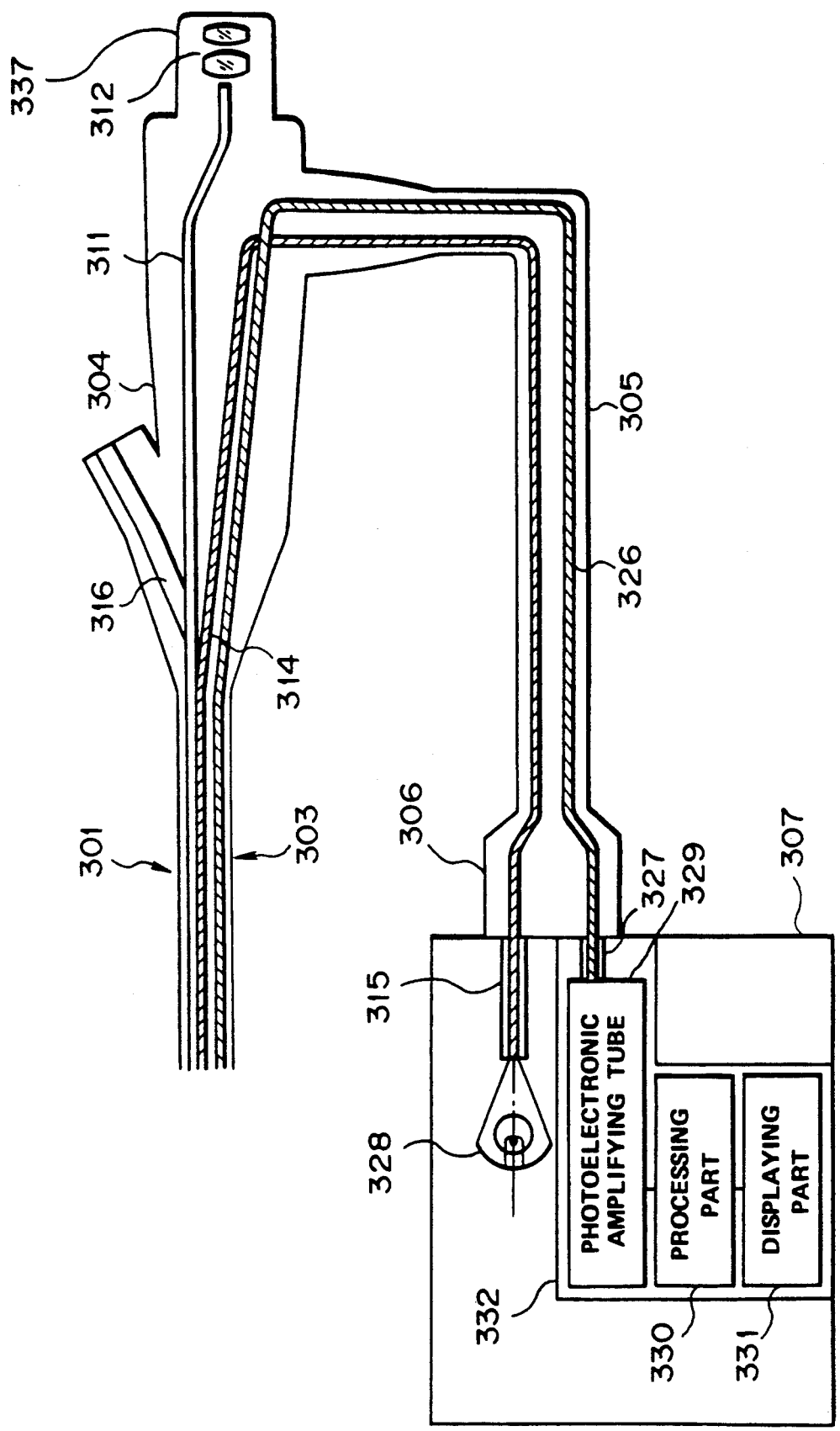

FIGS. 38 to 40 relate to the 24th embodiment of the present invention.

FIG. 38 is a sectioned perspective view of an endoscope tip part.

FIG. 39 is a vertically sectioned view of FIG. 38.

FIG. 40 is an explanatory view showing the operating part side of an endoscope.

Figure 41:
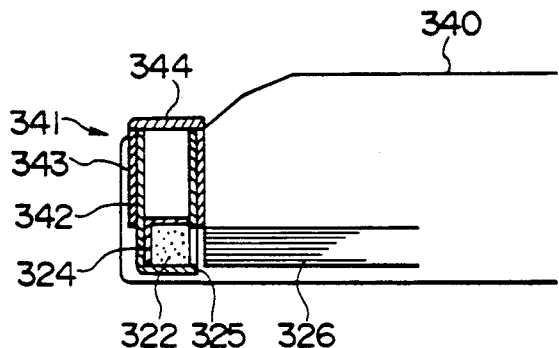
Figure 42:
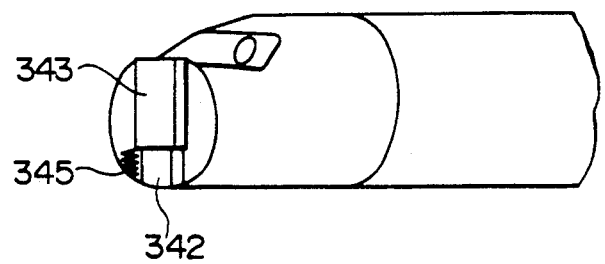
Figure 43:
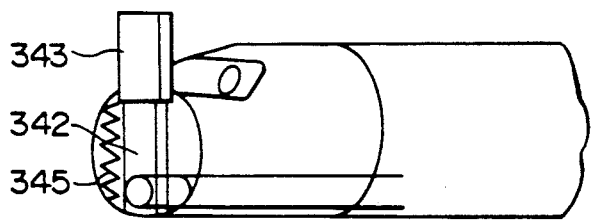

FIGS. 41 to 43 relate to the 25th embodiment of the present invention.

FIG. 41 is an explanatory view showing an endoscope tip part.

FIG. 42 is a perspective view of an endoscope tip part.

FIG. 43 is a perspective view of an endoscope tip part as a second tube is extended out.

Figure 44:
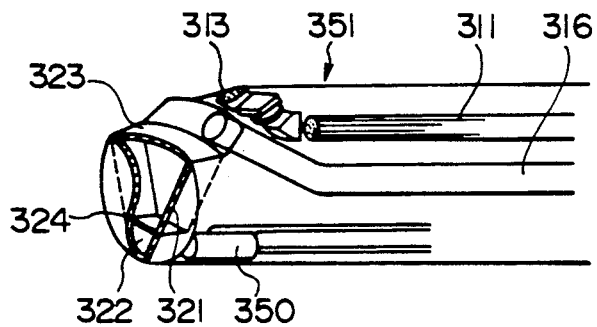

FIG. 44 is an explanatory view showing an endoscope tip part in the 26th embodiment.

FIG. 45 to 53 relate to the 27th embodiment of the present invention.

Figure 45:
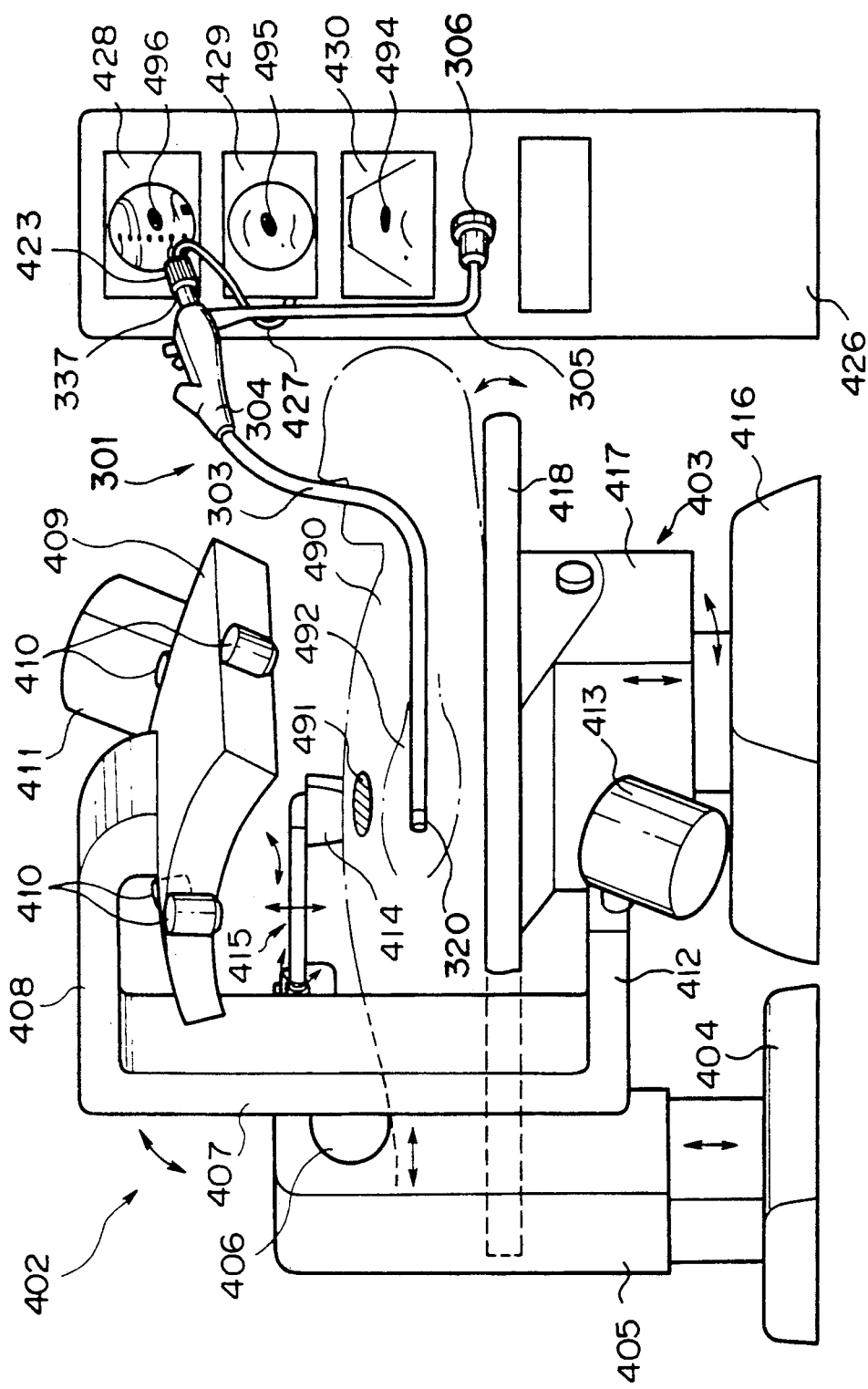

FIG. 45 is an explanatory view showing the formation of an endoscope apparatus.

Figure 46:
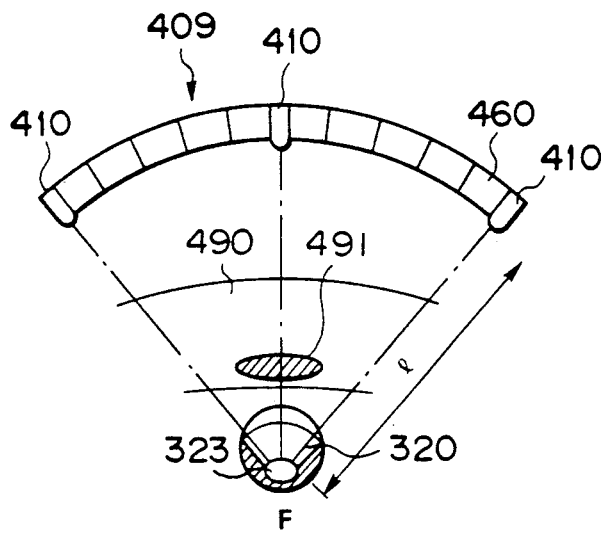

FIG. 46 is an elevation of a body outside type radioactive ray detecting part.

Figure 47:
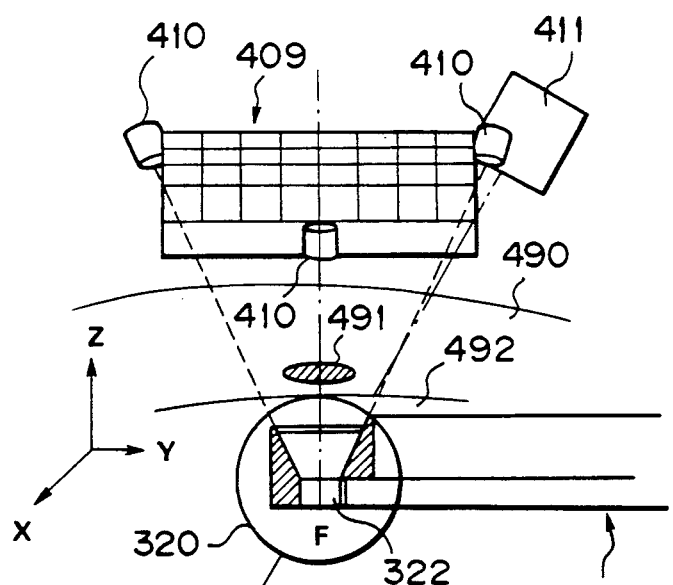

FIG. 47 is a side view of the body outside type radioactive ray detecting part.

Figure 48:
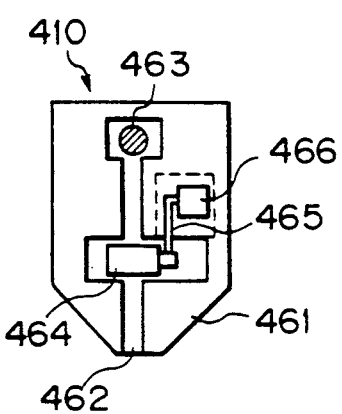

FIG. 48 is an explanatory view showing a $\gamma$ ray generating part.

Figure 49:
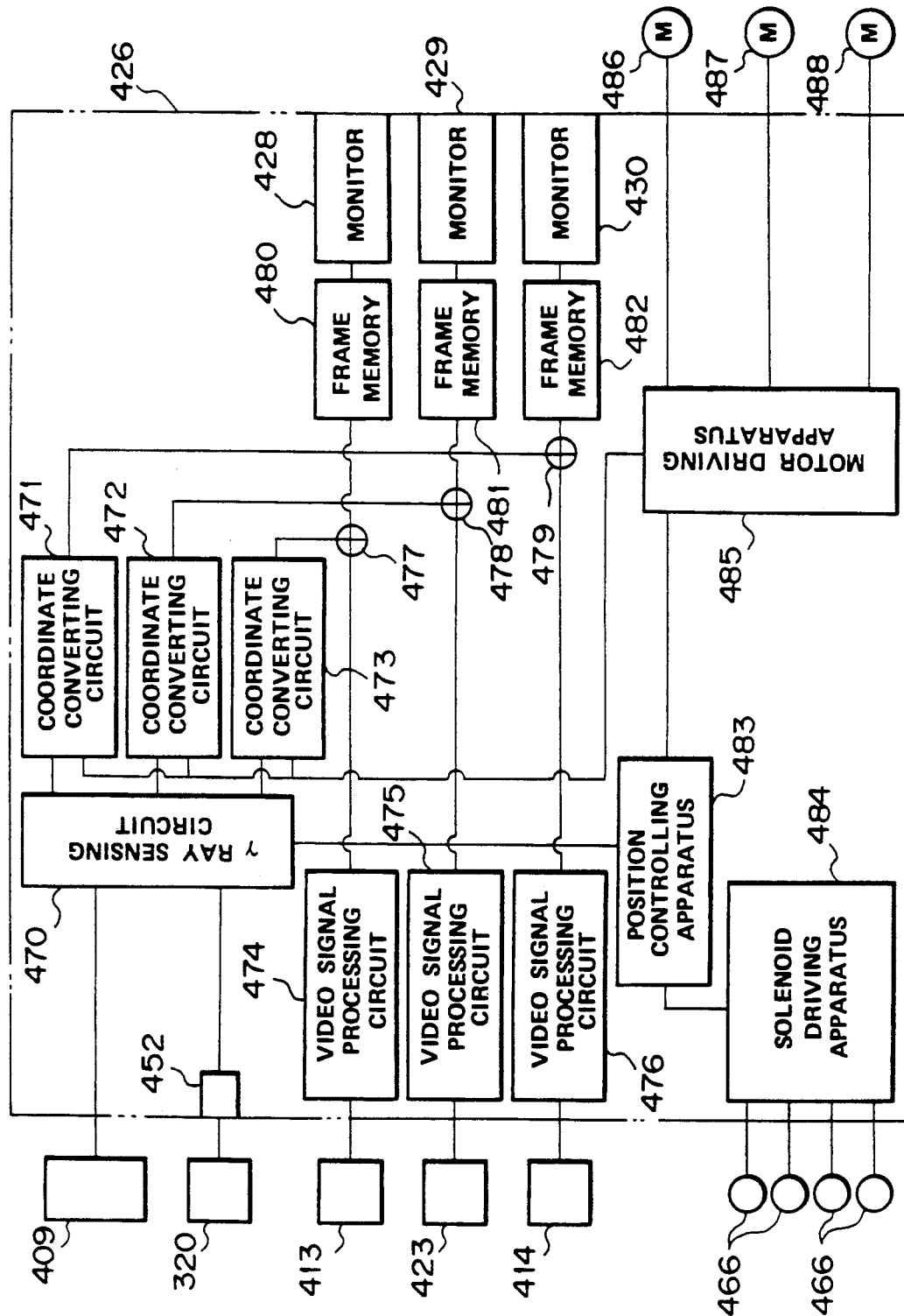

FIG. 49 is a block diagram of a data processing apparatus.

FIGS. 50 to 53 relate to another example of an endoscope.

Figure 50:
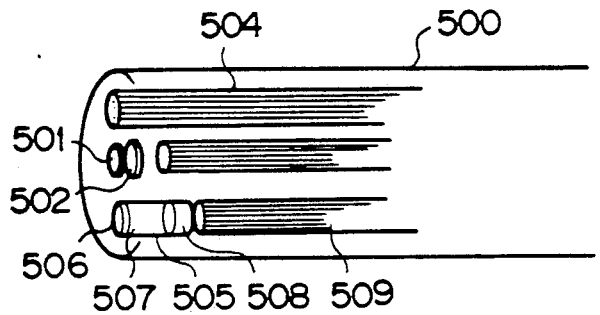

FIG. 50 is an explanatory diagram showing another first example of an endoscope.

Figure 51:
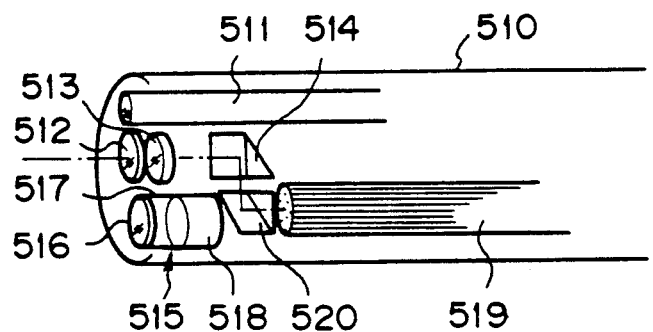

FIG. 51 is an explanatory view showing another second example of an endoscope.

Figure 52:
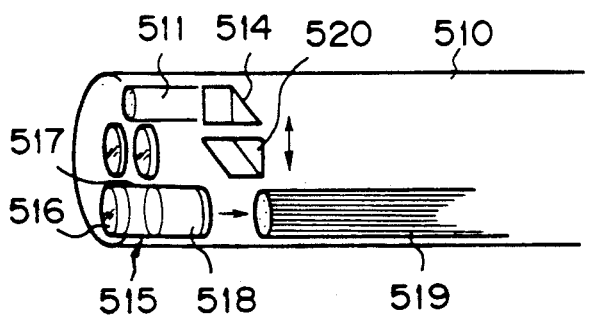

FIG. 52 is an explanatory view showing the operation of the endoscope of FIG. 51.

Figure 53:
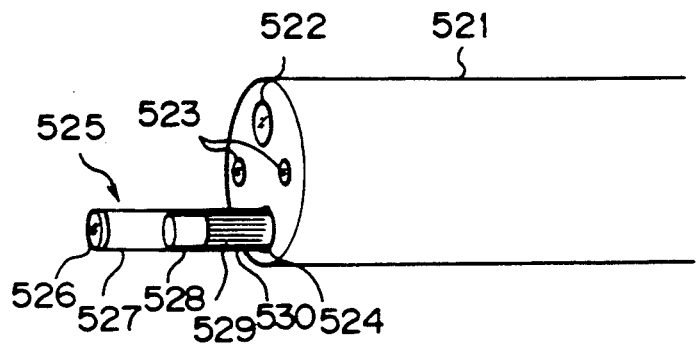

FIG. 53 is an explanatory view showing another third example of an embodiment.

FIGS. 54 and 55 relate to the 28th embodiment of the present invention.

FIG. 54 is an explanatory view showing the formation of an endoscope apparatus.

FIG. 55 is a sectioned view of an endoscope tip part.

DETAILED DESCRIPTION OF PREFERRED EMBODIMENT

Figure 1:
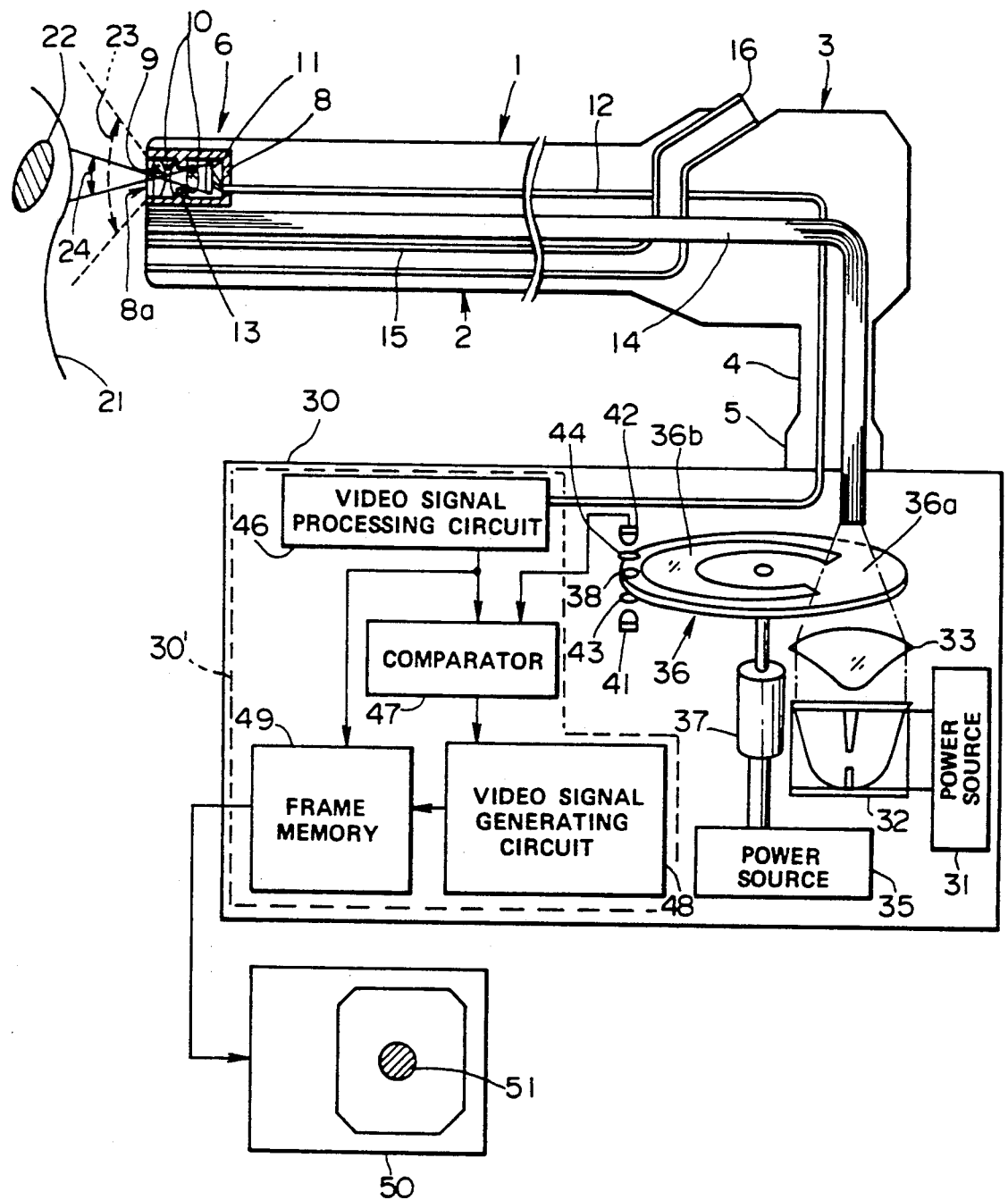
Figure 2:
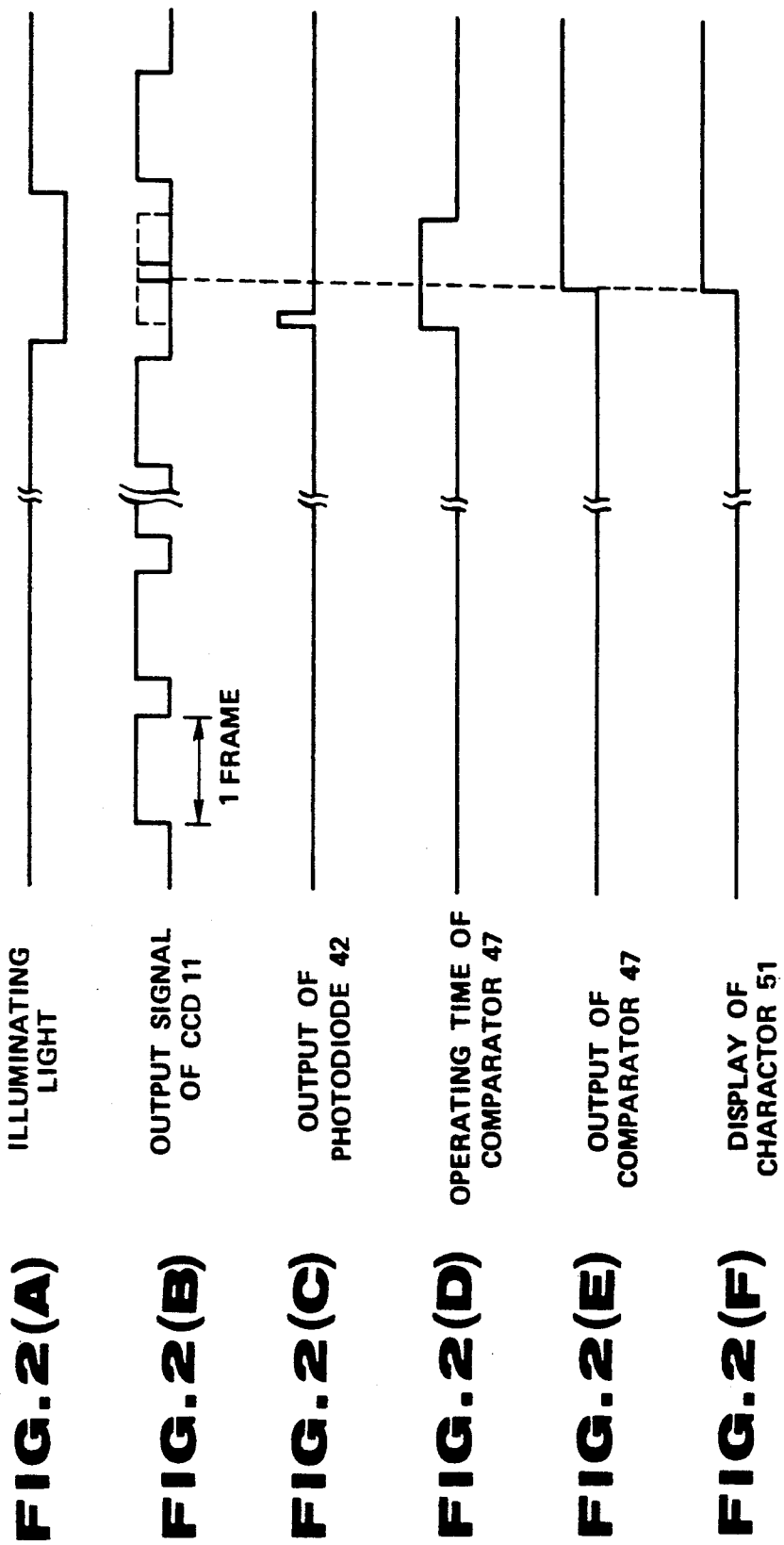

The first embodiment of the present invention is shown in FIGS. 1 and 2.

As shown in FIG. 1, an endoscope 1 is provided with an elongated, for example, flexible insertable part 2 and a thick operating part 3 connected to this insertable part 2 at the rear end. A flexible universal cord 4 is extended sidewise from the above mentioned operating part 3 and is provided at the tip with a connector 5 through which the above mentioned endoscope 1 is to be connected to a video processing apparatus 30.

A cylindrical collimator 8 made of a radioactive ray attenuating material and having an aperture 8a on the tip side is arranged in the tip part 6 of the above mentioned insertable part 2. The above mentioned aperture 8a of this collimator 8 is fitted with a cover glass 9. An objective lens system 10 is provided coaxially with the above mentioned cover glass 9 within the above mentioned collimator 8. A solid state imaging device (semiconductor imaging device), for example, a CCD 11 is arranged together with a peripheral circuit in the image forming position of this objective lens system 10. A color filter array (not illustrated) in which respective color transmitting filters of R (red), G (green) and B (blue) are arranged in the form of a mosaic or the like is provided on the front surface of the above mentioned CCD 11. A signal line 12 is connected to the above mentioned CCD 11, is inserted through the above mentioned insertable part 2 and universal cord 4 and is connected to the above mentioned connector 5. An iris part 13 made of a radioactive ray attenuating material is formed within the above mentioned collimator 8.

The radioactive ray attenuating material used for the above mentioned collimator 8 and iris part 13 is made of material which attenuates the intensity of radioactive rays for example, lead, tungsten, stainless steel, lead glass (made by mixing lead at a high ratio into plastics or epoxy resin), concrete, steel (the older, the better) or mercury.

A light guide 14 is inserted through the above mentioned insertable part 2, is arranged on the tip surface as directed in substantially the same direction as the visual field direction of the above mentioned objective lens system 10 on the tip surface of the above mentioned tip part 6, is inserted on the base side through the above mentioned universal cord 4 and is connected to the above mentioned connector 5. A treating tool channel 15 is formed within the above mentioned insertable part 2, is opened on the tip side on the tip surface of the above mentioned tip part 6 and is also opened on the base side on the side of the above mentioned operating part 3 to form an inserting port 16.

In the drawing, reference numeral 21 represents a body cavity inside wall, 22 represents a cancer, 23 represents an optical visual field and 24 represents a visual field of radioactive rays as, for example, γ rays.

On the other hand, the above mentioned video processing apparatus 30 is provided with a lamp 32 fed with an electric power by a power source 31. A condenser lens 33 is arranged in front of the above mentioned lamp 32 so that an illuminating light emitted out of the above mentioned lamp 32 will be condensed by the above mentioned condenser lens 33 and will enter the above mentioned light guide 14 at the entrance end. A rotary disc 36 rotatable with an axis parallel with the optical axis of the illuminating light as a center is arranged between the above mentioned condenser lens 33 and light guide 14 at the entrance end and is to be rotated and driven by a motor 37 fed with electric power by a power source 35. The above mentioned rotary disc 36 has a light intercepting part 36a formed in a part in the rotating direction and has a light transmitting part 36b in the other greater part. When the above mentioned rotary disc 36 is rotated by the above mentioned motor 37, the above mentioned light intercepting part 36a will be periodically interposed in the light path of the illuminating light from the above mentioned lamp 32 and the illuminating light will not be fed temporarily to the light guide 14. This rotary disc 36 is to be rotated at a number of revolutions that the above mentioned light intercepting part 36a may intercept the light, for example, by one frame at intervals of several frames.

A hole 38 is provided on the outer peripheral side of the above mentioned rotary disc 36. A luminous diode 41 and photodiode 42 are arranged as opposed to each other on both sides of the above mentioned hole 38 in the rotating position at the beginning of interposing the above mentioned light intercepting part 36a in the illuminating light path. Condenser lenses 43 and 44 are arranged respectively between the above mentioned luminous diode 41 and rotary disc 36 and between the above mentioned photodiode 42 and rotary disc 36 so that the light emitted from the above mentioned luminous diode 41 will be condensed by the condenser lens 43, will pass through the above mentioned hole 38, will be condensed by the condenser lens 44 and will enter the above mentioned photodiode 42. When the light enters the above mentioned photodiode 42, the position at the beginning of interposing the above mentioned light intercepting part 36a in the above mentioned light path will be able to be detected.

Also, a video signal processing circuit 46 is provided within the above mentioned video processing apparatus 30 and is connected with the signal line 12 connected to the above mentioned CCD 11. This video signal processing circuit 46 will drive the above mentioned CCD 11 and will process the output signal of the above mentioned CCD 11 so as to be a video signal.

The video signal produced by the above mentioned video signal processing circuit 46 will be stored in a frame memory 49 and then will be input into a CRT monitor 50 in which the object image will be displayed.

The output signal of the above mentioned video signal processing circuit 46 and the output of the above mentioned photodiode 42 will be input into a comparator 47 which will be operative only while the above mentioned light intercepting part 36a is interposed in the illuminating light path after the position of interposing the above mentioned light intercepting part 36a in the illuminating light path is detected by the output of the above mentioned photodiode 42. While the above mentioned comparator is operative, the output signal of the above mentioned video signal processing circuit 46 will be compared with a predetermined level. The output signal of this comparator 47 will be input into a video signal generating circuit 48 which will generate a predetermined character 51 in case a signal indicating that the output signal of the video signal processing circuit 46 is above the predetermined level is input from the above mentioned comparator and will deliver this character 51 to the above mentioned frame memory 49. The character 51 generated by the above mentioned picture image signal generating circuit 48 will be, for example, a circle showing the range of the above mentioned visual field 24 of γ rays. This character 51 will be displayed in the position corresponding to the above mentioned visual field 24 of γ rays on the displayed picture surface of the above mentioned CRT monitor 50.

In FIG. 1, the address designating circuit and others of the above mentioned frame memory 49 are omitted.

The operation of this embodiment shall be explained in the following with reference to FIG. 2.

In the case of inspecting a tumor, for example, a cancer using the endoscope 1 of this embodiment, at a predetermined time before the inspection, a cancer resistor marked with a radio-isotope or a deoxyglucose likely to concentrate on a cancer (high in the activity) will be injected into a body by venous injection or the like. Such a reagent will concentrate on the cancer 22 and radioactive rays, for example, γ rays will be emitted out of the cancer 22.

When the insertable part 2 of the above mentioned endoscope 1 is inserted into the body cavity and the lamp 32 within the video processing apparatus 30 is made to emit a light, the illuminating light emitted out of this lamp 32 will be condensed by the condenser lens 33, will pass through the rotary disc 36, will enter the light guide 14 of the endoscope 1 at the entrance end, will be led to the tip part 6 through this light guide 14 and will be emitted toward the object (body cavity inside wall 21) from the tip. As shown in FIG. 2(A), this illuminating light will be intercepted by one frame at intervals of several frames in response to the light intercepting part 36a of the above mentioned rotary disc 36.

When the above mentioned illuminating light is being radiated to the object, the light returning from the object by this illuminating light will pass through the cover glass 9 and will be made to form an image on the CCD 11 by the objective lens system 10. A output signal of the CCD 11 as is shown in FIG. 2 (B) will be input into the video signal processing circuit 46 within the video processing apparatus 30 through the signal line 12 and will be processed to be a video signal. In FIG. 2 (B), one ridge represents a signal by one frame.

The video signal produced by the above mentioned video signal processing circuit 46 will be stored in the frame memory 49 and then will be input into the CRT monitor 50 in which the object image will be displayed.

Now, when the tip part 6 of the above mentioned endoscope 1 is opposed to the cancer 22, the $\gamma$ rays emitted out of this cancer 22 will enter the collimator 8 made of a $\gamma$ ray attenuating material through the aperture 8a of the collimator 8 but not from the other directions. The iris part 13 of the above mentioned collimator 8 will act as a part of the collimator 8 to regulate the entering angle of the $\gamma$ rays. The $\gamma$ rays having thus entered the collimator 8 will reach CCD 11 and will hit a PN junction of the light receiving part of the CCD 11 to generate an electromotive force.

When the light intercepting part 36a of the above mentioned rotary disc 36 is interposed in the illuminating light path, the light will enter the photodiode 42 and this state will be sensed by the output of the above mentioned photodiode 42 being a high level. Only while the above mentioned light intercepting part 36a is interposed in the illuminating light path from then, the comparator 47 will be operative as shown in FIG. 2 (D). At this time, as shown in FIG. 2 (A), the illuminating light will not be radiated to the object but, at this time, if the $\gamma$ rays enter the above mentioned CCD 11, as shown in FIG. 2 (B), a signal corresponding to the above mentioned $\gamma$ rays will be output from the above mentioned CCD 11. The output signal from the above mentioned CCD 11 will be input into the above mentioned video signal processing circuit 46 through the signal line 12.

The signal by the $\gamma$ rays arranged in this video signal processing circuit 46 will be input into the frame memory 49 and also into the comparator 47. In this comparator 47, whether the $\gamma$ rays have entered the CCD 11 or not when the illuminating light is not radiated to the object will be determined by comparing the output signal of the above mentioned video signal processing circuit 46 with the predetermined level. That is to say, when the $\gamma$ rays enter the above mentioned CCD 11, as shown in FIG. 2 (B), the output of the above mentioned comparator 47 will be at a high level. The output of the comparator 47 will be input into the picture image signal generating circuit 48 in which, when the output of the above mentioned comparator 47 is at the high level, as shown in FIG. 2 (F), a predetermined character 51 will be generated and will be delivered to the frame memory 49. The character 51 generated by the above mentioned picture image signal generating circuit 48 will be a circle indicating, for example, the range of the visual field 24 of the above mentioned $\gamma$ rays and will be displayed in the position corresponding to the visual field 24 of the above mentioned $\gamma$ rays on the displaying picture surface of the above mentioned CRT monitor 50. Therefore, the $\gamma$ ray generating source, that is, the position of the cancer 22 can be known by this character 51. This character 51 may be displayed preferably by a unit, for example, of several frames to several seconds but the displaying time may be optional.

The position of the cancer 22 is displayed by the character 51 because the $\gamma$ rays can not be made to form an image by a lens or the like. Therefore, from whatever direction of the aperture angle of the collimator 8 the $\gamma$ rays may enter, the character 51 will be displayed and from what position within the aperture angle of the collimator 8 displayed by this character 51 the $\gamma$ rays are issued is not definite but it is apparent that the $\gamma$ rays are issued from either position of the above mentioned aperture angle of the collimator 8.

In this embodiment, only when the illuminating light is temporarily intercepted and is not radiated, that is, only when there is no light information from the object, whether the $\gamma$ rays are being issued or not will be detected, because, if a light is incident, the signal by the feeble $\gamma$ rays from the CCD 11 which is not inherently a $\gamma$ ray sensing detector will be buried by the signal by the incident light and will be difficult to discriminate.

Thus, according to this embodiment, as superimposed on the endoscope image, the direction and position of the $\gamma$ ray generating source can be confirmed simultaneously and easily and the endoscope image and the $\gamma$ ray generating source can be easily made to correspond to each other. Therefore, the presence and position of a deep part cancer or lymphatic knob transfer can be easily confirmed and the operating and curing methods can be determined easily and positively.

In the case of a cancer accompanied an ulcer, in order to determine whether only the ulcer is present or only the cancer, a biopsy has been necessary but, when the endoscope apparatus of this embodiment is used, the biopsy will not be necessary and the diagnosing speed will improve.

By detecting $\gamma$ rays and processing thereof with a radioactive ray signal processing means 30', even the presence of a minute cancer difficult to discover by the endoscope diagnosis can be confirmed, the cancer diagnosing activity can be improved and a cancer can be discovered even by a doctor having little experience.

Figure 3:
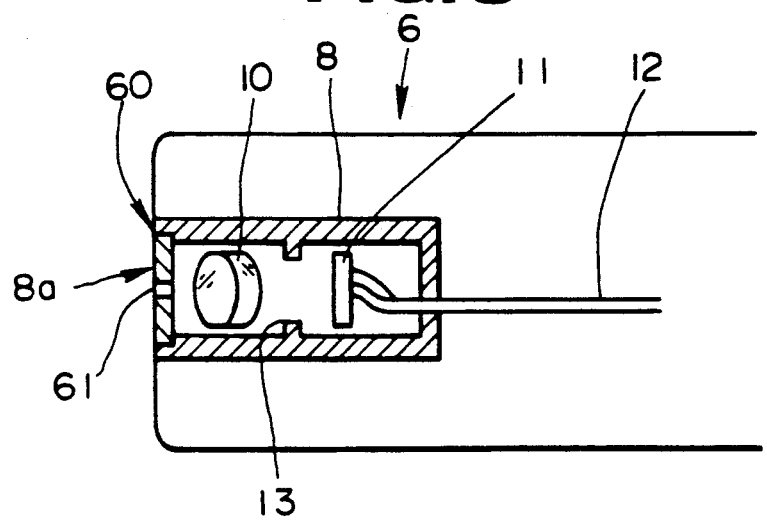
FIG. 3 is an explanatory view of a tip part of an endoscope.
Figure 4:
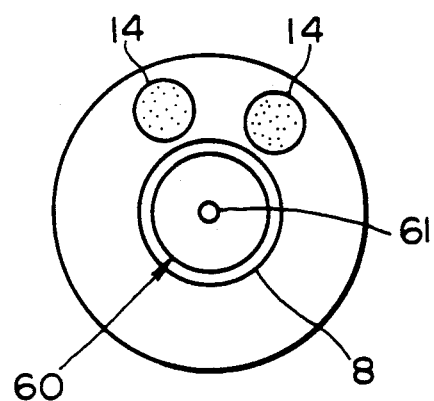
FIG. 4 is an elevation of the tip part of the endoscope.

The second embodiment of the present invention is shown in FIGS. 3 and 4.

In this embodiment, as shown in FIG. 3, a cover glass 60 is fitted to the aperture 8a of the collimator 8. In this cover glass 60, as shown in FIG. 4, only the central part is a $\gamma$ ray transmitting part 61 transmitting $\gamma$ rays but the other part contains, for example, lead and transmits light but does not transmit $\gamma$ rays.

The entering angle of $\gamma$ rays determined by the size of the $\gamma$ ray transmitting part 61 of the above mentioned cover glass 60 is smaller than the entering angle of $\gamma$ rays in the first embodiment. Therefore the size of the character 51 displayed in the CRT monitor 50 is made small corresponding to the visual field range of $\gamma$ rays.

The other formations are the same as in the first embodiment.

According this embodiment, the visual field of $\gamma$ rays is so small that the $\gamma$ ray generating source, that is, the position of the cancer 22 can be more accurately known.

The other operations and effects are the same as in the first embodiment.

In the first and second embodiments, the color imaging system is not limited to be of the simultaneous type provided with a color filter array on the front surface of the CCD 11 but may be of a field sequential type switching the illuminating light sequentially to R, G, B and the like. In case this field sequential type is used, a rotary filter having such respective color filters as R, G, B and the like arranged in the peripheral direction may be provided separately from the rotary disc 36. This rotary filter may be provided with a light intercepting part to detect γ rays.

Figure 5:
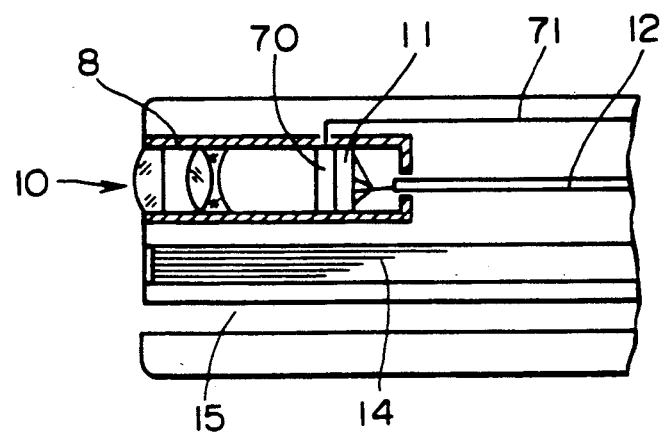
FIG. 5 is an explanatory view of a tip part of an endoscope in the third embodiment of the present invention.

The third embodiment of the present invention is shown in FIG. 5.

In this embodiment, a light intercepting shutter made, for example, of a liquid crystal plate 70 is provided on the front surface side of the CCD 11. A lead wire 71 is connected to this liquid crystal plate 70, is inserted through the insertable part 2 and universal card 4 and is to be connected to a driving circuit (not illustrated) provided within the video processing apparatus 30. When electricity is passed through the lead wire 71 from this driving circuit to apply a voltage to the liquid crystal plate 70, this crystal plate 70 will be colored to be able to intercept the light.

In this embodiment, since the above mentioned liquid crystal plate 70 is provided, the rotary disc 36 in the first embodiment will be unnecessary. While the liquid crystal plate 70 is being driven by the above mentioned driving circuit to intercept the light, the output signal of the video signal processing circuit 46 will be compared with a predetermined level by a comparator 47.

The other formations, operations and effects are the same as in the first embodiment.

As explained above, according to the first to third embodiments, the endoscope image and radioactive information can be simultaneously seen and the endoscope image and radioactive ray generating source can be easily made to correspond to each other.

Also, as one solid state imaging device is used for both of the imaging means and radioactive ray detecting means, the tip part will not be made larger than of a general electronic endoscope.

Since the collimator, made of a radioactive ray attenuating material and having at least one aperture in the visual field direction, is provided on the periphery of the above mentioned solid state imaging device, there is an effect that the position of the radioactive ray generating source can be easily confirmed.

Figure 6:
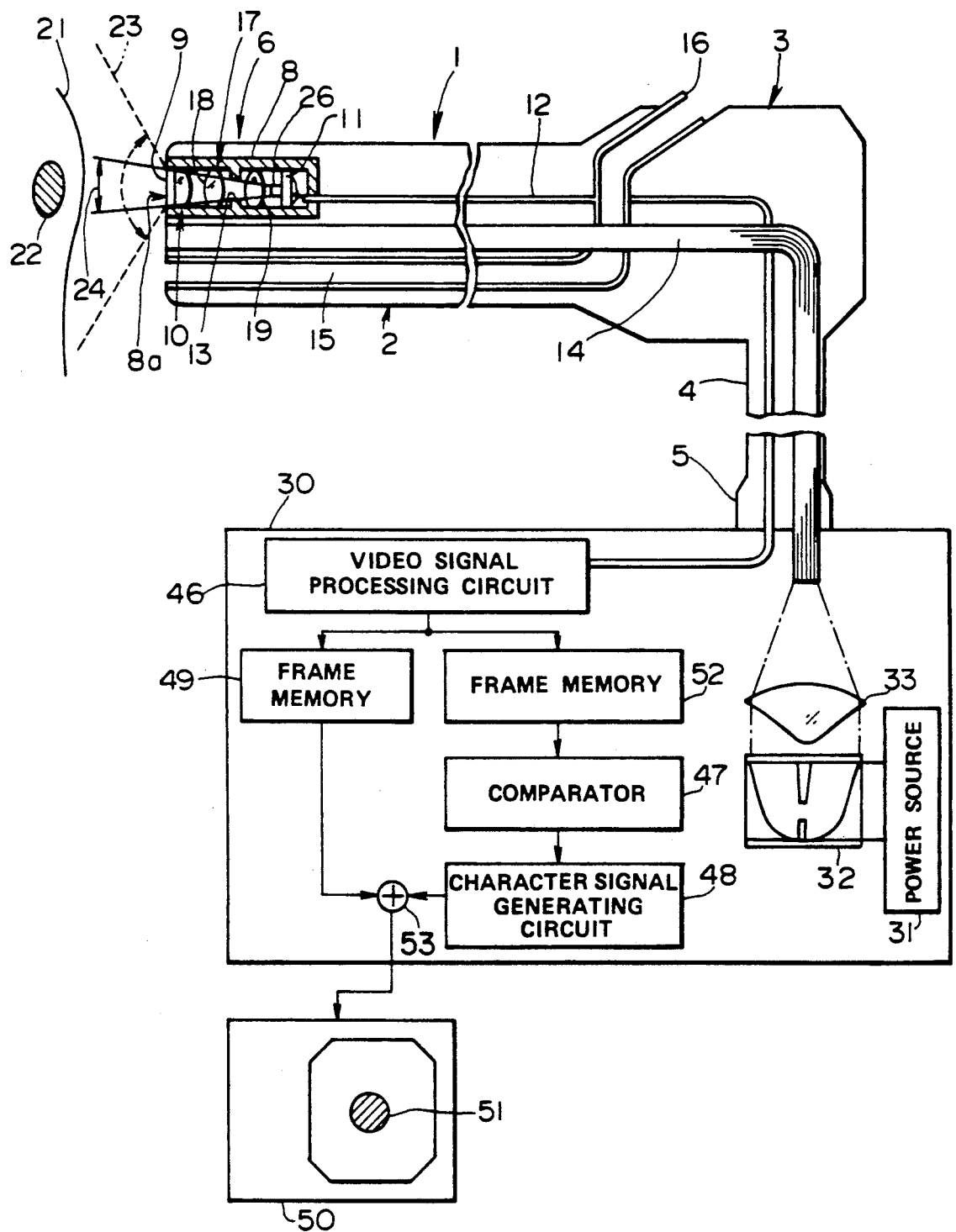
FIG. 6 is an explanatory view showing the formation of an endoscope apparatus in the fourth embodiment of the present invention.

The fourth embodiment of the present invention is shown in FIG. 6.

In the endoscope 1 of this embodiment, the objective lens system 10 is provided coaxially with the cover glass 9 within the collimator 8 and a first lens 18 and second lens 19 forming a relay lens system 17 as an image transmitting optical system are arranged inside this objective lens system 10. Further, an iris part 13 made of a radioactive ray attenuating material is formed between the first lens 18 and second lens 19 within the collimator 8.

An image formed by the above mentioned objective lens system 10 will be transmitted sequentially rearward by the first lens 18 and second lens 19 forming the relay lens system 17, will be diaphragmed by the iris part 13 and will be formed on the imaging surface of the CCD 11. A color filter array (not illustrated) in which respective color transmitting filters of R (red), G (green), B (blue), etc. are arranged in the form of a mosaic is provided on the above mentioned imaging surface of the CCD 11.

A light intercepting plate 26 intercepting the light but transmitting only radioactive rays is pasted to the central part of the above mentioned imaging surface of the CCD 11 and is of an outside diameter of such size as covers all the part which can be reached by the radioactive rays passing through the aperture 8a and iris part 13 and entering at the visual field angle 24 of the radioactive rays. That is to say, in the part covered with the light intercepting plate 26 of the imaging surface of the CCD, the radioactive rays in the part of the visual field angle 24 of the radioactive rays will be detected and, in the part not covered, the part of the optical visual field 23 will be imaged as an object image.

By the above mentioned relay lens system 17, the visual field angle 24 of the radioactive rays will be regulated by enlarging as much as possible the distance between the aperture 8a and CCD 11.

On the other hand, the above mentioned video processing apparatus 30 is provided with a lamp 32 fed with electric power by a power source 31. A condenser lens 33 is arranged in front of the above mentioned lamp 32 so that the illuminating light emitted from the above mentioned lamp 32 will be condensed by the above mentioned condenser lens 33 and will enter a light guide 14 at the entrance end.

Within the above mentioned video processing apparatus 30, a video signal processing circuit 46 is provided and is connected with the signal line 12 connected to the above mentioned CCD 11. This video signal processing circuit 46 will drive the above mentioned CCD 11 and will process the output signal of the above mentioned CCD 11 so as to be a video signal.

The video signal produced by the above mentioned video signal processing circuit 46 will be branched. One side of the video signal will be stored in a frame memory 49 and then will be input into a CRT monitor 50 through an adding circuit 53 and an object image will be displayed in this CRT monitor 50.

The other side of the output signal of the above mentioned video signal processing circuit 46 will be stored in a frame memory 52. A signal corresponding to the part covered with the light intercepting plate 26 of the CCD 11, that is, a signal relating to radioactive rays will be read out of this memory 52, will be input into a comparator 47 and will be compared therein with a predetermined level. The output signal of this comparator 47 will be input into a character signal generating circuit 48 in which, in case a signal indicating that the output signal of the video signal processing circuit 46 is above a predetermined level is input, a predetermined character 51 will be generated, will be delivered to the above mentioned adding circuit 53, will be a circle showing, for example, the range including a cancer 22 of the visual field 24 of the above mentioned radioactive rays and will be displayed in the position corresponding to the visual field 24 of the radioactive rays on the displayed picture surface of the above mentioned CRT monitor 50.

The other formations are the same as in the first embodiment.

The operation of this embodiment shall be explained in the following.

In the case of inspecting a cancer by using the endoscope 1 of this embodiment, the same as in the case of the first embodiment, at a predetermined time before the inspection, a cancer resistor marked with a radioisotope or a deoxyglucose likely to concentrate on a cancer will be injected into the body by venous injection or the like. Such a reagent will concentrate on the cancer 22 and radioactive rays, for example, γ rays will be emitted out of the cancer 22.

When the insertable part 2 of the above mentioned endoscope 1 is inserted into the body cavity and the lamp 32 within the video processing apparatus 30 is made to emit light, the illuminating light emitted out of this lamp 32 will be condensed by the condenser lens 33, will enter the light guide 14 at the entrance end, will be led to the tip part 6 through this light guide 14 and will be emitted toward the object (body cavity inside wall 21) from the exit end surface.

When the above mentioned illuminating light is being radiated to the object, the light returning from the object by this illuminating light will pass through the cover glass 9, objective lens system 10, relay lens system 17 and iris part 13 and will be made to form an image on the other part than the part covered with the light intercepting plate 26 on the CCD 11. The output signal of the CCD 11 will be input into the video signal processing circuit 46 within the video processing apparatus 30 through the signal line 12 and will be processed to be a video signal.

The video signal produced by the above mentioned video signal processing circuit 46 will be stored in the frame memory 49 and then will be input into the CRT monitor 50 in which the object image will be displayed.

Now, when the radioactive ray generating source, that is, the cancer 22 is located within the visual field angle 24 of the radioactive rays, the radioactive rays emitted out of this cancer 22 will enter the collimator 8 at the visual field angle 24 of the radioactive rays through the aperture 8a of the collimator 8 made of radioactive ray attenuating material such as lead and the iris part 13 but not from the other directions. The radioactive rays having thus entered the collimator 8 will pass through the light intercepting plate 26, will reach the CCD 11, will hit a PN junction of the light receiving part of the CCD 11 to generate an electromotive force and will output a signal corresponding to the radioactive rays. This output signal having the signal relating to the picture image of the CCD 11 and the signal relating to the radioactive rays will be input into the above mentioned video signal processing circuit 46 through the signal line 12. This output signal will be arranged by the video signal processing circuit 46 and the digitalized output signal will be stored in the frame memories 49 and 52. The signal stored in the frame memory 52 will have only the address corresponding to the part covered with the light intercepting plate 26 read out and will be input into the comparator 47. This comparator 47 will compare the read out signal with a predetermined level and will thereby exclude the influence of the background. That is to say, when the radioactive rays enter the CCD 11, the output of the comparator 47 will be at a high level. The output of this comparator 47 will be input into the character signal generating circuit 48 which will generate a predetermined character 51 when the output of the above mentioned comparator 47 is at a high level and will deliver it to the adder 53. The character 51 generated by the character signal generating circuit 48 will be a circle showing, for example, a range of the above mentioned visual field 24 of the radioactive rays and will be displayed in the position corresponding to the above mentioned visual field 24 of the radioactive rays. Therefore, it can be sensed by this character 15 that the cancer 22 is at least within the visual field angle 24 of the radioactive rays.

Also, in this embodiment, the light will be intercepted on a part of the imaging surface of the CCD 11 by the light intercepting plate 26 and the radioactive rays will be detected in this part, because, if the light enters, the signal by the feeble radioactive rays from the CCD which is not inherently a radioactive ray sensing detector will be buried by the signal by the entering light and will be difficult to discriminate.

As mentioned above, according to this embodiment, as the relay lens system 17 is arranged between the aperture 8a and CCD 11, the CCD 11 can be positioned rearward of the aperture 8a and further, as the iris part 13 is provided, a wide optical visual field can be secured and the visual field angle 24 of the radioactive rays can be narrowed. Therefore, the radioactive ray emitting source can be accurately displayed by the character 51.

Further, since the part which is exclusively for detecting radioactive rays, is provided on the imaging surface of the CCD 11, the character 51 showing the radioactive ray generating source can be indicated in real time on the endoscope image and the direction and position of the radioactive ray generating source can be easily confirmed. Therefore, the presence and position of a deep part cancer or lymphatic knob transfer can be easily confirmed can the operating method and curing method can be determined easily and positively.

Self convergent optical fibers (trade name of SELFOC LENS) may be used instead of the relay lens system for the image transmitting optical system.

The other operations and effects are the same as in the first embodiment.

Even in the third and fourth embodiments, the color imaging system may be not only of the simultaneous type provided with a color filter array on the front surface of the CCD 11 but also of a field sequential type in which the illuminating light is switched sequentially to R, G, B, etc.

However, as in the above mentioned respective embodiment, in case the observing solid state imaging device itself is made a radioactive ray detecting means, there will be defects that, even in the case of an ordinary observation, radioactive rays will be detected and bright points will appear on the monitor picture surface which will become difficult to see.

Therefore, examples of a radioactive ray detecting endoscope in which the influence of radioactive rays can be reduced at the time of an ordinary observation are shown in the fifth to tenth embodiments.

The fifth embodiment of the present invention is shown in FIGS. 7 and 8.

As shown in FIG. 7, in a radioactive ray detecting endoscope 81 in this embodiment, a collimator 8 made of a radioactive ray attenuating material is arranged in the tip part 6 of the insertable part 2, an objective lens system 10 is provided in front of this collimator 8 and a CCD 11 is arranged in the image forming position of this objective lens system 10 together with the peripheral circuit. A color filter array, in which respective color transmitting filters of R (red), G (green), B (blue), etc. are arranged in the form of a mosaic, is provided on the front surface of the above mentioned CCD 11. A signal line 12 is connected to the above mentioned CCD 11, is inserted through the above mentioned insertable part 2 and universal cord 4 and is connected to the above mentioned connector 5.

A filter 83 made of such radioactive ray attenuating and optically transparent material as such lead glass as, for example, a transparent lead-containing acryl resin plate KYOWA GLASS-XA (trade name, Kyowa Glass Chemical Industrial Company, Ltd.) or a radioactive ray shielding lead glass LX-57B (trade name, Japan Electric Glass Company, Ltd.) is held by a filter frame 84 which is provided rotatably with a supporting part 85 as a fulcrum. In energizing member as a spring (not illustrated) is provided in the supporting part 85 and is to position the filter 83 upward so as not to intercept the light entering the CCD 11 as in FIG. 7. An operating wire 86 is connected to the filter frame 84 at the end, is inserted through a supporting pipe 87, is led to the operating part 3, rotates the filter 83 and filter frame 84 against the above mentioned energizing member remotely from the operating part by being pulled and can shield the CCD 11.

On the other hand, the video processing apparatus 30 is provided with a lamp 32 fed with electric power by a power source 31. A condenser lens 33 is arranged in front of the above mentioned lamp 32 so that the illuminating light emitted from the above mentioned lamp 32 will be condensed by the above mentioned condenser lens 33 and will enter a light guide 14 at the entrance end.

A video signal processing circuit 91 is provided within the above mentioned video processing apparatus 30 and the signal line 12 connected to the above mentioned CCD 11 is to be connected to the above mentioned video signal processing circuit 91 which will drive the above mentioned CCD 11 and will process the output signal of the above mentioned CCD 11 so as to be a video signal. The processed video signal will be output to a monitor 50 and the object image will be displayed on a picture surface.

The other formations are the same as in the first embodiment.

The operation of the radioactive ray detecting endoscope 81 formed as in the above shall be explained.

In the case of inspecting a cancer by using the endoscope 81 of this embodiment, the same as in the case of the first embodiment, at a predetermined time before the inspection, a cancer resistor marked with a radioisotope or a deoxyglucose likely to concentrate on a cancer will be injected into the body by venous injection or the like. Such a reagent will concentrate on the cancer and radioactive rays, for example, $\gamma$ rays will be emitted out of the cancer 22. When the insertable part 2 of the endoscope 81 is inserted into the body cavity and the video processing apparatus 30 is operated, the illuminating light by the lamp 32 within the video processing apparatus 30 will be condensed by the condenser lens 33 will be radiated into the light guide 14 at the entrance end, will be led to the tip part 6 through the light guide 14 and will illuminate the body cavity inside wall 21 from the tip part.

On the other hand, the reflected light from the body cavity inside wall 21 will be made to form an image on the CCD 11 by the objective lens system 10. The object image will be photoelectrically converted to be an electric signal by the CCD 11, the electric signal will be input into the video signal processing circuit 91 within the video processing apparatus 30 through the signal line 12 and will be processed to be a video signal by the video processing circuit 91 and the object image will be displayed on the picture surface of the CRT monitor 50.

In the state of FIG. 7, as the above mentioned filter 83 will be retracted upward by an energizing member (not illustrated) so as not to intercept the CCD 11, when the tip part 6 of the above mentioned endoscope 81 is opposed to the cancer 22, the $\gamma$ rays emitted from this cancer 22 will enter through the aperture of the collimator 8 made of $\gamma$ ray attenuating material such as lead. The $\gamma$ rays from the other direction will not enter the CCD. The $\gamma$ rays having entered will reach the CCD 11, will hit the PN junction of the light receiving part of the CCD 11 and will generate an electromotive force. The generated electromotive force will be processed by the video signal processing circuit 91, the video signal will be displayed as bright points on the picture surface of the CRT monitor 50, the presence of the $\gamma$ rays will be confirmed and the presence of the cancer tissue within the visual field will be thereby diagnosed.

On the other hand, after the presence of the cancer 22 is diagnosed as mentioned above, it is necessary to further make a minute morphological diagnosis. In this case, the bright points by the $\gamma$ rays will obstruct the observation. Therefore, as shown in FIG. 8, by pulling the operating wire 86 of the operating part 3, the filter 83 attenuating radioactive rays will be inserted in the optical axis between the objective lens system 10 and CCD 11, the $\gamma$ rays will not substantially enter the CCD 11 and a picture image which is not unusual will be obtained.

As mentioned above, according to this embodiment, by retreating or projecting with the operating wire 86 the filter 83, which can attenuate and shield the radioactive rays, and can transmit visible rays, the radioactive rays can be detected and an ordinary observation can be made.

The sixth embodiment of the present invention is shown in FIG. 9.

In this embodiment, the CCD 11 is arranged within a collimator 8 made of such radioactive ray attenuating material such as lead. A housing chamber 96 which is the collimator 8 and houses a filter 83 fixed to a filter frame 84 in front of the CCD, is provided. A coil spring 97 formed of a form memorizing alloy is housed within the housing chamber 96 and is fixed at one end to the collimator 8 and at the other end to the lower part of the filter frame 84. This coil spring 97 is stored in the contracted form so as to contract when the temperature rises.

A coil spring 98 fixed to the collimator 8 is connected to the filter frame 84 in the upper part. The coil spring 97 formed of the form memorizing alloy and the coil spring 98 are electrically connected with each other through a lead wire (not illustrated) and are further connected to a driving power source 99 so as to be able to be electrified by operating a switch (not illustrated) to be on and off.

The other formations are the same as in the fifth embodiment.

The operation of the radioactive ray detecting endoscope formed as mentioned above shall be explained.

In the case of detecting radioactive rays, the coil springs 97 and 98 will be electrified by operating the switch (not illustrated) of the driving power source 99 to be on. When the coil spring 97 is electrified, the temperature will rise. When the transforming point is exceeded, the coil spring 97 will tend to be in the stored contracted state. The contracting force at this time will be so much larger than the tensile force of the coil spring 98 as to retreat the filter 83 into the housing chamber 96. Thereby, γ rays will enter the CCD 11 and the presence of a cancer tissue will be able to be diagnosed.

On the other hand, at the time of an ordinary observation, the electrification of the coil spring 97 will be stopped by operating the switch (not illustrated) of the driving power source 99 to be off. The coil spring 97 will be cooled to eliminate the contracting force and will be extended by the tensile strength of the coil spring 98 and the filter 83 will project on the front surface of the CCD 11 to shield the entering γ rays.

The other operations and effects are the same as in the fifth embodiment.

According to such a formation as is mentioned above, with a simple formation, the presence of the minute cancer 22 or the cancer 22 below the mucous membrane can be confirmed, the filter 83 made of an optically transparent material attenuating radioactive rays can be inserted between the CCD 11 and objective lens system 10 as required and therefore a picture image not disturbed by noises even in the ordinary observation in the presence of γ rays can be obtained.

The seventh embodiment of the present invention is shown in FIG. 10.

In this embodiment, a lens 93 made of an optically transparent material attenuating radioactive rays is provided in place of the filter 83 in the fifth embodiment and a lens frame 94 is provided in place of the filter frame 84. The above mentioned lens 93 forms a part of the objective lens system 10.

The other formations are the same as in the fifth embodiment.

In this embodiment, at the time of the ordinary observation, by inserting the lens 93 in the optical axis of the objective lens system 10, a picture image having no influence of γ rays will be able to be obtained.

On the other hand, at the time of detecting radioactive rays, by retreating the lens 93 from the optical axis of the objective lens system 10, γ rays will enter to be able to be detected. At this time of detecting radioactive rays, out of focus image will be out-focused.

The other operations and effects are the same as in the fifth embodiment.

The formation of inserting and removing the filter and lens is not limited to the above mentioned respective embodiments but an attraction, for example, of a magnet may be utilized.

Also, in the fifth to seventh embodiments, the color imaging system is not limited to be of the simultaneous type in which a color filter array is provided on the front surface of the CCD 11 but may be of a field sequential type in which the illuminating light is switched sequentially to R, G, B, etc.

As explained above, according to the fifth to seventh embodiment, there are effects that, with a simple formation, a picture image enabling to detect radioactive rays and an ordinary picture image not influenced by radioactive rays can be obtained and an accurate diagnosis can be made.

The eighth embodiment of the present invention is shown in FIGS. 11 to 15.

As shown in FIG. 13, an endoscope 101 is provided with an elongated, for example, flexible insertable part 102 and a thick operating part 103 connected to this insertable part 102 at the rear end. A flexible universal cord 104 is extended sidewise from the above mentioned operating part 103 and is provided at the end with a connector 106 to be removably connected to a processing apparatus 105.

A tip part 110 of the above mentioned insertable 102 is provided with an observing window, illuminating window and treating tool channel opening. A tubular collimator 111 made of a radioactive ray attenuating material as lead is fitted to the inside of the above mentioned observing window and an objective lens system 112 is fitted within this collimator 111. A solid state imaging device as, for example, a CCD 115 is arranged in the image forming position of the above mentioned objective lens system 112 in the inner part of the above mentioned collimator 111. A filter member 120 is provided on the front surface of this CCD 115.

In this embodiment, the color imaging system is of a simultaneous type and, as shown in FIG. 11, the above mentioned CCD 115 has respective video pixels 116R, 116G and 116B (represented by the reference numeral 116) corresponding to R (red), G (green) and B (blue) and radioactive ray detecting pixels 117 provided in a predetermined arrangement between the above mentioned video pixels 116. The above mentioned CCD 115 corresponds to an interline transfer system. Transferring parts 118 are provided in stripes between respective pixels in the horizontal direction.

The above mentioned filter member 120 is formed as shown in FIG. 12. That is to say, a color filter 121 is provided in the position corresponding to the video pixel 116 of the above mentioned CCD 115 and is an R transmitting filter on the front surface of the video pixel 116R, G transmitting filter on the front surface of the video pixel 116G and B transmitting filter on the front surface of the video pixel 116B. A light transmitting and radioactive ray attenuating filter 122 is provided as a radioactive ray attenuating means on the front surface of the above mentioned color filter 121 so that a visible light will reach the video pixel 116 but radioactive rays will not reach it. A light intercepting filter 123 transmitting radioactive rays but not transmitting a visible light is provided on the front surface of the above mentioned radioactive ray detecting pixel 117. An intercepting part 124 intercepting a light and radioactive rays is provided on the front surface of the above mentioned transferring part 118. The material of the above mentioned radioactive ray attenuating filter 122 may be the same as, for example, of the filter 83 in the fifth embodiment. Signal lines 126 are connected to the above mentioned CCD 115, are inserted through the insertable part 102, operating part 103 and universal cord 104 and are connected to the connector 106.

A light distributing lens 131 is arranged inside the illuminating window of the above mentioned tip part 110 and a light guide 132 is provided on the rear end side of this light distributing lens 131, is inserted through the insertable part 102, operating part 103 and universal cord 104 and is connected at the entrance end to the connector 106.

A treating tool channel 135 is formed within the above mentioned insertable part 102 and is opened on the tip side in a treating tool channel opening in the above mentioned tip part 110 and on the base end side on the side of the operating part 103 to form an inserting port 136.

On the other hand, the above mentioned processing apparatus 105 is provided with a lamp 141 emitting an illuminating light so that the illuminating light emitted from this lamp 141 will enter the above mentioned light guide 132 at the entrance end and with a driver 142 and separating circuit 143 connected to the above mentioned CCD 115 through the above mentioned signal lines 126 and connector 106 so that the above mentioned CCD 115 will be driven by the above mentioned driver 142 and the pixel signals read out of this CCD 115 will be input into the above mentioned separating circuit 143 and will be separated by this separating circuit 143 into signals from the video pixels 116 and signals from radioactive ray detecting pixels 117 which will be input respectively into a video signal processing circuit 144 and radioactive ray processing circuit 145. The above mentioned video signal processing circuit 144 will process the signals from the video pixels 116 and will output them as video signals. The above mentioned radioactive ray signal processing circuit 145 will process the signals from the radioactive ray detecting pixels 117 to produce radioactive ray information as the radioactive ray intensity. The respective output signals of the above mentioned video signal processing circuit 144 and radioactive ray signal processing circuit will be input and synthesized in a superimposing circuit 146 and the output signal of this superimposing circuit 146 will be input into a monitor 150 in which the object image imaged by the video pixels 116 and the information of the radioactive rays detected by the radioactive ray detecting pixels will be displayed. As a displaying manner in the above mentioned monitor 150, for example, as shown in FIG. 14 (A), the radioactive ray intensity 151 or the like may be displayed on the side of the object image, as shown in FIG. 14 (B), the object image may be displayed on a parent picture surface 152 and the bright points by radioactive rays may be displayed on a small picture surface, as shown in FIG. 14 (C), the bright points by radioactive rays may be displayed as superimposed on the object image as required and, in the case of an ordinary observation, the object image may be displayed with the above mentioned bright points extinguished.

The operation of this embodiment shall be explained in the following.

In the case of inspection a cancer by using the endoscope 101 of this embodiment, at a predetermined time before the inspection, a cancer resistor marked with a radio-isotope or a deoxyglucose likely to concentrate on a cancer will be injected into the body by venous injection or the like. Such a reagent will concentrate on the cancer and radioactive rays, for example, γ rays will be emitted out of the cancer.

When the insertable part 102 of the above mentioned endoscope 101 is inserted into the body cavity and the lamp 141 within the processing apparatus 105 is made to emit a light, the illuminating light emitted from this lamp 141 will enter the light guide 132 of the endoscope 101 at the entrance end, will be led to the tip part 110 through the light guide 132 and will be radiated to an object through the light distributing lens 131.

The optical image of this object will be formed on the CCD 115 by the objective lens system 112. In such a case, the visible light will pass through the radioactive ray intercepting filter 122 of the filter member 120, will be separated in colors by the color filter 121 and will reach the video pixels 116. Also, this visible light will be intercepted by the light intercepting filter 123 and intercepting part 123 and will not reach the radioactive ray detecting pixel 117 and transferring part 118.

When the tip part 110 of the above mentioned endoscope 101 is opposed to a cancer, the γ rays emitted from this cancer will enter the collimator 111 through the aperture of this collimator 111 and will be prevented by the radioactive ray attenuating filter 122 and intercepting part 124 from reaching the video pixel 116 and transferring part but will pass through the light intercepting filter 123, will reach only the radioactive ray detecting pixel 117 and will hit a PN junction of the radioactive ray detecting pixel 117 to produce a signal and γ rays will be detected.

The above mentioned CCD 115 will be driven by the driver 142 within the control apparatus 105 and pixel signals of the video pixels 116 and pixel signals of the radioactive ray detecting pixels 117 will be read out. Both pixel signals will be separated by the separating circuit 143, the signals from the video pixels 16 will be processed by the video signal processing circuit 144 and the signals from the radioactive ray detecting pixels 117 will be processed by the radioactive ray signal processing circuit 145. The output signals of the above mentioned respective signal processing circuits 144 and 145 will be synthesized by the superimposing circuit 146 and will be input into the monitor 150 in which the object image imaged by the video pixels 116 and the information of the radioactive rays detected by the radioactive ray detecting pixels 117 will be displayed.

Thus, according to this embodiment, as the CCD 115 is provided with the video pixels 116 and radioactive ray detecting pixels 117 and the radioactive ray attenuating filter 122 is provided on the front surface of the video pixel 116, no bright point by radioactive rays will appear in the observed picture image in the endoscope 101 and a picture image which is easy to see will be obtained. Further, the observation and radioactive ray detection can be made simultaneously.

The observed image by the endoscope and the radioactive ray information may not be displayed on the same monitor, for example, as shown in FIG. 15, the output signal of the video signal processing circuit 144 may be input into the monitor 150 and the output signal of the radioactive ray signal processing circuit 145 may be input into a displaying apparatus 155 by which the radioactive ray information may be displayed.

The ninth embodiment of the present invention is shown in FIGS. 16 and 17.

In this embodiment, as shown in FIG. 16, for example, rectangular radioactive ray detecting pixels 162 are provided in four corners of the light receiving surface of a CCD 160 and the other part is made a video pixel 161. A tubular collimator 163 of a rectangular cross-section is provided on the front surface side of each of the above mentioned radioactive ray detecting parts 162. Though not illustrated, a light transmitting and radioactive ray intercepting filter is provided on the front surface of the above mentioned video pixel 161 and a radioactive ray transmitting and light intercepting filter is provided on the front surface of each of the radioactive ray detecting pixels 162.

In this embodiment, the collimator 111 in the eighth embodiment is not required.

The control apparatus 105 may be the some as is shown in FIGS. 13 and 15 or may be formed as shown in FIG. 17. In the control apparatus 105 shown in FIG. 17, the signals from the video pixels 161 and the signals from the radioactive ray detecting pixels 162 will be both processed to be video signals by a signal processing circuit 165 and will be output to the monitor 150 in which an observed picture image 166 marked to be octagonal or circular will be displayed in the central part of the picture surface and radioactive ray information 167 will be displayed as a brightness corresponding, for example, to the intensity in the four corner parts outside this observed picture image 166.

Thus, according to this embodiment, in case the observed picture image by the endoscope is displayed as masked to be octagonal or circular, the radioactive ray information will be able to be obtained and displayed without influencing this observed picture image at all.

The displaying manner in the monitor 150 may be as shown in FIGS. 14 (A) to (C).

The other formations, operations and effects are the same as in the eighth embodiment.

In the eighth and ninth embodiments, the color imaging system may be of a field sequential type of switching the illuminating light sequentially to R, G, B, etc. In this case, no color filter will be required on the front surface of each video pixel 116.

The solid state imaging device is not limited to be the CCD but may be a MOS, BBD, etc. capable of detecting radioactive rays.

As explained above, according to the eighth and ninth embodiments, as the video pixels and radioactive ray detecting pixels are provided in all the pixels of the solid state imaging device and the video pixels are provided with the radioactive ray attenuating means, there is an effect that the observation and radioactive ray detection can be simultaneously made without adversely affecting the observed picture image.

The tenth embodiment of the present invention is shown in FIGS. 18 and 19.

As shown in FIG. 18, an endoscope 171 in this embodiment is of substantially the same formation as of the endoscope 101 shown in FIG. 13 but is provided with the ordinary CCD 11 used in the first embodiment and others instead of the CCD 115 having the video pixels 116 and radioactive ray detecting pixels 117.

On the other hand, a processing apparatus 105 is provided with a lamp 141 emitting an illuminating light so that the illuminating light emitted out of this lamp 141 may enter a light guide 132 at the entrance end and with a driving part 172 and comparator, 173 connected to the above mentioned CCD 11 through signal lines 126 and a connector 106 so that the above mentioned CCD 11 will be driven by the above mentioned driving part 172 and the pixel signal read out of this CCD 11 will be input into the above mentioned comparator 173, will pass through the comparator 173, will be A/D converted by an A/D converter 174 and will be input into a memory 175.

The above mentioned comparator 173 ca be switched to be set at an ordinary observing mode and radioactive ray detecting mode. In the ordinary observing mode, the above mentioned comparator 173 will compare respective input pixel signals with a reference value, the signal below the reference value will be stored as it is in a predetermined address of a memory 175 and the signal exceeding the reference value will have the same value as of the signal immediately before it stored in a predetermined address of the memory 175. In case two or more pixel signals exceed the reference value and the signal immediately before them also exceeds the reference value, the value of the signal below the reference value of the pixel further before them will be stored in the memory 175. This can be realized, for example, by providing a storage means holding the signal below the newest reference value to output the signal below the newest reference value stored in the above mentioned storage means instead of the signal exceeding the reference value. On the other hand, in the radioactive ray detecting mode, the above mentioned comparator 173 will output the respective input pixel signals as they are.

In the above mentioned memory 175, the writing in and reading out addresses will be instructed by a memory address instructing part 176. This memory address instructing part 176 and the above mentioned driving part 172 will have timing and the like controlled by the controlling part 177.

When a pixel signal of one frame is stored in the above mentioned memory 175, the signal will be read out of this memory 175, will be D/A converted by a D/A converter 178, will be input into a signal processing circuit 179 and will be processed to be a video signal. The video signal output from this signal processing circuit 179 will be input into a displaying part 180 such as a monitor in which the object image will be displayed.

The operation of this embodiment shall be explained in the following.

In the case of inspecting a cancer or the like by using the endoscope 171 of this embodiment, at a predetermined time before the inspection, a cancer resistor marked with a radio-isotope or a deoxyglucose likely to concentrate on a cancer will be injected into the body by venous injection or the like. Such a reagent will concentrate on the cancer and radioactive rays, for example, γ rays will be emitted out of the cancer.

When the insertable part 102 of the above mentioned endoscope 171 is inserted into the body cavity and the lamp 141 within the processing apparatus 105 is made to emit a light, the illuminating light emitted from this lamp 141 will enter the light guide 132 of the endoscope 171 at the entrance end, will be led to the tip part 110 through the light guide 132 and will be radiated to an object through the light distributing lens 131.

The optical image of this object will be formed on the CCD 11 by the objective lens system 112.

When the tip part 110 of the above mentioned endoscope 171 is opposed to a cancer, the γ rays emitted from this cancer will enter the collimator 111 through the aperture of this collimator 111, will bit a PN junction of the CCD 11 to produce a signal and will be detected.

The above mentioned CCD 11 will be driven by the driving part 172 and the pixel signal read out will be input into the comparator 173. In the ordinary observing mode, the above mentioned comparator 173 will compare respective input pixel signals with a reference value. The signal below the reference value will be stored as it is in a predetermined address of a memory 175 and the signal exceeding the reference value will have the same value as of the signal immediately before it and below the reference value stored in a predetermined address of the memory 175. When a pixel signal of one frame is stored in the above mentioned memory 175, the signal will be read out of this memory 175, will be D/A converted by the D/A converter 178 and will be processed by the signal processing circuit 179 to be a video signal and the video output from this signal processing circuit 179 will be input into the displaying part 180 in which the object image will be displayed. In this case, as the pixel having received noises by radioactive rays and having had the signal level made above the reference value has had the signal value replaced with the signal value of its adjacent pixel, the picture image displayed by the displaying part 180 will have no noise by the radioactive rays and will be easy to observe.

On the other hand, in the radioactive ray detecting mode, the above mentioned comparator 173 will output the respective input pixel signals as they are. Therefore, in this case, bright points by the radioactive rays will appear in the picture image displayed in the above mentioned displaying part 180 and thereby the radio active rays will be able to be detected.

At the time of detecting the radioactive rays, the illuminating light may be reduced or extinguished.

Thus, according to this embodiment, bright points by radioactive rays will not appear in the observed picture image which is by the endoscope 171 and a picture image easy to see and to observe will be obtained.

In the above mentioned endoscope, the CCD 11 is also an imaging means and radioactive ray detecting means but, as shown in FIG. 19, apart from the CCD 11, a radioactive ray detecting means such as a semiconductor radioactive ray detector 181 may be provided in the tip part 110 of the insertable part 102 of the endoscope 171. The above mentioned semiconductor radioactive active ray detector 181 is connected to a signal processing circuit (not illustrated) through a signal line 182 so that the radioactive ray information from this signal processing circuit may be displayed on the displaying part 180 or a displaying means different from the displaying part 180.

The signal value of the pixel of a signal exceeding the reference value may be replaced with the signal value of the pixel of a signal below the reference value of the pixel not immediately before but near that pixel. In this case, the above mentioned process may be made while the pixel signal of the CCD 11 is once stored in a memory, is read out of this memory and is stored again in another memory.

The value to be replaced with the value of the signal exceeding the reference value is not limited to be the value of the adjacent pixel but may be a value of the signal reduced to a predetermined rate, a value of the signal subtracted by a constant value or a constant value.

Also, the pixel signal from the CCD 11 may be processed to be converted to a video signal, this video signal may be compared with the reference value and the signal of the signal part above the reference value may be replaced with a predetermined value. In this case, the signal above the reference value may be clipped.

The color imaging system is not limited to be of the simultaneous type but may be of a field sequential type switching the illuminating light sequentially to R, G, B, etc.

As explained above, according to this embodiment, as the signal of the signal part exceeding the reference value when the signal from the solid state imaging device is compared with the reference value can be replaced with a predetermined value, there is an effect that, in an ordinary observation, a picture image having had noises on the picture surface by radioactive rays reduced and easy to observe can be obtained.

Now, as described above, in the case of concentrating a substance marked with a radioactive substance on a tumor such as of a cancer to detect radioactive rays, in fact, some radioactive rays will be emitted from parts other than the tumor part. Therefore, there is a problem that the signal by the radioactive rays emitted from the parts other than this tumor part will become background (noise), the radioactive ray image of the tumor part will not be seen and the S/N ratio will deteriorate.

Therefore, examples of a radioactive ray detecting endoscope whereby the influence of the radioactive rays from parts other than the object part can be reduced are shown in the following 11th and 12th embodiments.

The 11th embodiment of the present invention is shown in FIGS. 20 and 21.

An endoscope 171 in this embodiment is of the same formation as of the endoscope 171 in the 10th embodiment.

On the other hand, the processing apparatus 105 is provided with a lamp 141 emitting an illuminating light so that the illuminating light emitted from this lamp 141 will enter a light guide 132 at the entrance end and with a driving part 172 and A/D converter 183 connected to the CCD 11 through signal lines 126 and a connector 106. The above mentioned CCD 11 will be driven by the above mentioned driving part 172 and the pixel signal read out of this CCD 11 will be input into the above mentioned A/D converter 183, will be A/D converted by this A/D converter 183 and will be stored in a memory (1) 184., The signal read out of the above mentioned memory (1) 184 will be processed by a signal processing part 185 to be a video signal and then will be stored in a memory (2) 188. The above mentioned memory (1) 184 and memory (2) 188 will have writing-in and reading-out address instructed by a memory address instructing part 176. The memory address instructing part 176 and the above mentioned driving part 172 will have the timing or the like controlled by a control part 177.

The operation of the above mentioned memories (1) 184 and (2) 188 shall be explained with reference to FIG. 21.

When data for one picture surface is stored in the memory (1) 184, by the memory address instructing part 176, as shown in FIG. 21 (A), addresses of one or a plurality of data read out of the memory (1) 184 will be set at random. In FIG. 21, the hatched parts represent addresses. The data of these set addresses will be read out of the memory (1) 184, will be processed by the signal processing part 185 and will be stored in the predetermined addresses in the memory (2) 188, that is, in the same addresses as in the memory (1) 184. This shall be the first time operation.

Then, the contents of the memory (1) 184 will be cleared and new signals from the CCD 11 at a different time will be stored in the memory (1) 184. As a second time operation, again by the memory address instructing part 176, as shown in FIG. 21 (B), addresses of one or a plurality of data read out of the memory (1) 184 will be set at random. However, in this case if there is the same address as the address set before, it shall be made invalid and another address will be set. The data of this set address will be read out of the memory (1) 184, will be processed by the signal processing part 185 and will be stored in the predetermined addresses in the memory (2) 188.

Even after a third time as is shown in FIG. 21 (C), the above operation will be repeated until the data for one picture surface is stored in the memory (2) 188.

When the data for one picture surface is stored in the above mentioned memory (2) 188, the data in this memory (2) 188 will be read out, will be D/A converted by a D/A converter 189 and will be input into a displaying part 180 such as a monitor in which the object image will be displayed.

The operation of this embodiment shall be explained in the following.

In the case of inspecting a tumor, for example, of a cancer by using the endoscope 171 of this embodiment, at a predetermined time before the inspection, a cancer resistor marked with a radio-isotope or a deoxyglucose likely to concentrate on a cancer will be injected into the body by venous injection or the like. Such a reagent will concentrate on the cancer and radioactive rays, for example, γ rays will be emitted out of this cancer.

When the insertable part 102 of the above mentioned endoscope 171 is inserted into the body cavity and the lamp 141 within the processing apparatus 105 is made to emit a light, the illuminating light emitted from this lamp 141 will enter the light guide 132 of the endoscope 171 at the entrance end, will be led to the tip part 110 by the light guide 132, will pass through the light distributing lens 131 and will be radiated to the object.

The optical image of this object will be formed on the CCD 11 by the objective lens system 112.

When the tip part 110 of the above mentioned endoscope 171 is opposed to a cancer, the γ rays emitted from this cancer will enter the collimator 111 through the aperture of the collimator 111, will hit a PN junction of the CCD 11 to produce a signal and will be detected.

The above mentioned CCD 11 will be driven by the driving part 172 and the pixel signal read out will be A/D converted by the A/D converter 183 and then will be stored in the memory (1) 184. By such an operation of the memory (1) 184 and memory (2) 188 as is described above signals from the CCD 11 at different times will be stored in the memory (2) 188 as divided into a plurality of times until one picture surface is formed by a combination of different pixels not overlapped or by each pixel. When the data for one picture surface is stored in the memory (2) 188, the data of this memory (2) 188 will be read out, will be D/A converted by the D/A converter 189 and will be input into the displaying part 180 in which bright points by radioactive rays will appear together with the object image and thereby the radioactive rays will be detected.

Now, the probability of the radioactive rays, that is, the background from parts other than tumor part such as a cancer entering the same pixels of the CCD 11 is smaller than the probability of the radioactive rays from the tumor part entering the same pixels of the CCD 11. Therefore, as in this embodiment, if the signals from the CCD 11 are stored in the memory (2) 188 as divided at a plurality of times, the probability of the signals by the background being present in the reading-out addresses in the memory (1) 184 will be smaller than the probability of the signals by the radioactive rays from the tumor part being present in the reading-out addresses in the memory (1) 184 and therefore the signals by the background among the signals stored in the memory (2) 188 will be few.

Thus, according to this embodiment, the influence of the radioactive rays from parts other than the tumor part can be reduced, the radioactive ray image of the tumor part will become easy to see and the S/N ratio will improve.

At the time of detecting radioactive rays, the illuminating light may be reduced or extinguished.

The 12th embodiment is of the memory 191. One or a plurality of data read out of the range 191a by the memory address instructing part 176 will be set at random. The data of these set addresses will be stored in predetermined addresses in the range of 191b of the other picture surface in the above mentioned memory 191 through the signal processing part 185. When the data of one picture surface is stored in the above mentioned range 191b, this range 191b will be read out, will be D/A converted by the D/A converter 189 and will be input into the displaying part 180.

According to this embodiment, the number of memories can be reduced.

The other formations, operations and effects are the same as in the 11th embodiment.

The addresses in the case of storing the data as divided at a plurality of times in the range 191b in the memory (2) 188 or memory 191 may be predetermined instead of being set at random.

In case an XY address type imaging device such as a MOS type imaging device is used as a solid state imaging device, this imaging device may be read out as divided at a plurality of times by a combination of different pixels set, for example, at random and signals for one picture surface may be stored in a memory.

The color imaging system is not limited to be of the simultaneous type but may be of a field sequential type switching the illuminating light sequentially to R, G, B, etc.

As explained above, according to the 11th and 12th embodiments, as signals from the solid state imaging device at different times are stored in the storage means as divided at a plurality of times by a combination of different pixels or at each of different pixels, there are effects that the signals by the radioactive rays from parts other than the object part can be decreased and the influence of the radioactive rays from parts other than the object part can be reduced.

The 13th embodiment of the present invention is shown in FIGS. 23 to 25.

In the first to twelfth embodiments, the direction of the radioactive ray generating source is sensed by using a collimator but, in this embodiment, the direction of the radioactive ray generating source can be sensed by using no collimator.

As shown in FIG. 23, two CCD's 193A and 193B different from each other in the visual field direction are arranged in the tip part 6 of the insertable part 2 of the endoscope. For example, one CCD 193A is set in the straight view direction and the other CCD 193B is set in the side view direction.

The output signals of the above mentioned respective CCD's 193A and 193B will be input respectively into amplifiers 196A and 196B within a radioactive ray detecting part 195 through signal lines 194A and 194B, will be amplified by these amplifiers 196A and 196B and then will be input into a comparator 197 which will compare the levels of the output signals of both CCD's 193A and 193B and will deliver a signal showing the direction of the radioactive ray generating source from the rate to a displaying part 198 in which the direction of the radioactive ray generating source will be displayed.

The other formations of the endoscope, that is, the formations of the illuminating optical system and channel are the same as in the first embodiment. The above mentioned both CCD's 193A and 193B may be provided with respective objective optical systems or only one of them may be provided with an objective optical system and the other may only detect radioactive rays.

The operation of this embodiment shall be explained in the following with reference to FIGS. 24 and 25.

When the illuminating light is extinguished or reduced, in case a tumor 199 which is a radio active ray generating source is located forward of the tip part 6, that is, forward of the CCD 193A as shown in FIG. 24, the radioactive rays generated from the tumor 199 will enter the CCD 193A more than the CCD 193B and the CCD 193A will output a larger signal. Thereby, the tumor 199 can be known to be located forward of the CCD 193A. The levels of the output signals of the above mentioned both CCD's 193a and 193b will be compared by the comparator 197 and the tumor 199 will be displayed in the displaying part 198 to be located forward of the CCD 193A.

Next when the illuminating light is extinguished or reduced, in case the tumor 199 is located in an oblique direction intermediately between the CCD's 193A and 193B, the radioactive rays generated from the tumor 199 will enter the CCD 193A and CCD 193B at substantially the same rates and the CCD's 193A and 193B will output signals on substantially the same levels. The tumor 199 can be known thereby to be located in the oblique direction intermediately between the CCD's 193A and 193B as indicated by the arrow in the drawing. In this case, the tumor 199 will be displayed in the displaying part 198 to be located in the oblique direction intermediately between the CCD's 193A and 193B. Also, in this case, the position of the tumor 199 may be confirmed by displacing the tip part 6 as by curving the curvable part to approach a state as in FIG. 24.

Even in other states than in FIGS. 24 and 25, the direction of the radioactive ray generating source can be sensed from the rates of levels of the output signals of the CCD's 193A and 193B.

If the number of CCD's is increased, the position will be able to be confirmed more accurately.

In this embodiment, the CCD is used as a radioactive ray detecting means but, aside from the observing CCD, a plurality of radioactive ray detecting devices may be provided in the tip part 6.

Thus, according to this embodiment, there is an effect that, even if no collimator is used, the direction of the radioactive ray generating source can be sensed.

The 14th embodiment of the present invention is shown in FIG. 26.

An endoscope 701 is provided with an elongated, for example, flexible insertable part 702 and a thick operating part 703 connected to this insertable part 702 at the rear end. A flexible universal cord 704 is extended sidewise from the above mentioned operating part 703 and is provided at the tip with a connector 706 which is connected to a light source apparatus 707 emitting an illuminating light.

An eyepiece part 708 whereby an object image can be observed with a naked eye is provided at the rear end of the above mentioned of the operating part 703 and is fitted removably with an externally fitted television camera (briefly mentioned as a TV camera hereinafter) 709 which is connected to a video processing apparatus 712 and can deliver a video signal.

The video processing apparatus 712 is connected to a monitor 713 as an image displaying means and is to display an object image.

A frame 714 as a radioactive ray shielding means formed of radioactive ray attenuating material effective to attenuate radioactive rays such as lead is provided in the tip part of the above mentioned insertable part 702 and an aperture 716 provided in the front part of this frame 714 is positioned on the tip surface of the insertable part 702. An image forming lens system 717 as an image forming optical system is provided in the front part within this frame 714. The entrance end surface of an image guide fiber 718 formed of a fiber bundle such as an image transmitting means is provided in the image forming position of this image forming lens system 717. This image guide fiber 718 is curved to be separated from the optical axis of the image forming lens system 717 within the frame 714, is passed through the rear wall 719 of the frame 714 and is led to the eyepiece part 708 through the insertable part 702 and operating part 703. A semiconductor radioactive ray detector 721 as a radioactive ray detecting means is provided movably forward and rearward on the extension of the optical axis of the above mentioned image forming lens system 717 in the rear of the curve of the image guide fiber 718. This semiconductor radioactive ray detector 721 is connected to a radioactive ray detecting circuit 725 of a video processing apparatus 712 through a signal line 720. Further, the exit end surface of a light guide fiber 722 formed of a fiber bundle inserted through the above mentioned universal cord 704 and insertable part 702 is provided on the tip surface of the insertable part 702 so that an object, which can be observed with the above mentioned image forming lens system 717, may be illuminated. An illuminating light emitted from a light source lamp 723 provided within the light source apparatus 707 by being connected to the light source apparatus 707 and condensed by a condenser lens 724 will enter the entrance end surface of this light guide fiber 722 provided in the above mentioned connector 706.

A solid state imaging device 726 as an imaging means is provided within the TV camera 709 fitted to the above mentioned eyepiece part 708 so that on object image may be formed on the imaging surface of this solid state imaging device 726 by an image forming lens 736 through an eyepiece lens 734 provided in the rear of the exit end surface of the image guide fiber 718. A color filter array 737 of respective color transmitting filters of R (red), G (green), B (blue), etc. arranged in the form of a mosaic or the like is provided on the imaging surface of this solid state imaging device 726. A signal line 727 is connected to this solid state imaging device 726 and is connected to a video signal processing circuit 728 provided in the above mentioned video processing apparatus 712 so as to deliver a video signal. This video signal processing circuit 728 will drive the above mentioned solid state imaging device 726 and will process the output signal of the above mentioned solid state imaging device 726 so as to be a video signal.

The video signal produced by the above mentioned video signal processing circuit 728 will be output to the above mentioned monitor 713 through an adding circuit 729 and this monitor 713 will display the object image. In a radioactive ray detecting circuit 725, the output signal of the semiconductor radioactive ray detector 721 will be compared with a predetermined level. The radioactive ray detecting circuit 725 is connected to a character generating circuit 731 which will generate a predetermined character 732 in case a signal showing that the output signal of the semiconductor radioactive ray detector 721 is above a predetermined level is input from the above mentioned radioactive ray detecting circuit and will deliver this character 732 to the above mentioned adding circuit 729.

The operation of this embodiment shall be explained in the following.

In the case of inspecting a cancer by using the endoscope 701 of this embodiment, at a predetermined time before the inspection, a cancer resistor marked with a radio-isotope or a deoxyglucose likely to concentrate on a cancer will be injected into the body by venous injection or the like. Such a reagent will concentrate on the cancer 33 and radioactive rays, for example, $\gamma$ rays will be emitted from this cancer 33.

When the insertable part 702 of the above mentioned endoscope 701 is inserted through the mouth cavity and the light source lamp 723 is lighted, the illuminating light emitted from this light source lamp 723 will be condensed by the condenser lens 724, will enter the light guide fiber 722 on the entrance end surface, will be led to the tip part through this light guide fiber 722 and will be emitted from the tip toward the object. The object image will be formed on the entrance end surface of the image guide fiber 718 by the image forming lens system 717. The formed object image will be led through the image fiber 718 and will be imaged on the imaging surface of the solid state imaging device 726 through the eyepiece lens 734 and image forming lens 736. The output signal of the solid state imaging device 726 will be input into the video signal processing circuit 728 within the video processing apparatus 712 through the signal line 727 and will be processed to be a video signal. The video signal produced by this video signal processing circuit 728 will be input into the monitor 713 through the adding circuit 729 and the object image will be displayed in this monitor 713.

Now, when the tip part of the above mentioned endoscope 701 is opposed to the cancer 733, the radioactive rays emitted from this cancer 733 will enter the frame 714 through the aperture 716 of the frame 714 made of radioactive ray attenuating material such as lead, will pass through the image forming lens system 717 and image guide fiber 718 and will enter the semiconductor radioactive ray detector 721. At this time, the entering angle of the radioactive rays to the detector 721 will relate to the caliber of the aperture 716 and the distance between the aperture 716 and detector 721. That is to say, by moving the detector 721 forward and rearward, the visual field angle of the object image and the entering angle of the radioactive rays can be made to coincide with each other. The detector 721 will be fixed in the position in which the radioactive ray entering angle and the visual field angle coincide with each other to detect the radioactive rays. Thus, the radioactive rays will reach the detector 721. The output signal of the detector 721 will be input into the radioactive ray detecting circuit 725 within the video processing apparatus 712 through the signal line 720. In the radioactive ray detecting circuit 725, the input signal will be compared with a predetermined level. In case the signal is above this level, it will be output to the character generating circuit 731. By thus comparing the signal with the predetermined level, the influence of the background can be removed and, even in case the semiconductor detector 721 is photosensitive, the radioactive rays of the object image will be able to be measured in real time without extinguishing the light source lamp 723.

The character signal generated in the character generating circuit 731 will be output to the adding circuit 729 and will be superimposed on the video signal produced by the video signal processing circuit 728. The video signal on which this character signal has been superimposed will be output to the monitor 713. In this monitor 713, the object image and the character 732 showing that the cancer 733 is present within the now displayed object image will be simultaneously displayed.

As mentioned above, according to this embodiment, by superimposing the character 732 on the object image, it can be sensed that the radioactive ray generating source is present within the object image. Therefore, the presence of deep part cancer or lymphatic knot transfer can be easily confirmed and a treating method and curing method can be easily and positively determined.

A modification of the above mentioned video processing apparatus 712 is shown in FIG. 27.

In this apparatus 712, the video signal from the solid state imaging device 726 will be input and processed in a video signal processing circuit 761 and a video signal from this video signal processing circuit 761 will be input into a displaying apparatus 762 such as a monitor in which the object image will be displayed.

On the other hand, the radioactive ray detecting signal from the radioactive ray detector 721 will be amplified by an amplifier 763 and will be shaped to be of a countable waveform by a waveform shaping circuit 764. The output signal of this waveform shaping circuit 764 will be counted by a pulse counting circuit 765 for the time designated by a timer 766. The output from the above mentioned pulse counting circuit 765 will be input into an operating circuit 767 and will be operated, for example, to compare the number of pulses counted in the above mentioned pulse counting circuit 765 with a reference value. The output of this operating circuit 767 will be input into a displaying apparatus 768 and buzzer 769. In case it is determined by the above mentioned operating circuit 767 that, as the number of pulses exceeds the reference value, the radioactive rays will be above the predetermined level, this fact will be displayed in the displaying apparatus 768 or by the buzzer 76( will be sounded.

The displaying apparatus for detecting radioactive rays and for video images may be the same.

The 15th embodiment of the present invention is shown in FIG. 28.

An insertable part 702 of an endoscope 701 of this embodiment is provided with a tip body 740 as a radioactive ray shielding means formed of radioactive ray attenuating material as, for example, stainless steel. This tip body 740 is provided in the lengthwise direction with an observing aperture 741 and illuminating through hole 742. An image forming lens system 717 as an image forming optical system is provided in the front part of this observing aperture 741. In the rear of this image forming lens system 717, a mirror 743 is provided so as to bend the optical axis substantially at right angles with the lengthwise direction. A mirror 744 is further provided as opposed to this mirror 743 so as to lead the optical axis bent by the above mentioned mirror 743 again in the lengthwise direction. In the rear of this mirror 744, an image guide fiber 718 formed of a fiber bundle, is provided on the entrance end surface so as to be able to input an object image.

In the rear of the above mentioned mirror 743 and on the extension of the optical axis of the image forming lens system 717, a semiconductor radioactive ray detector 721 as a radioactive ray detecting means is arranged so that the radioactive rays having passed through the image forming lens system 717 and mirror 743 may enter it. The radioactive ray entering angle of this semiconductor radioactive ray detector 721 will be regulated by the tip body 740 so as to be the same as the visual field angle of the image forming lens system 717.

A light guide filter 722 formed of a fiber bundle is inserted through the above mentioned illumination through hole 742 so as to radiate an illuminating light to on object to be imaged.

The other formations are the same as in the 14th embodiment.

In this embodiment, as the mirrors 743 and 744 are used so that the image guide fiber 718 may not be curved within the tip body 740, the length of the tip part can be made short and the image guide fiber 718 will not be broken.

The other operations and effects are the same as in the 14th embodiment.

The 16th embodiment of the present invention is shown in FIG. 29.

In this embodiment, the present invention is applied to an electronic endoscope.

A frame 747 as a radioactive ray shielding means having an aperture 746 is provided forward in the tip part of an insertable part 702. The aperture 746 of this frame 747 is positioned in the tip part of the insertable part 702. An objective lens system 748 as an image forming optical system is arranged within the aperture 746. Further, in the rear of the objective lens system 748, a rectangular prism 749 is provided so as to bend the optical axis of this objective lens system 748 substantially at right angles with the lengthwise direction of the insertable part 702. Above this rectangular prism 749, a video solid state imaging device 751 as an image transmitting means is arranged on the above mentioned bent optical axis.

The output signal of the solid state imaging device 751 will be output to the video signal processing circuit 728 described in the 14th embodiment through a signal line 727.

In the rear of the rectangular prism 749 and on the extension of the optical axis of the objective lens system 748, a light intercepting plate 752, a collimator 753 and a radioactive ray detecting solid state imaging device 754 as a radioactive ray detecting means are overlapped and provided in the mentioned order from the front. The collimator 753 in formed of a radioactive ray attenuating material to be like a plate, is provided in the central part with a radioactive ray transmitting hole 756 in the lengthwise direction of the insertable part 702 and is pasted to the imaging surface of the solid state imaging device 754 so as to transmit only through the transmitting hole the radioactive rays entering the solid state imaging device 754 and to regulate the entering angle to the solid state imaging device 754 of the radioactive rays. The above mentioned light intercepting plate 752 is provided so that light may be intercepted not to enter the radioactive ray transmitting hole 756 and the solid state imaging device 754 may detect only the radioactive rays. This solid state imaging device 754 will output an output signal to the radioactive ray detecting circuit 725 described in the 14th embodiment through a signal line 720.

The exit end surface of a light guide fiber 722 as an illuminating optical system is provided on the tip surface of the insertable part 702 so as to radiate the illuminating light to an object to be imaged.

The other formations are the same as in the 14th embodiment.

In this embodiment, as compared with the 14th and 15th embodiments, as the entering angle to the solid state imaging device 754 of the radioactive rays is regulated further by the collimator 753 in addition to the aperture 746, the radioactive rays substantially in the central part of the object image can be measured. Therefore, the range of the character displayed in the monitor may be made to correspond to the radioactive ray detecting part of the solid state imaging device 754.

Also, as the solid state imaging device 751 is used instead of the image guide fiber, an object image high in resolution can be obtained. Further, since the signal line 727 instead of the image guide fiber is inserted through the insertable part 702, the outside diameter of the insertable part 702 can be made smaller.

The other operations and effects are the same as in the 14th embodiment.

The radioactive ray detecting means is not limited to the semiconductor radioactive ray detector and solid state imaging device but a scintillator detector emitting a fluorescence when radioactive rays enter may be provided so that the radioactive rays may be detected by photoelectrically converting this fluorescence.

Further, the color imaging system is not limited to be of a simultaneous type provided with a color filter array on the imaging surface of a solid state imaging device but may be of a field sequential type switching the illuminating light sequentially to R, G, B, etc.

As explained above, according to the 14th to 16th embodiments, as the radioactive ray detecting means is provided within the frame made of a radioactive ray attenuating material and the entering angle of the radioactive rays entering this radioactive ray detecting means is regulated by the aperture, there is an effect that the radioactive ray generating source included in the observed part can be easily sensed simultaneously with the observation of the endoscope image.

The 17th embodiment of the present invention is shown in FIG. 30.

As shown in FIG. 30, an endoscope 801 is provided with an elongated, for example, flexible insertable part 802, a thick operating part 803 connected to this insertable part 802 at the rear end and an eyepiece part 807 provided at the rear end of this operating part 803. A light guide cable 804 is extended sidewise from the above mentioned operating part 803 and is provided at the end with a connector 806 removably connected to a light source apparatus 805.

An observing window, illuminating window and channel aperture are provided in the tip part 810 of the above mentioned insertable part 802. An objective lens system 812 is fitted inside the above mentioned observing window. The tip surface of an image guide 813 made of a fiber bundle is arranged in the image forming position of this objective lens system 812. This image guide 813 is inserted through the insertable part 802 and is opposed on the rear end surface to an eyepiece lens 808 provided within the above mentioned eyepiece part 807 so that an object image formed by the above mentioned objective lens system 812 will be transmitted to the eyepiece part 807 through the image guide 813 and will be observed from this eyepiece part 807'.

The same as in the 14th embodiment, an externally fitted TV camera can be removably fitted to the above mentioned eyepiece part 807.

A light distributing lens 831 is arranged inside the illuminating window in the above mentioned tip part 810. A light guide 832 made of a fiber bundle is connected to this light distributing lens 831 on the rear end side, is inserted through the insertable part 802. Operating part 803 and light guide cable 804 are connected at the entrance end to the connector 806.

A channel 835 is formed within the above mentioned insertable part 802 and is opened on the tip side with the treating tool channel aperture in the above mentioned tip part 810 and on the base end side on the side of the operating part 803 to form an inserting part 836.

On the other hand, the above mentioned light source apparatus 805 is provided with a lamp 841 emitting an illuminating light emitted from this lamp 841 will enter the above mentioned light guide 832 at the entrance end.

Now, a radioactive ray detecting probe 850 can be inserted through the above mentioned channel 835 and has a tube 851 insertable through the above mentioned channel 835 and a transparent balloon 852 fitted to the tip part of this tube 851. The above mentioned balloon 852 can project forward from the channel aperture of the tip part 810 and can be arranged within the visual field of the above mentioned objective lens system 812. The above mentioned tube 851 is led at the base end out of the inserting port 836 so that a liquid scintillator may be injected into the tube 835 from this base end. This liquid scintillator 855 will flow into the above mentioned balloon 852 through the above mentioned tube and will be enclosed within this balloon 852. The above mentioned liquid scintillator 855 is a substance emitting a fluorescence when in contact with radioactive rays and is preferable to be high in transparency to be used in this embodiment.

The operation of this embodiment shall be explained in the following.

In the case of inspecting a tumor such as a cancer by using the endoscope 801, at a predetermined time before the inspection, a cancer resistor marked with a radioisotope or a deoxyglucose likely to concentrate on a cancer is injected into the body as by venous injection. Such a reagent will concentrate on such tumor as a cancer and radioactive rays, or example, γ rays will be emitted from the tumor.

When the insertable part 802 of the above mentioned endoscope 801 is inserted into the body cavity and the lamp 841 within the light source apparatus 805 is made to emit a light, the illuminating light emitted from this lamp 841 will enter the light guide 832 of the endoscope 801 at the entrance end, will be led to the tip part 810 through the light guide 832 and will be radiated to an object through the light distributing lens 831. The optical image of this object will be formed on the tip surface of the image guide 813 by the objective lens system 812, will be transmitted to the eyepiece part 807 through this image guide 813 and will be observed from this eyepiece part 807.

On the other hand, when radioactive rays are to be detected, the radioactive ray detecting probe 850 will be inserted through the channel 835 and the liquid scintillator 855 will be enclosed within the balloon 852.

Then, as shown in FIG. 30, while the above mentioned balloon 852 is kept close to or in contact with the body cavity wall 857, the part where the liquid scintillator 855 emits a light will be looked for. When the above mentioned balloon 852 is opposed to the tumor 858, the γ rays emitted from this tumor 858 will contact the liquid scintillator 855 within the above mentioned balloon 852 and this liquid scintillator 855 will emit a light. By the light emission of this liquid scintillator, the radioactive ray generating part, that is, the tumor 858 can be detected.

In the case of looking for the radioactive ray generating part with the above mentioned balloon 852, if the illuminating light is reduced and, when the part where the liquid scintillator 855 emits a light is discovered, if the illuminating light is increased and this light emitting part is observed, the radioactive ray generating part will be more easily discovered.

Thus, according to this embodiment, the radioactive ray generating part can be detected, with the liquid scintillator 855 within the visual field of the endoscope 801 and can be observed with the endoscope 801.

Also, in this embodiment, as the liquid scintillator 855 is enclosed within the balloon 852, by keeping this balloon 852 close to or in contact with the body cavity wall, in the parts in a wide range, simultaneously, the radioactive ray generating part can be looked for and easily discovered.

By using the liquid scintillator 855 high in transparency, even through this liquid scintillator 855, the radioactive ray generating part can be observed and can have its position easily made to correspond to the endoscope image.

Not only the radioactive ray detecting probe but also a treating tool such as a forceps can be inserted through the above mentioned channel 835.

The 18th embodiment of the present invention is shown in FIG. 31.

In this embodiment, a transparent case 860 for enclosing a liquid scintillator is removably fitted to a channel aperture in the tip part 810. This case 860 is made to enter at least partly the visual field of an objective lens system 812. A liquid scintillator 855 is to be enclosed within the above mentioned case 860 through a channel 835. While the case 860 enclosing this liquid scintillator 855 is kept close to or in contact with the body cavity wall 857, the part where the liquid scintillator 855 emits a light will be looked for.

The other formations, operations and effects are the same as in the 17th embodiment.

Instead of the case 860 in the 18th embodiment, the balloon 852 in the 17th embodiment may be fitted to the channel aperture.

Also, a liquid scintillator enclosing member such as a balloon may be fitted to the tip aperture part of a water feeding channel of the endoscope.

The 19th embodiment of the present invention is shown in FIG. 32.

In this embodiment, two image guides are provided as an observing means. One image guide 813 is exclusively for observation and is provided on the tip side with an objective lens system 812. The other image guide 871 is for both radioactive ray detection and observation and is provided on the tip side with a transparent rod-like scintillation crystal 872 through an objective lens system 874. A tubular collimator 873 is provided on the outer periphery on the front end side of the above mentioned scintillation crystal 872, objective lens system 874 and image guide. The above mentioned image guide 871 is extended at the rear end to the second eyepiece part not illustrated.

In this embodiment, when radioactive rays such as γ rays enter the above mentioned scintillation crystal 872, it will emit a light. The light from this scintillation crystal 872 will be transmitted to the second eyepiece part by the image guide 871 and will be observed together with the object image from this second eyepiece part and the radioactive ray generating part, that is, the tumor can be detected.

The other formations, operations and effects are the same as in the 17th embodiment.

The 20th embodiment of the present invention is shown in FIG. 33.

In this embodiment, a light detector 877 is bonded to the rear end of a scintillation crystal 872 insertable through a channel 837. The above mentioned scintillation crystal 872 and light detector 877 are covered except on the front end surface with a tubular transparent collimator 878. A signal cable 879 which is also an operating wire is connected to the above mentioned light detector 877, is inserted through the channel 835 and is connected, for example, to a signal processing part (not illustrated). The output signal of this signal processing part will be transmitted to a displaying apparatus (not illustrated) in which the radioactive ray information will be displayed.

In this embodiment, by operating the above mentioned signal cable 879, the scintillation crystal 872 can be arranged within the visual field of the objective lens system 812 and, by the light emission of this scintillation crystal, the radioactive ray generating part can be detected and the radioactive ray information can be displayed in the displaying apparatus.

In this embodiment, even when the scintillation crystal 872 is retreated into the channel 835, the radioactive rays will be able to be detected.

The other formations, operations and effects are the same as in the 17th embodiment.

The 21st embodiment of the present invention is shown in FIG. 34.

In this embodiment, a radioactive ray detecting probe 880 as in the following is provided. This radioactive ray detecting prove 880 is formed of an operating wire 881 inserted through a channel 835 of an endoscope 801 and a scintillation crystal 882 fitted to the tip of this operating wire 881. A housing part 883 which can house the above mentioned scintillation crystal 882 is formed in a channel aperture of a tip part 810 of the endoscope 801.

In this embodiment, by operating the above mentioned operating wire 881, the scintillation crystal 882 can be arranged within the visual field of the objective lens system 812 and, by the light emission of this scintillation crystal 882, the radioactive ray generating part can be detected. When the radioactive rays are not detected, the scintillation crystal 882 will be able to be housed in the housing part 883.

The other formations operations and effects are the same as in the 17th embodiment.

The 22nd embodiment of the present invention is shown in FIGS. 35 and 36.

In this embodiment, an air feeding channel 885 is provided within an insertable part 802 of an endoscope 801. A balloon 886 made by shaping a sheet-like plastic scintillator is fitted to the aperture of the air feeding channel 885 in a tip part 810. As shown in FIG. 36, when the above mentioned balloon 886 is filled with air through the air feeding channel 885, this balloon 886 will be inflated to enter the visual field of the objective lens system 812.

In this embodiment, when the balloon 886 is inflated to enter the visual field of the objective lens system 812, the radioactive ray generating part will be able to be detected by the light emission of the balloon made of the sheet-like plastic scintillator.

The balloon 886 made of the sheet-like plastic scintillator may be fitted to the tip of on air feeding tube inserted through the channel 835 and may be projected out of and retreated into the tip part 810.

The other formations, operations and effects are the same as in the 17th embodiment.

The 23rd embodiment of the present invention is shown in FIG. 37.

In this embodiment, a scintillation crystal 888 is projected forward so as to enter the visual field of an objective lens system 812 is fixed to a tip part 810 of an endoscope 801.

In this embodiment, by the light emission of the scintillation crystal 888 arranged within the visual field of the objective lens system 812, the radioactive generating part can be detected.

The other formations, operations and effects are the same as in the 17th embodiment.

In the 17th to 23rd embodiments, the endoscope may be an electronic endoscope wherein an object image is imaged by a solid state imaging device arranged in the image forming position of an objective lens system.

Also, the radioactive rays are not limited to be $\gamma$ rays but may be $\alpha$ rays and $\beta$ rays. In the case of using $\alpha$ rays, a gas scintillator can be used instead of the liquid scintillator and solid scintillator.

As explained above, according to the 17th to 23rd embodiments, there is an effect that, by arranging the scintillator within the visual field of the observing means, the radioactive ray generating part can be detected and observed.

The 24th embodiment of the present invention is shown in FIGS. 38 to 40.

A radioactive ray detecting endoscope 301 comprises a tip part 302, insertable part 303, operating part 304, universal cord 305 and connector part 306 and is removably fitted to an external unit 307 by the connector part 306. A cover glass 308, objective lens 309 and reflecting prism 310 are arranged as an observing optical system in the tip part 302 and one end of an image guide fiber 311 is positioned on the image surface position of the objective lens 309. The image guide fiber 311 is inserted through the insertable part 303 from the tip part 302, is extended to the operating part and is arranged as opposed at the other end to an eyepiece 312 in an eyepiece part 337. An illuminating window 313 is also provided adjacently to the cover glass 308 in the tip part 302. An illuminating light guide 314 is arranged as opposed at one end to the illuminating window 313 is inserted through the insertable part 303, operating part 304 and universal cord 305 and is positioned at the other end on the end surface of a light guide mouthpiece 315 of the connector part 306. Further, a forceps channel 316 is opened in the tip part 302, is inserted, through the insertable part 303 and is opened at the other end in a part of the operating part 304. The forceps channel 316 is branched though not illustrated, is extended to the connector part 306 and has a function as of a suction tube path and also a function of feeding air and water the same as in an ordinary endoscope.

An externally fitted TV camera is to be removably fitted to the above mentioned eyepiece part 337 the same as in the 14th embodiment.

A radioactive ray detecting part 320 is provided at the front end of the tip part 302 of this endoscope 301 and comprises a collimator 321 expanded upward (in the observing direction by the observing optical system) and a scintillator 322 provided in the bottom part. A plastic cover 323 is arranged at the upper end of the collimator 321. The scintillator 322 is of an NaI (Tl) or CsI (Tl) single crystal and is sealed on the collimator 321 side with an aluminum case 324 and on the endoscope 301 side with a glass plate 325. A light guide 326 is arranged at one end as opposed to the glass plate 325 within the tip part 302, is inserted through the insertable part 303, operating part 304 and universal cord 305 to the connector part 306 and is positioned at the other end on the end surface of a mouth piece 327.

The external unit 307 has an external unit side connector in which the connector part 306 is removably inserted and has an illuminating light source 328 arranged as opposed to the light guide mouthpiece 315 when the connector part 306 is inserted. A photoelectronic multiplying tube 329 opposed to a mouthpiece 327, a processing part 330 including an amplifying circuit and counting circuit and a displaying apparatus 331 are provided as enclosed with a light intercepting plate 332 in the external unit 307.

The operation of this 24th embodiment shall be explained in the following.

In the case of the diagnosis, a resistor marked with a radio-isotope and injected into the body of the patient will concentrate on a tumor part 333. The radio isotope of the resistor will emit positrons which will hit nearby electrons and will emit γ rays 334. The γ rays 334 will be emitted in all directions but will be partly transmitted to the endoscope 301 through the body cavity wall 335, will pass through the plastic cover 323 and will enter the collimator 321 and scintillator 322. A fluorescence will be emitted by the γ rays within the scintillator 322, will enter the light guide 326 through the glass plate 325, will be led to the external unit 307, will be amplified by the electronic multiplying tube 329, will be photoelectrically converted, will be further amplified by the processing part 330, will have the light amount counted and will output a signal adapted to a displaying apparatus 331 as, for example, a digital counter. At the same time, the body cavity wall 335 will be illuminated through the illuminating light guide 314 by the light source 328 within the external unit 307 and the affected part will be observed with the eyepiece part 337 through the observing optical system so that the presence of the radio-isotope concentrating part in the inner part of the affected part may be confirmed. The presence of the radio-isotope will confirm the presence of a tumor. Also, by biopsizing the surface of the body cavity wall 335 by utilizing the forceps channel 316, if there is a tumor part on the body cavity surface its presence will be able to be confirmed. If the tumor can not be confirmed to be present by the biopsy, it will be present in the deep part.

According to this 24th embodiment, as the collimator and scintillator are arranged by utilizing the largest diameter part of the insertable part of the endoscope, the radioactive ray detector can be provided without enlarging the diameter of the endoscope and the pain of the patient can be reduced.

The 25th embodiment of the present invention is shown in FIGS. 41 to 43.

FIG. 41 shows only an endoscope tip part 341 and illustrates only a radioactive ray detecting part 341 but not an observing optical system and others but is of the same formation as in the 24th embodiment. The detecting part 341 has a collimator provided at the front end of the endoscope tip part 340 and comprising a first tube 342, a second tube 343 slidable in close contact with the outer periphery of the first tube and a plastic cover 344 provided at the upper end of the second tube 343. A scintillator 322 sealed with an aluminum case 324 is provided in the bottom of the first tube 342. An actuator 345 made of a form memorizing alloy is provided between the second tube 343 and the endoscope tip forming part and is connected with an electric wire (not illustrated) so as to be controllable by being switched by the operator from outside. The fluorescence emitted by the scintillator 322 will be led to an external unit 307 by a light guide 326 the same as in the 24th embodiment.

In this embodiment, the affected part is observed and γ rays are detected the same as in the 24th embodiment but the endoscope is inserted into the body cavity and γ rays are detected with the second tube 343 shown in FIG. 42 as shortened. When the γ rays can be detected, the form memorizing alloy of the actuator 345 will be electrified and heated, the actuator 345 will be driven as shown in FIG. 43 and the second tube 343 will be extended upward. In the state in FIG. 43, the cover 344 at the upper end of the second tube 343 will be pressed against the body cavity wall to detect γ rays. After the tumor is confirmed, when the electrification of the actuator 345 is stopped, the form memorizing alloy will be cooled to return to the original form, the second tube will be in the state in FIG. 42 and the endoscope will be able to be pulled out of the body cavity. The actuator 345 is not limited to be made of a for memorizing alloy but a wire drive or fluid pressure may be utilized.

According to this embodiment, as the collimator is made fine and retractable, the range of the presence of γ rays can be limited and confirmed and the diagnosing ability of the position and size of a tumor can be improved.

The 26th embodiment of the present invention is shown in FIG. 44.

In this embodiment, a small photoelectronic multiplying tube 350 is used instead of the light guide of the 24th embodiment. A collimator 321 having a plastic cover 323 at the upper end is provided at the front end of an endoscope tip part 351 and a scintillator 322 sealed with an aluminum case 324 is arranged in the bottom of the collimator 321. The small photoelectronic multiplying tube 350 is arranged as opposed to the scintillator 322 within the tip part 351 and is a channel or the like of a microchannel plate.

A plurality of radioactive ray detecting parts may be provided along the insertable part and the scintillator may be of a material for not only γ rays but also α and β rays in response to the kind of radioactive rays. The image guide fiber of the observing optical system may be formed of a solid state imaging device as a CCD.

As explained above, according to the 24th to 27th embodiments as a radioactive ray, the radioactive ray detecting part can be made small and the endoscope tip can be made small to make a radioactive ray detecting endoscope with which the pain of the patient is little.

The 27th embodiment of the present invention is shown in FIGS. 45 to 53.

FIG. 45 is a view showing an entire apparatus. The reference numeral 401 represents an endoscope to be inserted into a body cavity, 402 represents a radioactive ray detecting apparatus arranged outside the body and 403 represents a bed apparatus holding the patient. The radioactive ray detecting apparatus 402 has a base 404 and a pillar 405 sliding in the vertical direction as supported on the base 404. A C-arm 407 is fitted through a shaft 406 to the upper side surface of the pillar 405. The shaft 406 is slidable in the horizontal direction to the pillar 405. The C-arm 407 is rotatable with the shaft 406 as a center. A body outside type γ ray detecting part 409 in a curved surface form is fitted to an upper arm 408 of the C-arm 407. γ ray generating parts 410 are fitted as directed downward in four peripheral places of the detecting part 409. An X-ray generating apparatus 411 is fitted as directed downward on the side of the detecting part. An X-ray TV camera 413 is fitted to a lower arm 412 as opposed to the X-ray generating apparatus 411. Further, an electronic sector type ultrasonic probe 414 and a probe 414 supporting apparatus 415 are provided in the central part of the C-arm 407. The probe 414 is supported by the supporting apparatus 415 so as to be movable in the direction indicated by the illustrated arrows.

The bed apparatus 403 comprises a base 416, pillar 417 and bed 418 which can be adjusted in the direction indicated by the illustrated arrows.

The endoscope 301 has a body cavity γ ray detecting part 320 at the tip of an insertable part 303. A TV camera 423 is fitted to an eyepiece part 337 at the rear end of an operating part 304 connected with the insertable part 303. A universal cord 305 is extended from this operating part 304 and is connected to a data processing apparatus 426 by a connector 306 provided at the other end. The signal from the body cavity γ ray detecting part 320 will be transmitted into the data processing apparatus 426 by the connector 306 through the endoscope 301. A signal cable 427 from the TV camera 423 is also connected to this data processing apparatus 426. Further, the respective signals from the body outside type γ ray detecting part 409, X-ray TV camera 413 and ultrasonic probe 414 will be also transmitted into the data processing apparatus 426 which is provided with an X-ray picture image monitor 428, endoscope image monitor 429 and ultrasonic monitor 430.

The formation of the above mentioned endoscope 401 is the same as in the 24th embodiment. The endoscope external unit 307 is provided within the data processing apparatus 426.

The body outside type γ ray detecting part 409 shall be explained in the following with reference to FIGS. 46 and 47. In the detecting part 409, a plurality of γ ray detectors 460 are arranged in the form of a matrix so as to converge to a position F separated by a distance l to form a part of a cylinder. In the case of this embodiment, there are 80 detector 460. Each of these γ ray detectors 460 comprises a collimator, scintillator and photoelectronic multiplying tube and is made directive to the position F. The γ ray generators 410 provided around the detecting part 409 are set to be also directive to the above mentioned position F. That is to say, in the γ ray generating part 410, a path 462 is formed in a case 461 made of lead and a radio-isotope 463 is arranged in the deepest part of the path 462. A shutter 464 is formed in the path 462 and is opened and closed by a link 465 and solenoid 466. Further, the X-ray generating apparatus 411 and X-ray TV camera 413 are also arranged to include the above mentioned position F. The collimator 321 in FIGS. 38 and 39 is in an upward expanding form in one direction only but, in fact, as shown in FIGS. 46 and 47, the respective γ ray generating parts 410 can be seen in the position F and the collimator is conically opened in an entire enterable range.

The block diagram of the data processing apparatus 426 shown in FIG. 49 shall be explained in the following. Sensing signals from the body outside type γ ray detecting part 409 and body cavity inside γ ray detecting part 320 will be input into a γ ray sensing circuit 470 which has a flying time difference positive electron tomography of positrons CT based on the signals from both detecting parts 409 and 320 and a γ ray sensing function as of a single light quantum CT by only the light from the body cavity inside γ ray sensing part 320. A first coordinate converting circuit 471, second coordinate converting circuit 472 and third coordinate converting circuit 473 are connected on the output side of the γ ray sensing circuit 470 outputting the position information of the radioactive ray source determined by the flying time difference. On the other hand, the picture image signals from an X-ray TV camera 413, TV camera 423 and ultrasonic probe 414 are connected to respective picture image processing circuits 474, 475 and 476. The respective coordinate converting circuits 471, 472 and 473 and respective picture image signal processing circuits 474, 475 and 476 are connected to respective adders 477, 478 and 479 and are connected respectively to an X-ray picture image monitor 428, endoscope image monitor 429 and ultrasonic image monitor 430 through respective frame memories 480, 481 and 482. On the other hand, in case the body cavity inside γ ray sensing part 320 is used as a single light quantum CT, the output of the γ ray sensing circuit 470 will be connected to a position controlling apparatus 483 connected with a solenoid driving apparatus 484 and motor driving apparatus. The solenoid driving apparatus 484 is connected to solenoids 466 driving shutters 464 of γ ray generating parts 410. The motor driving apparatus 485 is connected to a motor 486 driving the base 404 of a radioactive ray detecting apparatus 402, motor 487 driving a C arm 407 and motor 488 driving a bed apparatus 403. The position coordinate information of the bed apparatus 403 after the adjustment and the position coordinate information of the body outside type γ ray detecting part 409 will be input into the respective coordinate converting circuits 471, 472 and 473.

The operation of the radioactive source position measuring apparatus of the present invention shall be explained in the following. In the case of the diagnosis, a resistor marked with a radio-isotope has been injected into the body of the patient 490 and has concentrated on a tumor part 491 and the radio-isotope of the resistor has discharged positrons which have hit nearby electrons to emit γ rays. The endoscope 301 having the body cavity inside γ ray detecting part 320 is inserted into the body cavity of the patient 490 and γ rays are detected with the γ ray detecting part 320 while observing the body cavity wall 492. A fluorescence will be emitted within the scintillator 322 by the γ rays detected within the body cavity and having entered the collimator 321 through the plastic cover 323, will be amplified and photoelectrically converted by the photoelectronic multiplying tube 329 within the data processing apparatus 426 through the glass plate 325 and light guide 326 and will be processed by the processing part 330. While thus detecting the γ rays, the entire body cavity interior is screened to confirm the approximate position of the tumor part 491. When the approximate position of the tumor part 491 is confirmed, the radioactive ray detecting apparatus 402 and bed apparatus 403 will be moved so that the convergent position F of the body outside type γ ray detecting part 409 may meet the position of the endoscope tip part 302. By this positions, both apparatus 402 and 403 will be positioned so that the shutters 464 of the γ ray generating parts 410 may be opened and closed by driving the solenoids 466 alternately with the signals from the solenoid driving apparatus 484 and the output of all the γ ray generating parts 410 may be simultaneously detected by the γ ray sensing circuit 470. At this time, the body cavity inside γ ray detecting part 320 will be operated as a single light quantum CT, the output from the functional part as a single light quantum CT of the γ ray sensing circuit 470 will be input into the position controlling circuit 483, on operating signal will be output to the solenoid driving apparatus 484 and a position controlling signal will be output to the motor driving apparatus 485. The motor driving apparatus 485 will drive the respective motors 486, 487 and 488 on the basis of the signal controlling signal and will instruct the vertically move the pillar 405 of the radioactive ray detecting apparatus 402, to rotate and move forward and rearward the C arm 407, to vertically move the pillar 417 of the bed apparatus 403 and to rotate the bed 418 to position them. In this positioning, X rays may be utilized. When the positioning ends, all the shutters 464 of the γ ray generating parts 410 will be closed and 80 γ ray detectors 460 of the body outside type γ ray detecting part 409 will be operated. In this case, only when the γ rays are sensed with the respective sensor 460 in turn together with the body cavity inside γ ray detecting part 320 and are sensed by both, the distance to the tumor part 491 will be determined from the flying time difference by the γ ray sensing circuit 470. At this time, the sensor 460 will be so strong in the directivity for the position F that, only in case the tumor part 491 is located on the line connecting the sensor 460 and the position F, the γ rays will be detected by the sensors 460. Therefore, by the operated sensors 160 and the respective determined distances, the size (range) and position of the tumor part 491 will be made definite and the tumor part 491 will be obtained as of three-dimensional information of XY2. In order to display the three-dimensional information of this tumor part 491 as overlapped on the ultrasonic picture image obtained with the ultrasonic probe 414, on the basis of the position coordinate information from the motor driving apparatus 485 by the first coordinate converting circuit 471 and in consideration of the position of the ultrasonic probe 414, the three-dimensional information will be converted to be of a coordinate of the ultrasonic picture image, will have the position on the picture image determined and will be synthesized by the adder 470 and the tumor image 494 will be displayed in the ultrasonic image monitor 430 through the frame memory 482. In the same manner, in order to display the three-dimensional information of this tumor part 491 as overlapped on the X ray image obtained with the X ray TV camera 413, on the basis of the position coordinate from the motor driving apparatus 485 by the third coordinate converting circuit 473 and corresponding to the through seeing position of the X ray TV camera 413, the three - dimensional information will be converted to be of a coordinate of the X ray image, will have the position on the picture image determined and will be synthesized by the adder 477 and the tumor image 496 will be displayed in the X ray picture image monitor 428 through the frame memory 480. Thus, by synthesizing, displaying and simultaneously observing the tumor image for the picture images from many fields, the position and size of the tumor will be diagnosed.

According to this embodiment, as radioactive ray detecting parts are provided outside the body and inside the body cavity, the position of the radioactive ray source can be accurately detected and, as the radioactive ray detecting part can be brought near to the affected part, strong radioactive rays will be received and the diagnosing ability will improve.

The X rays and ultrasonic diagnosis need not always be used together and, when X ray images and ultrasonic images are taken in from many directions and the tumor images are overlapped, the diagnosing ability will be further improved. In case the body cavity inside γ ray detecting part 320 is used only as a positron CT for determining the flying time difference, the collimator 321 can be eliminated. The body outside type γ ray detecting parts may be provided in the form of a ring encircling the patient 490 or of an arc so that the patient 490 may be moved and scanned.

Another first example of the body cavity inside radioactive ray detecting part of the endoscope 301 used in the 27th embodiment shall be explained in the following. A tip part 500 of a straight view type endoscope is only illustrated in FIG. 50 and is provided with a cover glass 501, an objective lens 502, an observing optical system and illuminating light guide 504 formed of image guide fibers a collimator 507 having a cover 506 on the front surface as a radioactive ray detecting part 505 and a scintillator 508 in the rear of which a light guide 509 is arranged in the long axial direction of the endoscope. The insertable part to the data processing apparatus are the same as in FIG. 40.

Another second example of the endoscope is shown in FIGS. 51 and 52. A tip part 510 is provided with an illuminating light guide 511, a cover glass 512, an objective lens 513, a first movable prism 514, a collimator 517 having a cover 516 on the front surface as a radioactive ray detecting part 515, a scintillator 518, an image guide fiber 519 arranged as opposed on the entrance surface to and separated from the scintillator 518 and a second prism 520 movable as synchronized with the first prism 514 between the scintillator 518 and image guide fiber 519. In the case of observing the affected part with the endoscope, the first and second prisms 514 and 520 will be positioned as in FIG. 51 and an image will be reflected by the two prisms to enter the image guide fiber 519 on the end surface. In the case of operating the radioactive ray detecting part, the first and second prisms 514 and 520 will be slid as in FIG. 52 so that a fluorescence emitted from the scintillator 518 will enter the image guide fiber 519. The prisms are thought to be moved by the operation of an actuator using a form memorizing alloy or a wire from outside. Though not illustrated, a photoelectronic multiplying tube will be connected to the eyepiece part of the operating part at the time of detecting radioactive rays.

FIG. 53 shows another third example of the endoscope. The same as in an ordinary endoscope, a tip part 521 is provided with an observing optical system 522 having an image guide fiber, an illuminating light guide 523 and a forceps channel 524. A radioactive ray detecting part 525 is formed as a probe, is inserted through the channel 524 from a forceps hole in the operating part to the tip part 521, is formed at the tip of a collimator 527 having a cover 526 and a scintillator 528, is fitted after the scintillator 528 with a light guide 529 coated with a protective tube 530, is extended at the other end out of the operating part and is connected to a photoelectronic multiplying tube within a data processing apparatus.

In the above described respective examples, instead of the light guide connected to the scintillator, such small photoelectronic multiplying tube as a channel of a micro-channel plate may be arranged and may be led to the data processing apparatus through a signal line inserted through the endoscope. Also, instead of the image guide fiber, a solid state imaging device may be arranged.

As explained above, according to the 27th embodiment, as the radioactive ray source position is detected by both signals from the radioactive ray detecting parts provided inside the body cavity and outside the body, the position and size of the radioactive ray source can be accurately measured.

The 28th embodiment of the present invention is shown in FIGS. 54 and 55.

This endoscope 601 is formed mostly of first and second operating parts 602 and 617, a flexible tube part 603 connected in turn to the first operating part 602 and a body cavity insertable part comprising a tip forming part 604 and a collimator 650 made of a non-transparent and radioactive ray attenuating material. An observing part 606 is arranged rotatably within the above mentioned collimator 650 so as to be rotated and driven by a flexible shaft 607 which is fixed at the tip to a handle part 606a (See FIG. 55) of the observing part 606 extended into the tip forming part 604, is inserted through the flexible tube part 603 and is then extended at the rear end into the first operating part 602. A pulley 608 is fixed to the flexible shaft 608 at the rear end. A timing belt 611 is hung on the pulley 608 and an output pulley 610 fixed to the output shaft of a motor 609 which is a rotating and driving source. Further, a slip ring group 614 is fixed to the pulley 608 so as to be contacted by a brush group 615 to which lead wires 616 are connected.

An illuminating window (not illustrated) and a light guide 663 are arranged within the tip forming part 604 adjacent to the above mentioned collimator 650. The light guide 663 is drawn through the flexible tube 603 and first operating part 602, is then extended into the second operating part 617 and is connected to a light source apparatus (not illustrated) through a universal cord 617a from the second operating part 617. An air feeding system and sucking system necessary for the function of the endoscope are omitted.

FIG. 55 is a magnified sectioned view showing the interiors of the above mentioned collimator 650 and tip forming part 604. The above mentioned collimator 650 is formed of a cap-like short cylinder formed on the tip surface of a thick disc and opened on the rear surface and has an observing part 606 rotatably arranged within it. The tip forming part 604 closely fitted at the tip to this collimator 650 is also formed of a comparatively thick short cylinder formed like a donut on the front end surface and opened on the rear surface and is closely fitted in the outer peripheral step part of the front end part to the inner peripheral surface of the rear end part of the above mentioned collimator 650 so as to be integral with the collimator 650. A spiral tube 622 forming the flexible tube part 603 and a sheath coating it are closely fitted at the respective tips to the outer peripheral step part of the rear end part of this tip forming part 604. On a part of the outer periphery of the above mentioned tip forming part 604, a light distributing lens 664 ,is arranged through an outside exposed cover glass 665 and the.- above mentioned light guide 633 is opposed on the tip surface to this light distributing lens 664. A observing window is formed on one side of this collimator 650 and is fitted with a cover glass 651. An imaging device fitting member 655 like a short cylinder opened on the upper and lower surfaces and arranged so that its vertical axis may be at right angles with the axial direction of the insertable part is provided within the above mentioned collimator 650. The opened upper and lower end surfaces of this imaging device fitting member 655 are opposed to the peripheral surface of the collimator 650. A solid state imaging device 657 is arranged within the above mentioned fitting member 655. The above mentioned imaging device fitting member 655 is fitted at one end with an objective lens 658 forming an object image on the above mentioned solid state imaging device 657 and at the other end with a radioactive ray detecting device 640. The above mentioned pipe-like handle part 606a extends sidewise in a part of the central part on the outer peripheral surface of the above mentioned fitting member 625, forms a driving shaft rotating and scanning the solid state imaging device 657 and extends into the tip forming part 604 through a central aperture 604a on the donut-like front end surface of the tip forming part 604. The handle part 606a extended into the tip forming part 604 is rotatably borne by a bearing member 630 such as a bearing fixed to the tip forming part 604 and is tightly fitted and fixed on the small diameter part 606b formed by a step on the outer peripheral surface of the rear end part with a flexible shaft formed by closely winding a conductive resilient wire to be like a coil at the tip. The flexible shaft 607 formed to be doubly wound may be used. A fixing member 632 for integrally fitting the above mentioned bearing member 630 to the forming part 604 is screwed into the forming part 604. A guide tube 633 coating the above mentioned flexible shaft 607 is fitted to this fixing member 632 as fastened with a nut 634.

The flexible shaft 607 is connected to the handle part 606a of the above mentioned fitting member 655. Lead wires 635 connected to the above mentioned solid state imaging device 657 and radioactive ray detecting device 640 are inserted through this flexible shaft 607. The lead wire connected to the above mentioned solid state imaging device 657 is inserted through the universal cord 617a and is connected to a video signal processing circuit 660. The lead wire connected to the above mentioned radioactive ray detecting device 640 is inserted through the universal cord 617a and is connected to a signal amplifying circuit 642.

The output signals of the above mentioned video signal processing circuit 660 and signal amplifying circuit 642 will be synthesized by a displaying circuit 643 and will be input into a monitor 644 in which an object image and radioactive ray information such as a radioactive ray intensity will be displayed.

The operation of this embodiment shall be explained in the following.

In the case of observing an optical image of an object, the imaging device fitting member 655 will be rotated to oppose the solid state imaging device 657 to the observing window. The light returning from the object by the illuminating light will pass through the observing window and will be made to form an image on the solid state imaging device 657 by the objective lens 658. The object image imaged by this solid state imaging device 657 will be displayed on the monitor 644.

When, for example, a likely affected part is discovered while the object image imaged by the solid state imaging device 657 is being observed in the monitor 644, the above mentioned fitting member 655 will be rotated to oppose the radioactive ray detecting device 640 to the observing window. When the observing window is opposed to a cancer, radioactive rays such as γ rays emitted from the cancer will enter the above mentioned observing window, will reach the above mentioned radioactive ray detecting device 640 and will be detected by this radioactive ray detecting device 640. Information such as the intensity of the radioactive rays detected by this radioactive ray detecting device 640 will be displayed on the monitor 644.

In case the above mentioned radioactive ray detecting device 640 is sensitive not only to radioactive rays but also to light, it will be desirable to extinguish or reduce the illuminating light when the radioactive rays are being detected with the above mentioned radioactive ray detecting device 640.

Thus, according to this embodiment, an optical image of the observed part can be observed and the radioactive rays from the observed part can be detected. Therefore, the presence and position of a deep part cancer or lymphatic knot transfer can be easily confirmed. The operating method and curing method can be easily and positively determined.

As the radioactive ray detecting device 640 is integrally provided on the back surface of the solid state imaging device 657, as compared with the case that they are provided as separately arranged, the actual fitting space may be smaller, it will not be necessary to make the outside diameter of the tip larger and to make the rigid tip part longer and the burden on the patient can be reduced.

The observation and radioactive ray detection of the same part can be made and the endoscope image and radioactive ray generating source can be easily made to correspond to each other.

By providing the radioactive ray attenuating member on the end surface on the side reverse to the solid state imaging device 657 of the above mentioned radioactive ray detecting device 640, the observing direction and radioactive ray detecting direction may be made to coincide with each other. Further, by forming the observing window to be long in the peripheral direction or over the entire periphery and rotating the fitting member 655, the observation and radioactive ray detection in a wide range may be made without moving the tip part of the endoscope.

In the above first to 28th embodiments, the radioactive rays are not limited to be γ rays but may be α rays and β rays.

It is apparent that, in this invention, workings modes different in a wide range can be formed on the basis of this invention without deviating from the spirit and scope of the invention. The invention is not restricted by its specific working modes except being limited by the appended claims.

what is claimed is:

1. A radioactive ray detecting endoscope comprising:
an elongated insertable part having a tip part and an observing window located in the tip part;
an imaging means for converting an optical image of an observed cavity, obtained through said observing window, into an electrical signal forming an optical image output, said imaging means having a visual field; and
a radioactive ray detecting means for detecting radioactive rays, said radioactive ray detecting means having a radioactive ray detecting field of view for detecting the radioactive rays generated from said observed cavity located within said visual field of said imaging means and said radioactive ray detecting means for outputting radioactive ray detecting information forming a radioactive ray image.

2. A radioactive ray detecting endoscope according to claim 1 wherein said imaging means comprises an image forming optical system for receiving light returning from said observed cavity and entering said observing window and forming the optical image of said observed cavity and a solid state imaging device for imaging said optical image.

3. A radioactive ray detecting endoscope according to claim 2 wherein said image forming optical system has an optical axis which is bent, said radioactive ray detecting means is provided on said optical axis on one side of said image forming optical system and said radioactive ray detecting endoscope further comprising a collimator surrounding said radioactive ray detecting means, having said radioactive ray detecting field of view, for reducing said radioactive ray detecting field of view.

4. A radioactive ray detecting endoscope according to claim 1 wherein said imaging means has an image forming optical system for receiving light returning from the observed cavity and entering said observing window, an eyepiece part provided on said insertable part at a rear end side thereof, an image transmitting means transmitting the optical image formed by said image forming optical system to said eyepiece part and a television camera removably fitted to said eyepiece part and imaging said optical image.

5. A radioactive ray detecting endoscope according to claim 4 wherein said image forming optical system has an optical axis which is bent, and said image transmitting means has an optical axis which is bent, said radioactive ray detecting means is provided on one of said optical axes on one side of said image forming optical system and said radioactive ray detecting endoscope further comprising a collimator surrounding said radioactive ray detecting means, having a radioactive ray detecting field of view, for reducing said radioactive ray detecting field of view.

6. A radioactive ray detecting endoscope according to claim 2 or 4 further comprising an illuminating means for illuminating inside of said visual field of said imaging means.

7. A radioactive ray detecting endoscope according to claim 1 further comprising a first display means for displaying the optical image of said observed cavity based on the electrical signal from said imaging means and a second display means for displaying said radioactive ray image detected by said radioactive ray detecting means.

8. A radioactive ray detecting endoscope according to claim 7 wherein said first display means for displaying the optical image of the observed cavity and said second display means for displaying the radioactive ray image are a single display means.

9. A radioactive ray detecting endoscope according to claim 1 further comprising a channel formed within said insertable part.

10. A radioactive ray detecting endoscope according to claim 9 further comprising a probe insertable through said channel and having said radioactive ray detecting means in a tip part of said probe.

11. A radioactive ray detecting endoscope according to claim 1 wherein said radioactive ray detecting means has said radioactive ray detecting field of view and said radioactive ray detecting endoscope further comprises a collimator, surrounding said radioactive ray detecting means, for reducing said radioactive ray detecting field of view.

12. A radioactive ray detecting endoscope according to claim 1, further comprising a single solid state imaging device said single solid state image device is used for both said radioactive ray detecting means and said imaging means.

13. A radioactive ray detecting endoscope according to claim 12 further comprising a collimator surrounding said solid state imaging device for reducing said radioactive ray detecting field of view.

14. A radioactive ray detecting endoscope according to claim 11, 3, 5 or 13 wherein said collimator is a member having at least one radioactive ray transmitting part located in the visual field of said imaging means, said member comprising a radioactive ray attenuating material.

15. A radioactive ray detecting endoscope according to claim 14 wherein said radioactive ray attenuating material is selected from a group consisting of lead, tungsten, stainless steel, lead glass, concrete, and mercury.

16. A radioactive ray detecting endoscope according to claim 12 wherein said solid state imaging device has an imaging surface and said radioactive ray detecting endoscope further comprising an optically transparent optical member provided removably in front of the imaging surface of said solid state imaging device.

17. A radioactive ray detecting endoscope according to claim 12 further comprising a collimator and an optical system for transmitting the optical image to said solid state imaging device and for passing said radioactive rays within said collimator.

18. A radioactive ray detecting endoscope according to claim 12 wherein said solid state imaging device has an imaging surface and said radioactive ray detecting endoscope further comprises a member for intercepting entering light and for passing radioactive rays, said member being pasted to the imaging surface of said solid state imaging device to form a radioactive ray detecting part.

19. A radioactive ray detecting endoscope according to claim 12 wherein said solid state imaging device has video pixels and radioactive ray detecting pixels and said video pixels are provided with a radioactive ray attenuating means.

20. A radioactive ray detecting endoscope according to claim 19 wherein said video pixels have a front surface and wherein said radioactive ray attenuating means is an optically transparent optical member, provided on the front surface of said video pixels for attenuating radioactive rays.

21. A radioactive ray detecting endoscope according to claim 16 or 20 wherein said optical member is made of lead glass.

22. A radioactive ray detecting endoscope according to claim 12 further comprising a memorizing means for storing a signal from said slid state imaging device and a control means for storing signals from said solid state imaging device.

23. A radioactive ray detecting endoscope according to claim 2 or 12, further comprising a signal processing means for producing a video signal of said observed cavity based on an output signal of said solid state imaging device, said signal processing means including a) a comparing means for comparing a signal obtained from said solid state imaging device with a reference value and b) a replacement means for replacing a part of said signal exceeding said reference value, as detected by said comparing means, with a predetermined value.

24. A radioactive ray detecting endoscope according to claim 12 further comprising an intercepting means for intercepting entry of light into said solid state imaging device when said radioactive rays are detected using said solid state imaging device.

25. A radioactive ray detecting endoscope according to claim 24 wherein said radioactive ray detecting means includes a) comparing means for comparing an output signal, obtained from said solid state imaging device when entry of light into said solid state device is intercepted by said intercepting means, with a reference value and for detecting that said output signal exceeds said reference value and b) an indicating means for indicating that said radioactive rays are detected when said comparing means detects that said output signal exceeds said reference value.

26. A radioactive ray detecting endoscope according to claim 1, said radioactive ray detecting means having a detecting direction, said imaging means having a visual field direction and wherein said visual field direction of said imaging means and said detecting direction of said radioactive ray detecting means substantially coincide with each other.

27. A radioactive ray detecting endoscope according to claim 1 wherein said radioactive ray detecting means has a scintillator arrangeable within said visual field of said imaging means.

28. A radioactive ray detecting endoscope according to claim 27 wherein said scintillator is a liquid scintillator and a space for sealing said liquid scintillator can be formed in the tip part of said insertable part.

29. A radioactive ray detecting endoscope according to claim 1 wherein said radioactive ray detecting means has a scintillator with a radioactive ray detecting part arranged near the tip part of said insertable part and has an aperture provided on a side opposed to said radioactive ray detecting port of said scintillator.

30. A radioactive ray detecting endoscope according to claim 1 further comprising a second radioactive ray detecting means, arranged outside said body cavity, for detecting radioactive rays from inside the body cavity.

31. A radioactive ray detecting endoscope according to claim 30 further comprising a third radioactive ray detecting means for detecting radioactive rays within said visual field of said imaging means.

32. A radioactive ray detecting endoscope according to claim 1 wherein said radioactive ray detecting means has a plurality of radioactive ray detectors each of said detectors having different detecting direction.

33. A radioactive ray detecting endoscope according to claim 1 wherein said imaging means and said radioactive ray detecting means are integral with each other.

* * * * *